US009085538B2

(12) United States Patent
Casar et al.

(10) Patent No.: US 9,085,538 B2
(45) Date of Patent: Jul. 21, 2015

(54) PROCESS FOR THE PREPARATION OF KEY INTERMEDIATES FOR THE SYNTHESIS OF STATINS OR PHARMACEUTICALLY ACCEPTABLE SALTS THEREOF

(75) Inventors: Zdenko Casar, Ljubljana (SI); Damjan Sterk, Ljubljana (SI); Marko Jukic, Ljubljana (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 41 days.

(21) Appl. No.: 13/812,458

(22) PCT Filed: Jul. 25, 2011

(86) PCT No.: PCT/EP2011/003714
§ 371 (c)(1),
(2), (4) Date: Oct. 25, 2013

(87) PCT Pub. No.: WO2012/013325
PCT Pub. Date: Feb. 2, 2012

(65) Prior Publication Data
US 2014/0051854 A1    Feb. 20, 2014

(30) Foreign Application Priority Data

Jul. 26, 2010 (EP) .................................. 10170739

(51) Int. Cl.
*C07D 239/12* (2006.01)
*C07D 239/42* (2006.01)
*C07C 45/68* (2006.01)
*C07C 49/807* (2006.01)
*C07D 215/14* (2006.01)
*C07D 239/46* (2006.01)
*C07C 49/86* (2006.01)
*C07D 215/12* (2006.01)

(52) U.S. Cl.
CPC .............. *C07D 239/42* (2013.01); *C07C 45/68* (2013.01); *C07C 49/807* (2013.01); *C07C 49/86* (2013.01); *C07D 215/12* (2013.01); *C07D 215/14* (2013.01); *C07D 239/46* (2013.01)

(58) Field of Classification Search
CPC .................................................... C07D 239/02
See application file for complete search history.

(56) References Cited

U.S. PATENT DOCUMENTS

2003/0125355 A1    7/2003 Tatsuta et al.

FOREIGN PATENT DOCUMENTS

| EP | 0 521 471 A1 | 1/1993 |
|---|---|---|
| WO | WO 95/11898 A1 | 5/1995 |
| WO | WO 01/04100 A1 | 1/2001 |
| WO | WO 03/064382 A2 | 8/2003 |
| WO | WO 2004/041787 A1 | 5/2004 |
| WO | WO 2006/100689 A1 | 9/2006 |
| WO | WO 2007/007119 A1 | 1/2007 |
| WO | WO 2007/017117 A1 | 2/2007 |
| WO | WO 2008/05334 A2 | 5/2008 |
| WO | WO 2008/059519 A2 | 5/2008 |
| WO | WO 2008/072078 A1 | 6/2008 |
| WO | WO 2008/151510 A1 | 12/2008 |
| WO | WO 2010/086438 A1 | 8/2010 |

OTHER PUBLICATIONS

Acemoglu et al., "A New and Efficient Synthesis of the HMG—CoA Reductase Inhibitor Pitavastatin", Helevetica Chimica Acta, vol. 90, pp. 1069-1081 (2007)
Andrushko et al., "A New Approach to the Total Synthese of Rosuvastatin", Eur. J. Org. Chem., pp. 847-853 (2008).
Hiyama et al., "Synthesis of Artificial HMG—CoA Reductase Inhibitors Based on the Olefination Strategy", Bull. Chem. Soc. JPN., vol. 68, pp. 364-372 (1995).
Jia et al., "Efficient Solvent-Free Synthese of Quinolines Promoted by BiCl3", Letters in Organic Chemistry, vol. 3, pp. 289-291 (2006).
Jia et al., "Rapid and Efficient synthesis of poly-substituted quinolines assisted by p-toluene sulphonic acid under solvent-free conditions: comparitive study of microwave irradiation versus conventional heating", Org. Biomol. Chem., vol. 4, pp. 104-110 (2006).
Minami et al., "A Novel Enantioselective Synthese of HMG—CoA Reductase Inhibitor NK-104 and a Related Compound", Tetrahedron Letters, vol. 33, No. 49, pp. 7525-7526 (1992).
Miyachi et al., "A Novel Synthetic Method of HMG—CoA Reductase Inhibitor NK-104 Via a Hydroboration-Cross Coupling Sequence", Tetrahedron Letters, vol. 34, No. 51, pp. 8267-8270 (1993).
Suzuki et al., "First Systematic Chiral Synthesis of Two Pairs of Enantionmers with 3,5-Dihydroxyheptenoic Acid Chain, Associated with a Potent Synthetic Statin NK-104", Bioorganic & Medicinal Chemistry Letters, vol. 9, pp. 2977-2982 (1999).
Suzuki et al., "Practical Synthesis of Quinoline Nucleus of NK-104", Heterocycles, vol. 50, No. 1, pp. 479-483 (1999)
Suzuki et al., "Synthesis and Biological Evaluations of Quinoline-based HMG—CoA Reductase Inhibitors", Bioorganic & Medicinal Chemistry, vol. 9, pp. 2727-2743 (2001).
Takahashi at al., "A New Synthesis of HMG—CoA Reductase Inhibitor Nk-104 Through Hydrosilylation-Cross Coupling Reaction", Tetrahedron Letters, vol. 34, No. 51, pp. 8263-8266 (1993).
Takano et al., "Enantioconvergent Synthesis of a Promising HMG—CoA Reductase Inhibitor NK-104 from Both Enantiomer of Epichlorohydrin", Tetrahedron: Asymmetry, vol. 4, No. 2, pp. 201-204 (1993).

*Primary Examiner* — Noble Jarrell
*Assistant Examiner* — John S Kenyon
(74) *Attorney, Agent, or Firm* — Arent Fox LLP

(57) ABSTRACT

The invention relates to commercially viable process for the synthesis of key intermediates for the preparation of statins, in particular Rosuvastatin and Pitavastatin or respective pharmaceutically acceptable salts thereof. A new simple and short synthetic route for key intermediates is presented which benefits from the use of cheap and readily available starting materials, by which the conventionally most frequently used DIBAL-H as reducing agent can be avoided.

10 Claims, No Drawings

PROCESS FOR THE PREPARATION OF KEY INTERMEDIATES FOR THE SYNTHESIS OF STATINS OR PHARMACEUTICALLY ACCEPTABLE SALTS THEREOF

CROSS-REFERENCE TO RELATED APPLICATION

This application is a National Stage entry of International Application No. PCT/EP2011/003714, filed Jul. 25, 2011, which claims priority to European Application No. 10170739.6, filed Jul. 26, 2010, the entire specifications, claims and drawings of which are incorporated herewith by reference.

FIELD OF THE INVENTION

The invention relates to commercially viable process for the synthesis of key intermediates for the preparation of Rosuvastatin and Pitavastatin or respective pharmaceutically acceptable salts thereof as representatives of the group of 3-hydroxy-3-methylglutaryl coenzyme A (HMG-CoA) reductase inhibitors.

BACKGROUND OF THE INVENTION

HMG-CoA reductase inhibitors are commonly referred to as "statins". Statins are therapeutically effective drugs used for reducing low density lipoprotein (LDL) particle concentration in the blood stream of patients at risk for cardiovascular disease by taking the place of HMG-CoA in the enzyme enabled through the similarity of statins and HMG-CoA on a molecular level. By inhibiting HMG-CoA reductase, statins block the pathway for synthesizing cholesterol in the liver. Several statins have been discovered and synthetic routes for their production have been established. Among the synthesizable statins there are Rosuvastatin, Pitavastatin, Cerivastatin, Lovastatin, Atorvastatin, Fluvastatin, Simvastatin and Pravastatin. Due to the complicated molecular structures of these chiral compounds multi step protocols with certain key intermediates are common for their preparation.

In the synthesis of Rosuvastatin and its pharmaceutically acceptable salts N-(4-(4-fluorophenyl)-5-(bromomethyl)-6-isopropylpyrimidin-2-yl)-N-methylmethanesulfonamide (PMDBR), N-(4-(4-fluorophenyl)-5-(hydroxymethyl)-6-isopropylpyrimidin-2-yl)-N-methylmethanesulfonamide (PMDOH); N-(4-(4-fluorophenyl)-6-isopropyl-5-methylpyrimidin-2-yl)-N-methylmethanesulfonamide (PMDME); N-(4-(4-fluorophenyl)-5-(formyl)-6-isopropylpyrimidin-2-yl)-N-methylmethanesulfonamide (PMDCHO) and (E)-N-(4-(4-fluorophenyl)-6-isopropyl-5-(3-oxoprop-1-en-1-yl)pyrimidin-2-yl)-N-methylmethanesulfonamide (PMDOPEN) are possible intermediates. Rosuvastatin calcium, chemically described as bis[(E)-7-[4-(4-fluorophenyl)-6-isopropyl-2-[methyl(methylsulfonyl)amino]pyrimidin-5-yl] (3R,5S)-3,5-dihydroxyhept-6-enoic acid] calcium salt, is a synthetic lipid-lowering agent that acts as an inhibitor of 3-hydroxy-3-methylglutaryl-coenzyme A (HMG-CoA) reductase (HMG-CoA Reductase inhibitor). Rosuvastatin calcium is used in the treatment of hypercholesterolemia and mixed dyslipidemia.

EP 521471 A1 discloses Rosuvastatin and a process for its preparation, among others by a process comprising a step of preparing N-(4-(4-fluorophenyl)-5-(hydroxymethyl)-6-isopropylpyrimidin-2-yl)-N-methylmethanesulfonamide by reduction of a suitable ester derivative thereof with diisobutylaluminium hydride (DIBAL-H) as a reduction reagent.

In the synthesis of Pitavastatin and its pharmaceutically acceptable salts 3-(bromomethyl)-2-cyclopropyl-4-(4-fluorophenyl)quinoline (PTVBR), (2-cyclopropyl-4-(4-fluorophenyl)quinolin-3-yl)methanol (PTVOH); 2-cyclopropyl-4-(4-fluorophenyl)-3-methylquinoline (PTVME); 2-cyclopropyl-4-(4-fluorophenyl)quinoline-3-carbaldehyde (PTVCHO) and (E)-3-(2-cyclopropyl-4-(4-fluorophenyl)quinolin-3-yl)acrylaldehyde (PTVOPEN) are possible intermediates. Pitavastatin calcium, chemically described as bis [(3R,5S,6E)-7-[2-cyclopropyl-4-(4-fluorophenyl)quinolin-3-yl]-3,5-dihydroxyhept-6-enoic acid] calcium salt, is a synthetic lipid-lowering agent that acts as an inhibitor of 3-hydroxy-3-methylglutaryl-coenzyme A (HMG-CoA) reductase (HMG-CoA Reductase inhibitor). Pitavastatin calcium is used in the treatment of hypercholesterolemia and mixed dyslipidemia.

Scheme 1
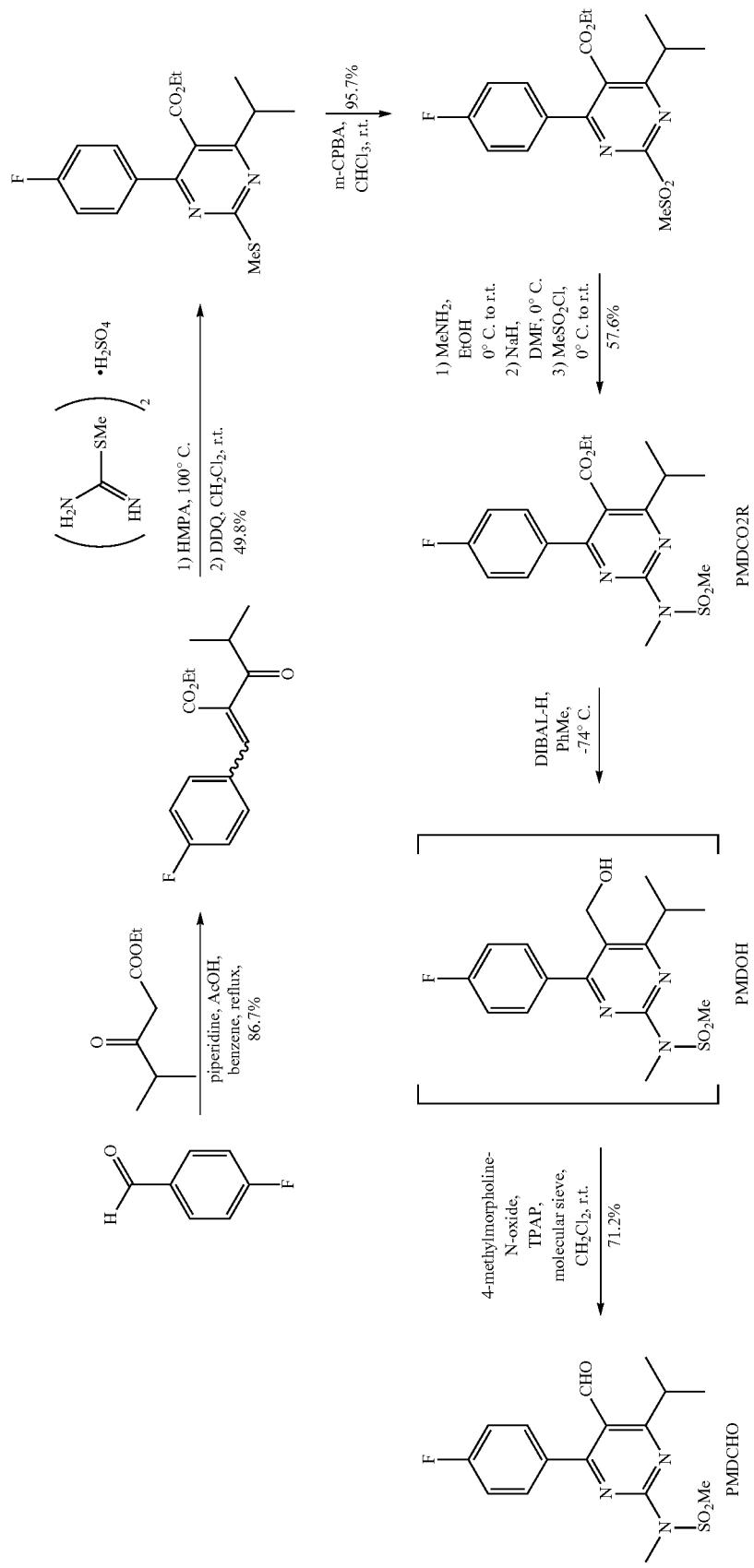

Furthermore, WO2008/059519 A2 also describes the preparation of Rosuvastatin via N-(4-(4-fluorophenyl)-5-(hydroxymethyl)-6-isopropylpyrimidin-2-yl)-N-methyl-methanesulfonamide as intermediate obtained by reduction of a suitable ester (PMDCO2R) thereof by means of DIBAL-H.

International patent application WO2007/017117 A1 discloses the preparation of Rosuvastatin via N-(4-(4-fluorophenyl)-5-(bromomethyl)-6-isopropylpyrimidin-2-yl)-N-methylmethanesulfonamide as the intermediate. This intermediate is prepared by nucleophilic substitution of N-(4-(4-fluorophenyl)-5-(hydroxymethyl)-6-isopropylpyrimidin-2-yl)-N-methylmethanesulfonamide by means of HBr as the source of nucleophile.

A process for preparing 2-amino-4-(4-fluorophenyl)-6-alkylpyrimidine-5-carboxylates (PMDCO2R) is described in PCT Pat. Appl. WO 2001/004100, 2001:

Scheme 2

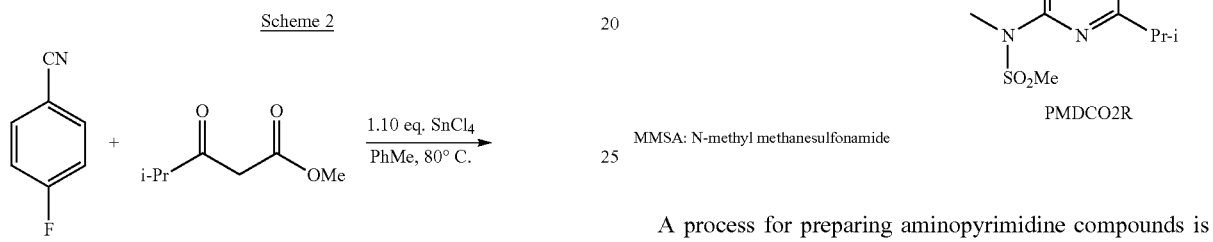

MMSA: N-methyl methanesulfonamide

A process for preparing aminopyrimidine compounds is disclosed in PCT Pat. Appl. WO 2003/006439, 2003:

Scheme 3

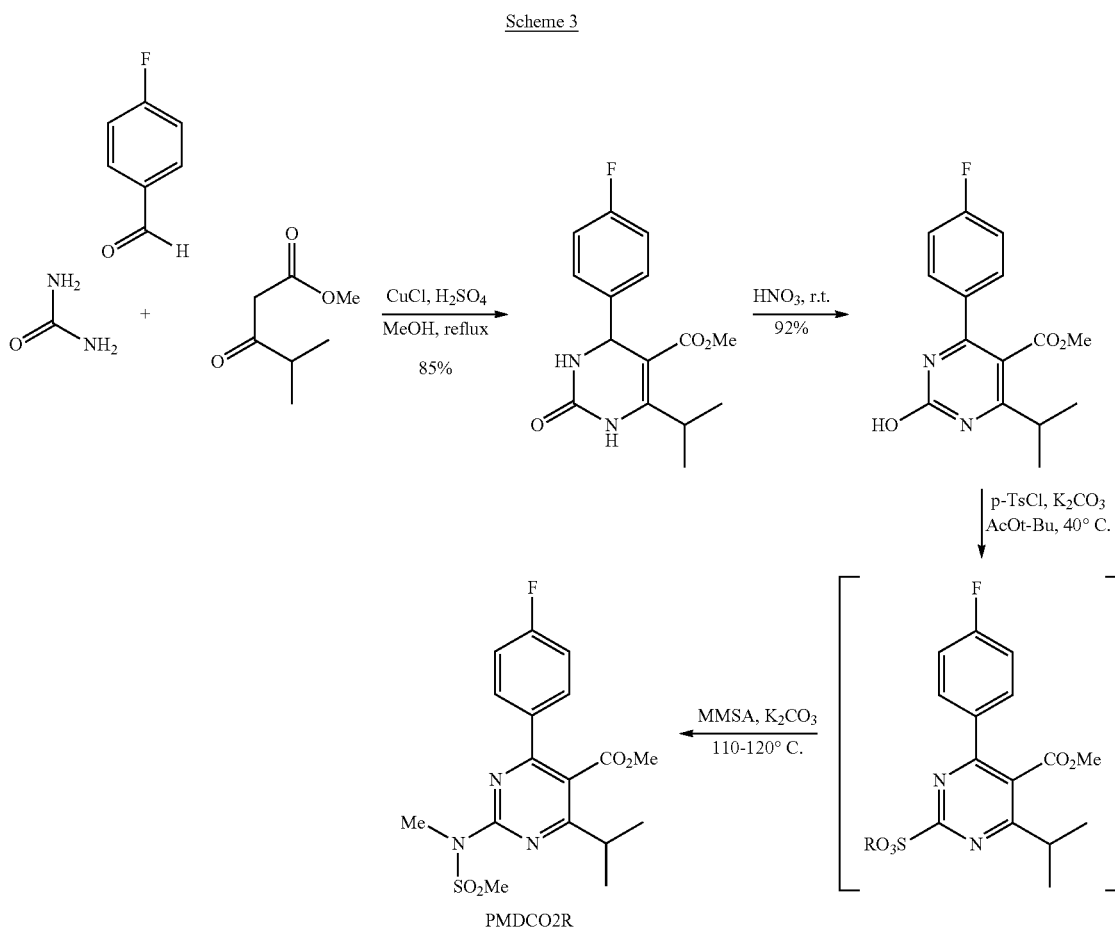

MMSA = 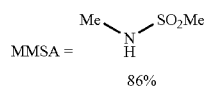

86%

A synthesis of PMDCHO without application of PMDOH disclosing also the preparation of the diketone DK is described in *Eur. J. Org. Chem.* 2008, 847-853:

Scheme 4

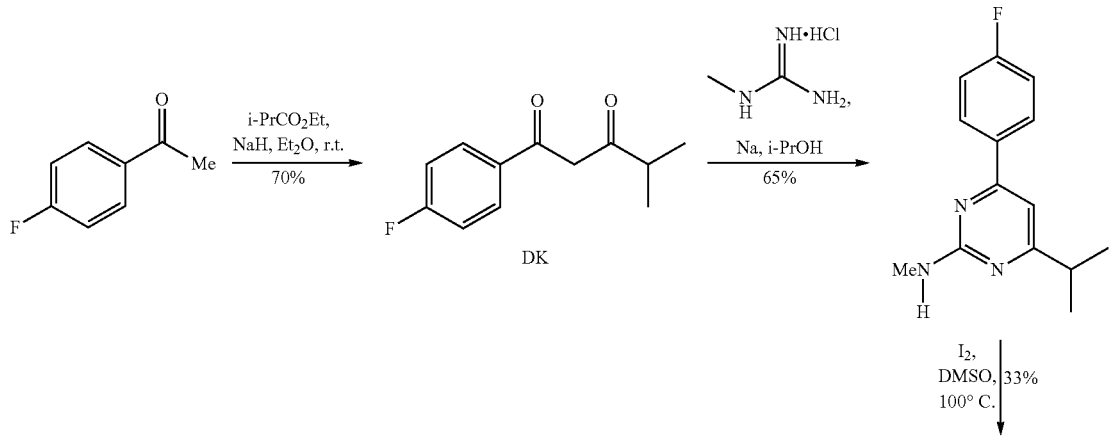

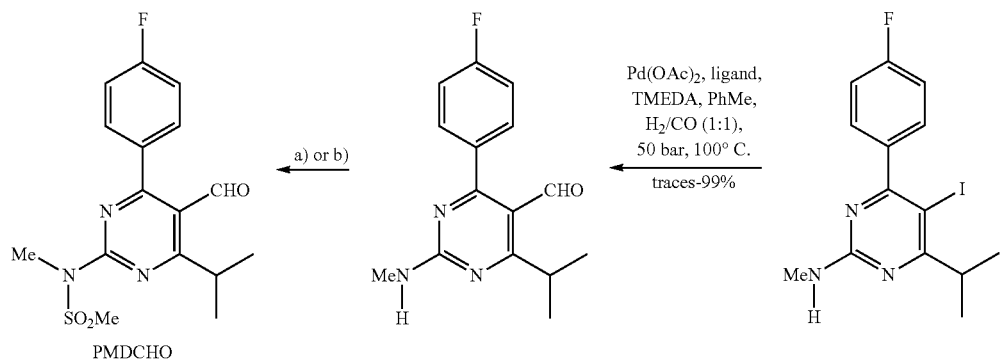

PMDCHO
a) MeSO₂Cl, Et₃N, CH₂Cl₂, 0° C. to r.t.: 30%
b) NaH, DMF, 0° C., then MeSO₂Cl at 0° C. to r.t.: 55%

A method for the preparation of 4-(fluorophenyl)-6-isopropyl-2-(N-methyl-N-methylsulfonylamino)-5-formyl-pyrimidine (PMDCHO) is disclosed in PCT Pat. Appl. WO 2008/151510, 2008:

Scheme 5

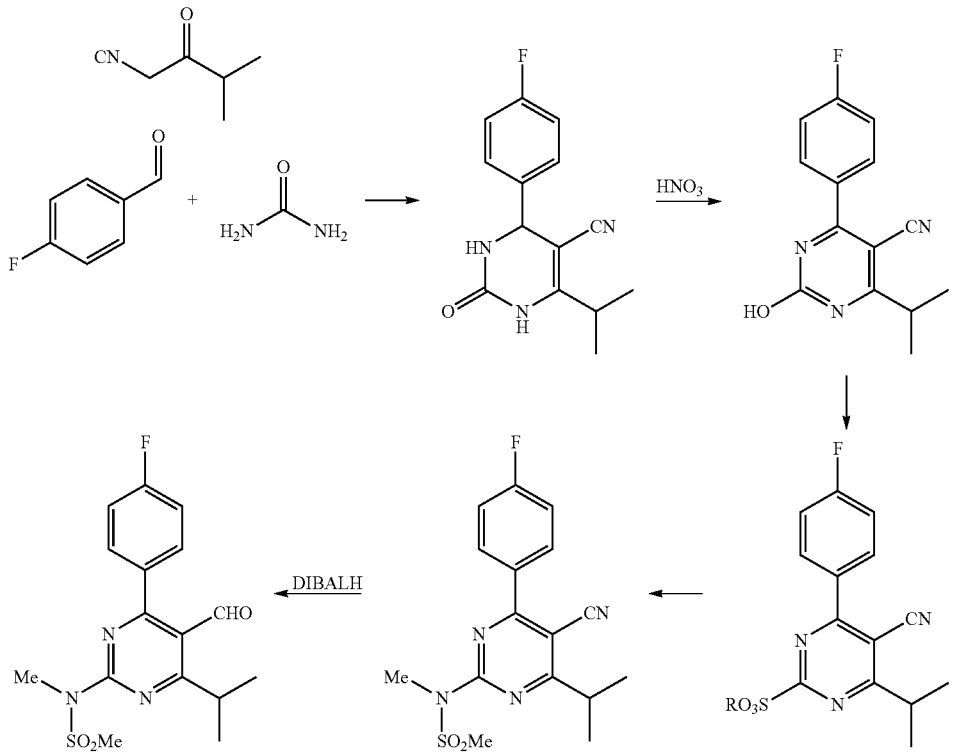

A preparation of (E)-N-(4-(4-fluorophenyl)-5-(3-hydroxyprop-1-enyl)-6-isopropylpyrimidin-2-yl)-N-methylmethanesulfonamide (MCALDKOH) and aldehyde derivative (E)-N-(4-(4-fluorophenyl)-6-isopropyl-5-(3-oxoprop-1-enyl)pyrimidin-2-yl)-N-methylmethanesulfonamide (PMDOPEN) starting from N-(4-(4-fluorophenyl)-5-(formyl)-6-isopropylpyrimidin-2-yl)-N-methylmethanesulfonamide (PMDCHO) is described in patent literature under WO 2006100689, WO 2008053334, WO 2008072078 and IP.com Journal, 6(12B), 30; 2006 including Wittig or Wittig-Horner-Emmons reactions:

Scheme 6

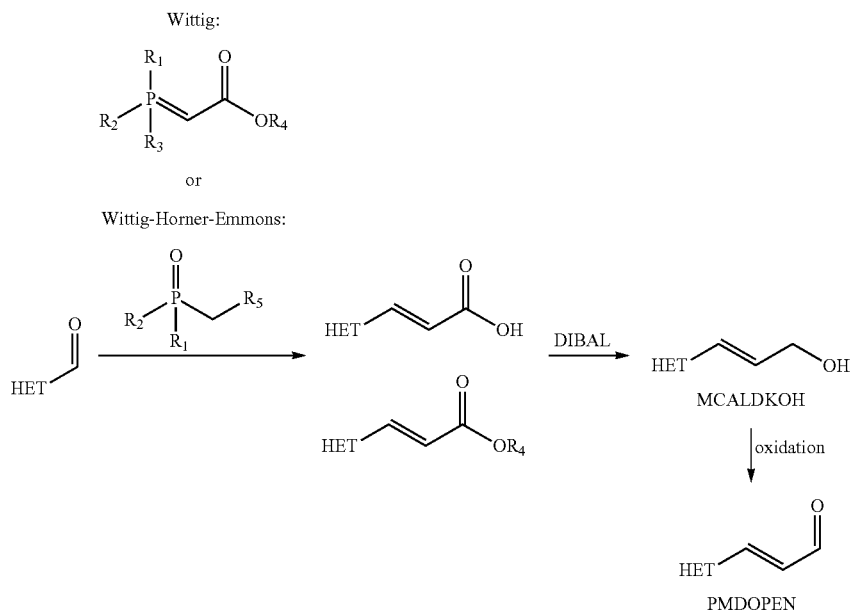

HET = 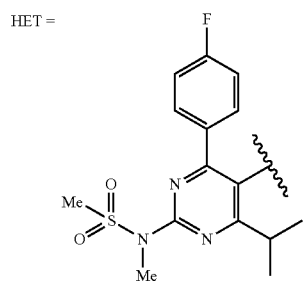
A preparation of (E)-N-(4-(4-fluorophenyl)-6-isopropyl-5-(3-oxoprop-1-enyl)pyrimidin-2-yl)-N-methylmethanesulfonamide (PMDOPEN) is disclosed in WO 2007/007119 A1 including Suzuki coupling and subsequent reduction with DIBALH:
Scheme 7
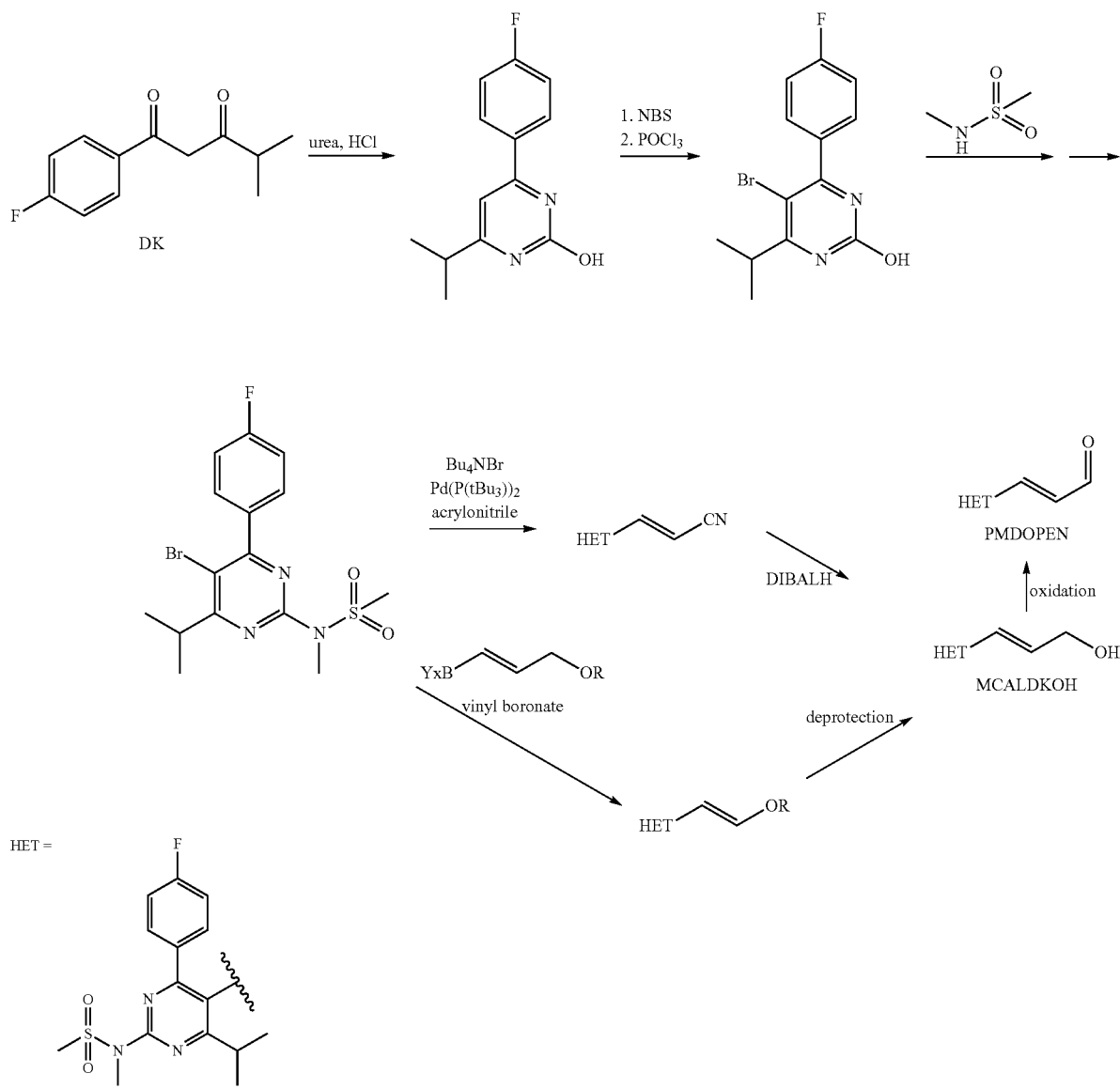
HET =

It is known from the art that PMDBR, PMDOH, PMDCHO and PMDOPEN can be used as key intermediates for the preparation of Rosuvastatin as shown in the scheme below:

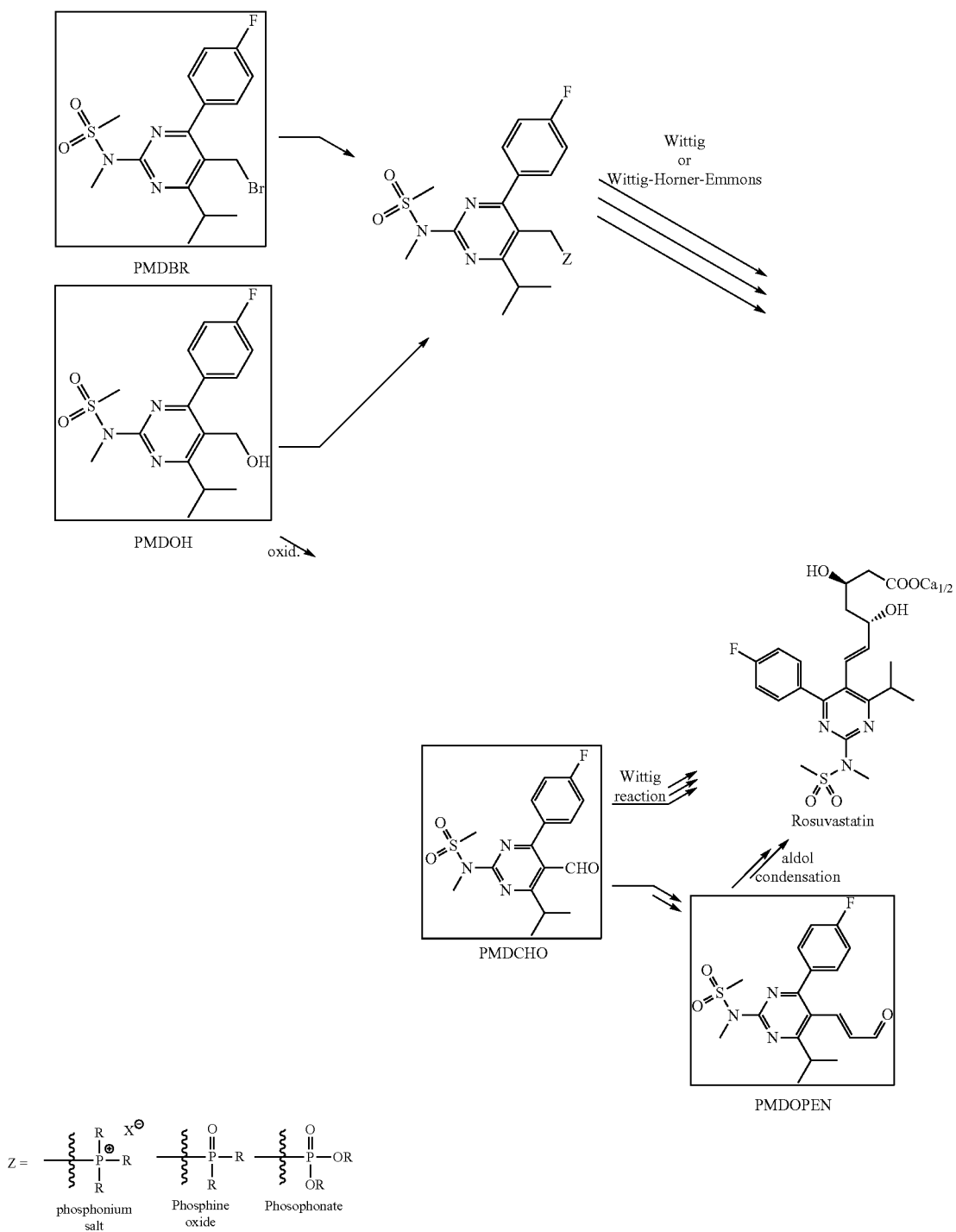

PMDBR and PMDOH can be used for the preparation of PMD phosphine oxides, phosphonium salts and phosphonate esters.

A method for the preparation of Pitavastatin is disclosed in *Tetrahedron Lett.* 1992, 33, 7525-7526, and includes HWE olefination of Pitavastatin phosphine oxide derivatized heterocycle with acetonide protected side chain:

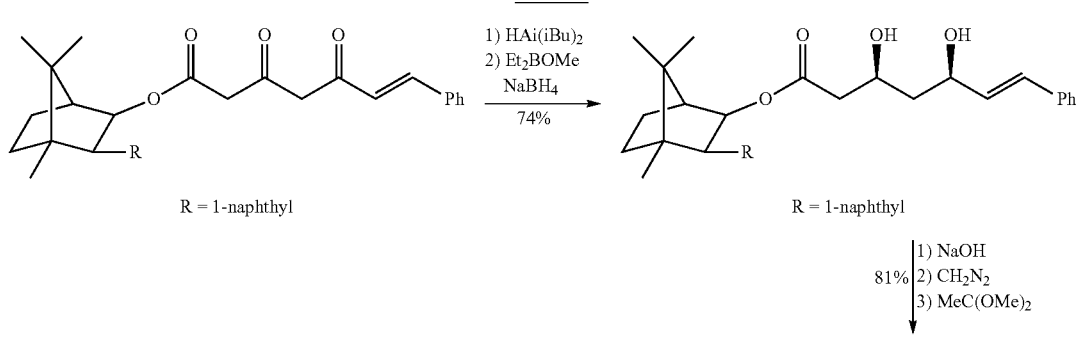

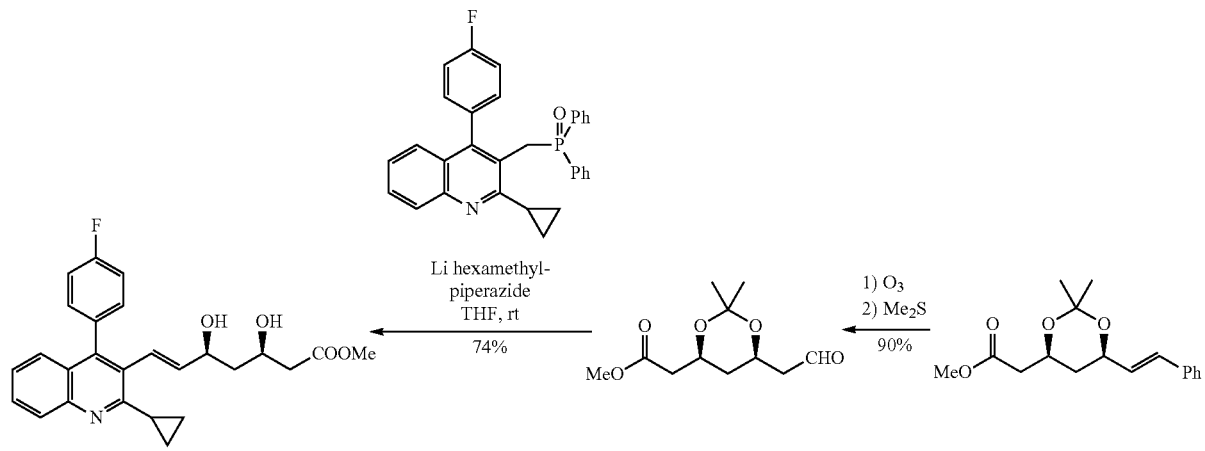

Synthesis of Pitavastatin via cross-coupling reaction is disclosed in *Tetrahedron Lett.* 1993, 34, 8263-8266, and in *Tetrahedron Lett.* 1993, 34, 8267-8270.

A method for the preparation of Pitavastatin via epichlorohydrin is described in *Tetrahedron: Asymmetry* 1993, 4, 201-204.

Synthesis of Pitavastatin heterocycle and Pitavastatin molecule assembly via aldol condensation reaction is disclosed in *Bioorg. Med. Chem. Lett.* 1999, 9, 2977-2982, and *Bioorg. Med. Chem.* 2001, 9, 2727-2743:

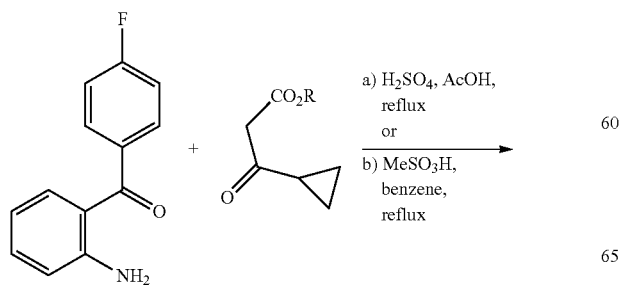

-continued

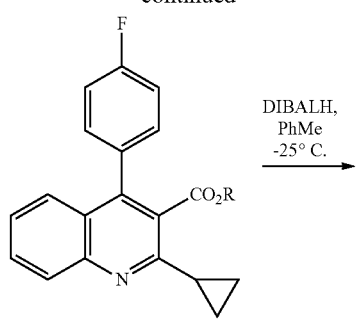

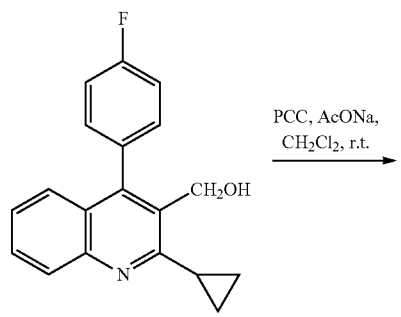

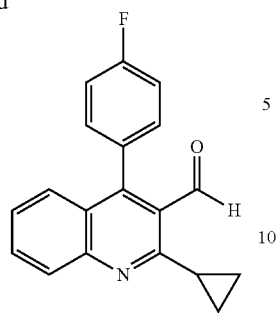
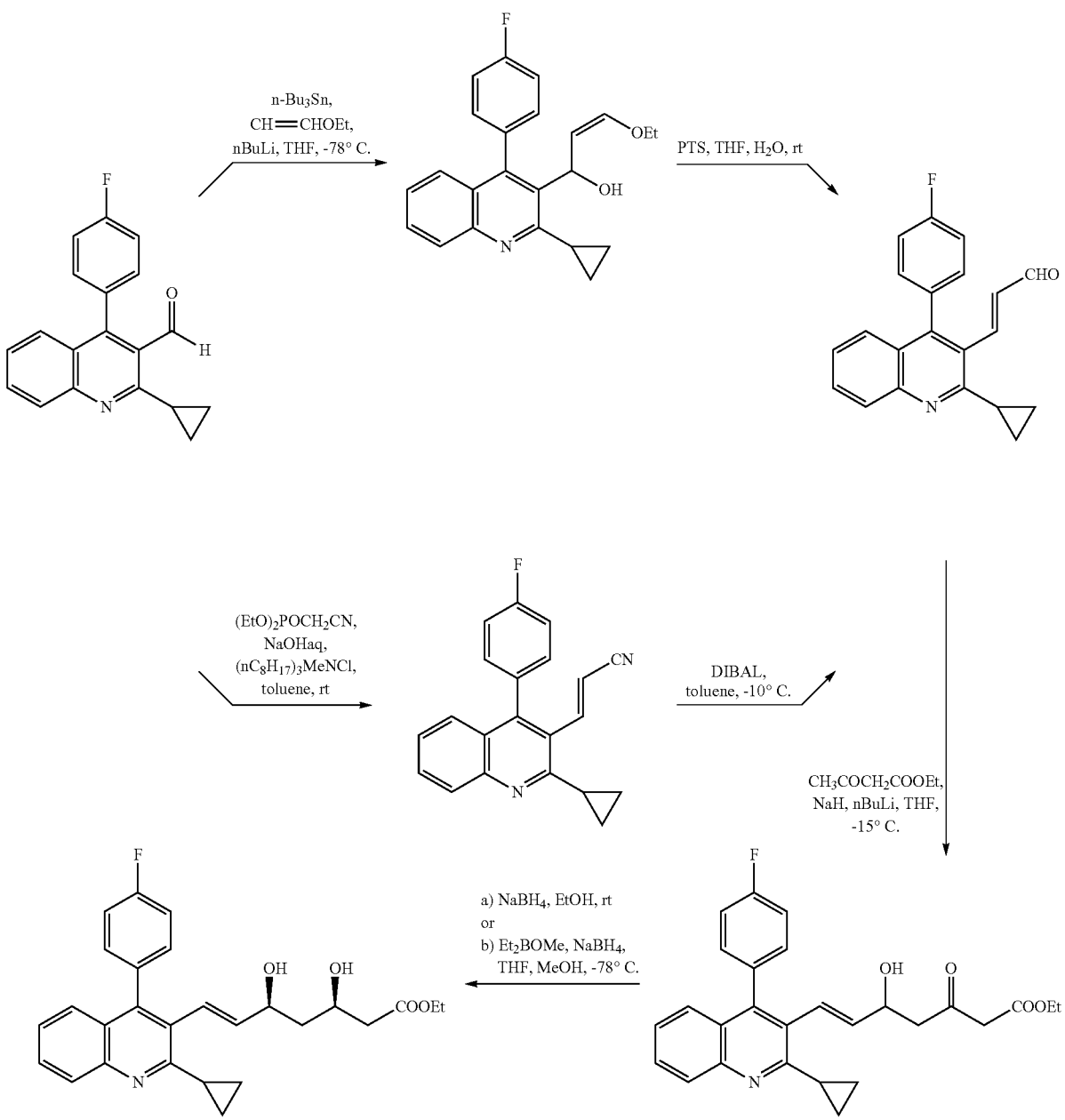
Scheme 11

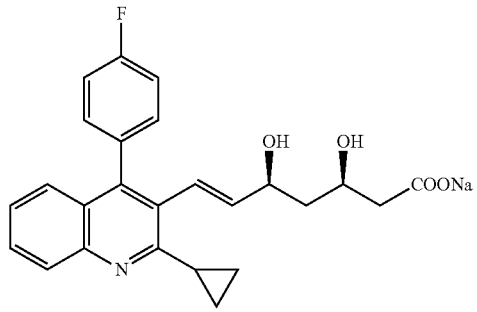
PCT application WO 2003/064382 describes a method for preparation of Pitavastatin by asymmetric aldol reaction, in which titanium complex is used as a catalyst.
HWE route to Pitavastatin by utilization of 3-formyl substituted Pitavastatin heterocycle is disclosed in *Helv. Chim. Acta* 2007, 90, 1069-1081:
Scheme 12
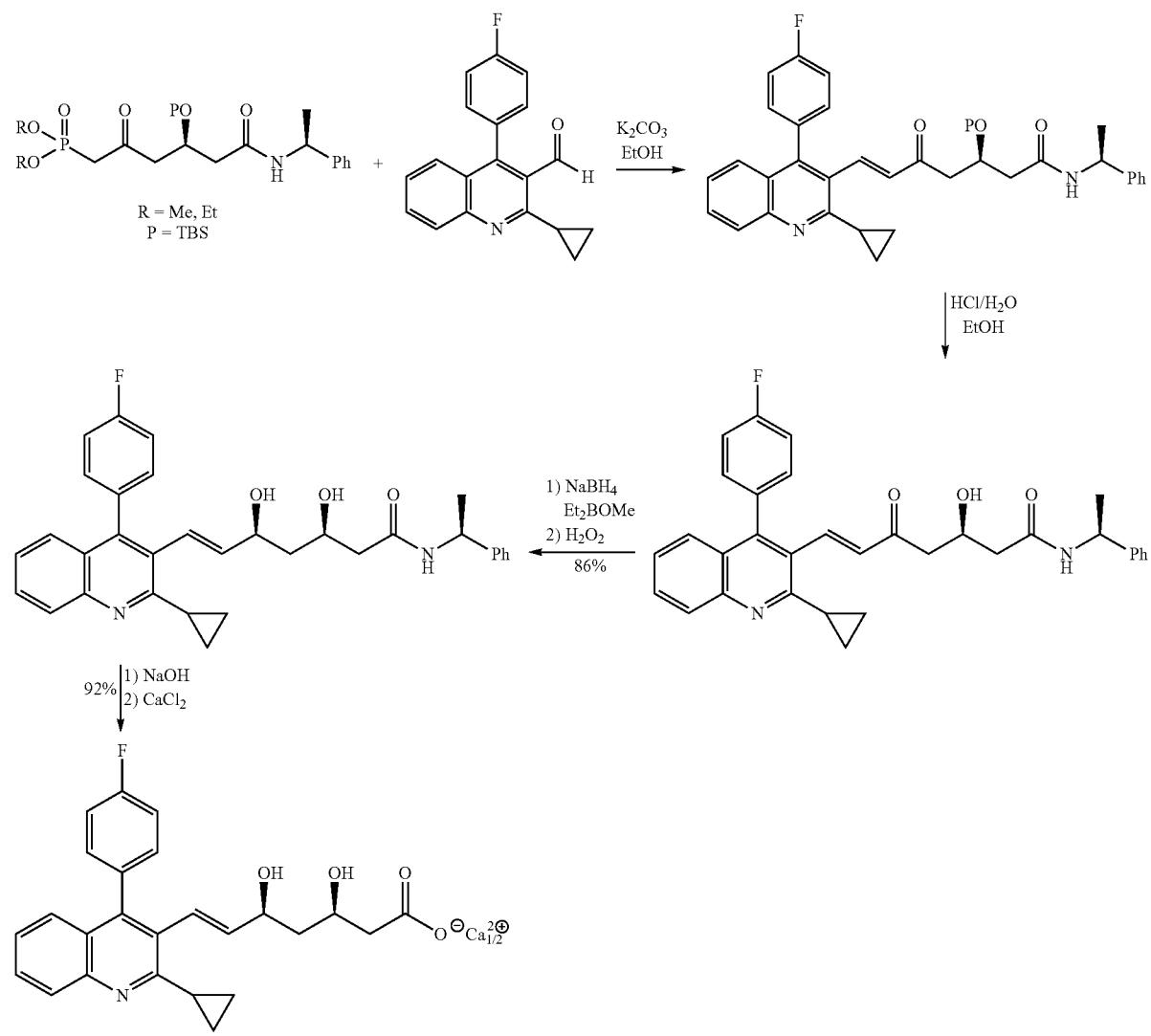

Methods for preparation of Pitavastatin heterocycle derivatives are described in *Bull. Chem. Soc. Jpn.* 1995, 68, 364-372, *Heterocycles* 1999, 50, 479-483, *Lett. Org. Chem.* 2006, 3, 289-291, and in *Org. Biomol. Chem.* 2006, 4, 104-110, as well as in the international patent applications WO 95/11898 and WO 2004/041787.

WO 95/11898 and *Bull. Chem. Soc. Jpn.* 1995, 68, 364-372 disclose synthesis of PTVBR from PTVOH with PBr₃:

Scheme 13

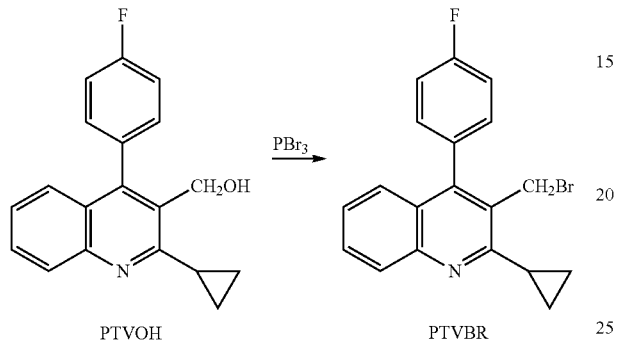

PTVOH         PTVBR

SUMMARY OF THE INVENTION

Aspects, advantageous features and preferred embodiments of the present invention summarized in the following items, respectively alone or in combination, contribute to solving this and other objects of the invention:

(1) A process for preparing a heterocyclic aldehyde of formula (I) or (II)

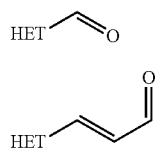 (I)

(II)

wherein HET denotes a substituted or unsubstituted heterocyclic group, the process comprising a) for the preparation of the aldehyde (I)

a-1) either subjecting a heterocyclic methyl derivative (III-Me)

HET—CH₃      (III-Me)

wherein HET is defined as above,
to a radical bromination reaction to obtain an intermediate (IV)

(IV)

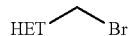

and subsequently to a nucleophilic substitution reaction to obtain a compound of formula (V)

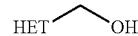 (V)

and oxidizing the compound of formula (V) to the heterocyclic aldehyde (I)

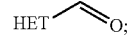 (I)

or a-2) converting a compound of formula (III-al)

(III-al)

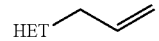

wherein HET is defined as above,
to a compound of the formula (VII) by isomerization (VII)

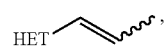

and oxidizing the compound of formula (VII) to the heterocyclic aldehyde (I)

(I)

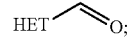

or b) for the preparation of the aldehyde (II)
converting the compound of formula (III-al) defined above to a compound of formula (VIII)

(VIII)

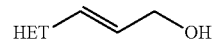

wherein HET is defined as above,
and oxidizing the compound of formula (VIII) to the heterocyclic aldehyde (II)

(II)

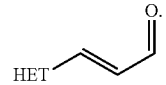

(2) A process for preparing a heterocyclic aldehyde of formula (I)

(I)

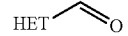

wherein HET denotes a substituted or unsubstituted heterocyclic group, the process comprising subjecting a heterocyclic methyl derivative (III-Me)

   (III-Me)

wherein HET is defined as above,
to a radical bromination reaction to obtain an intermediate (IV)

   (IV)

and oxidizing the compound of formula (IV) to the heterocyclic aldehyde (I)

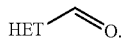   (I)

The present invention comprises new pathways for the synthesis of key intermediates (I) and (II), which are particularly valuable and useful for the preparation of Rosuvastatin and Pitavastatin from simple starting materials. By the process according to the present invention a high yield synthesis for the heterocyclic aldehydes (I) and (II) is achieved starting from the heterocyclic methyl compound (III-Me) and allyl compound (III-al), respectively. Further, using cheap, simple and harmless starting materials the present invention facilitates a short and economically reasonable process for the preparation of the aforementioned key intermediates.

The present invention features a synthetic pathway wherein the use of tedious and demanding reagents such as DIBAL-H can be avoided. While in most literature procedures the use of DIBAL-H is necessary when the corresponding carboxylic acids derivatives or nitriles are reduced in order to obtain aldehyde (I) or (II) respectively, the synthetic procedure disclosed herein provides an improved concept wherein this particular reaction step can be dispensed with. Moreover, as shown in the literature corresponding carboxylic acids derivatives or nitriles are prepared by longsome multi-step protocols. The use of DIBAL-H is accompanied by a series of disadvantages, namely it is tedious in handling because it requires reduced temperatures, and it is very reactive, expensive and hazardous. By avoiding the use of DIBAL-H a convenient synthetic route is established which does not require special conditions such as dry solvents and cryogenic temperatures.

Further in the alternative embodiment starting from formula (III-al) an elegant synthetic pathway to the elongated aldehyde (II) is provided. The syntheses proceed via intermediates which have not been reported before for the preparation of Rosuvastatin and Pitavastatin respectively.

(3) The process according to item 1 or item 2, wherein HET is a group comprising a substituted or unsubstituted heterocycle selected from the group of saturated or unsaturated ring systems, wherein at least one of the ring forming atoms is a nitrogen or an oxygen. In particular the heterocycle is selected from the group of substituted or unsubstituted pyridines, pyrimidines, imidazoles, indoles, quinolines, furans and pyrroles. In a preferred embodiment of the present invention HET is a heterocyclic group selected from the group of substituted pyridines, substituted indoles, substituted pyrroles, substituted pyrimidines and substituted quinolines, respectively. Yet in another preferred embodiment of the present invention HET is a heterocyclic group selected from the group of 2-(4-fluorphenyl)-5-isopropyl-3-phenyl-4-(phenylcarbamoyl)pyrrol-1-yl, 3-(4-fluorphenyl)-1-(isopropyl)-1H-indol-2-yl, 4-(4-fluorophenyl)-5-(methoxymethyl)-2,6-bis(isopropyl)pyridin-3-yl, 4-(4-fluorophenyl)-2-(N-methylmethanesulfonamido)-6-(isopropyl)pyrimidin-5-yl, 2-cyclopropyl-4-(4-fluorophenyl)quinolin-3-yl substituents.

(4) The process according to item 1 or item 2, wherein in a preferred embodiment the heterocyclic group HET is a substituted pyrimidine of the structure (a)

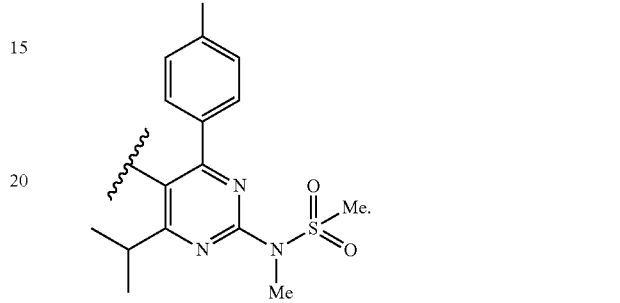   (a)

(5) The process according to item 1 or item 2, wherein in a preferred embodiment the heterocyclic group HET is a substituted quinoline of the structure (b)

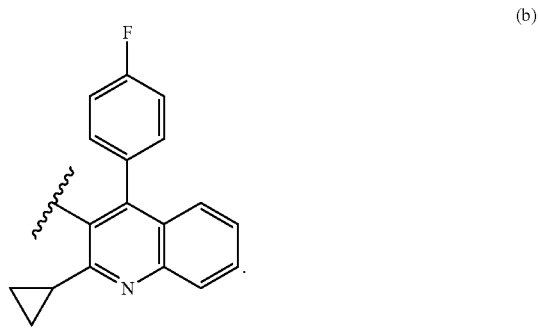 [SMILES: *c1c(C2CC2)nc2ccccc2c1-c1ccc(F)cc1]   (b)

(6) A process for preparing a heterocyclic alkyl derivative of formula (IIIa)

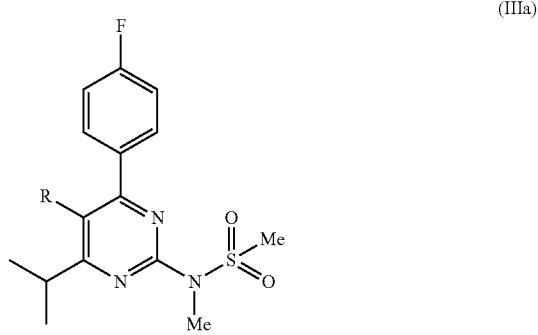   (IIIa)

wherein R is a straight or branched, saturated or unsaturated, optionally substituted alkyl moiety, preferably a straight alkyl moiety, more preferably a methyl or an allyl group, the process comprising:
converting the diketone compound of formula (XIIIa) to an alkylated diketone of formula (XIVa)

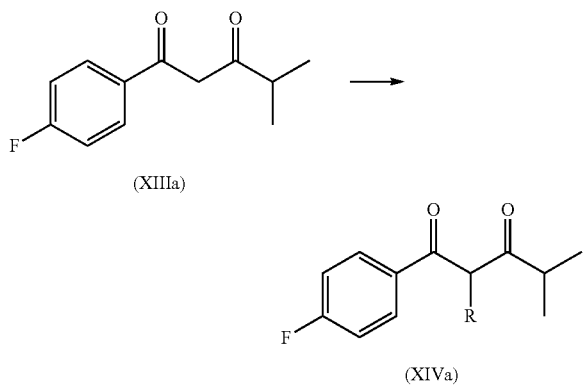

wherein R is as described above,
reacting the alkylated diketone (XIVa) with N-methyl guanidine or a salt thereof (e.g. hydrochloride) to a heterocyclic compound of formula (XVa)

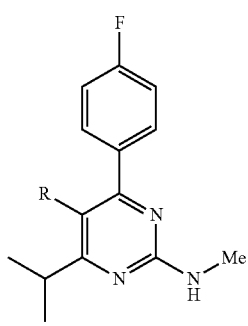

wherein R is as described above, and
converting the heterocyclic compound of formula (XVa) to a sulfonated alkyl heterocycle of formula (IIIa)

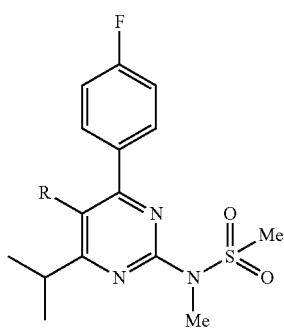

wherein R is as described above.

The synthetic route as described herein represents a simple and short process for the preparation of key intermediate (IIIa). Starting point of this elegant synthetic pathway is the diketone (XIIIa). (XIIIa) can readily and easily be prepared by known procedures, for example by the procedure published in *Eur. J. Org. Chem.*, 2008, 847. According to the present invention (XIIIa) is converted to compound (XIVa) by an efficient alkylation reaction. The reaction proceeds beneficially in high yields. Compound (XIVa) is then converted by reaction with N-methyl guanidine hydrochloride to heterocycle (XVa). This reaction step can simply and efficiently be performed in the presence of a base. In a final reaction step (XVa) is converted to key intermediate (IIIa). In all steps inexpensive starting materials are used comprising, for example, N-methyl guanidine hydrochloride, methanesulfonyl chloride, methyl iodide, allyl bromide, sodium dicarbonate, cesium carbonate and water making the synthetic route described herein a simple, short (three steps) and economically reasonable. Further only mild reaction conditions are applied which facilitates an easy scale up to commercial and industrial demands.

A schematic illustration and various steps of item 4 can be depicted from the following Scheme 14:

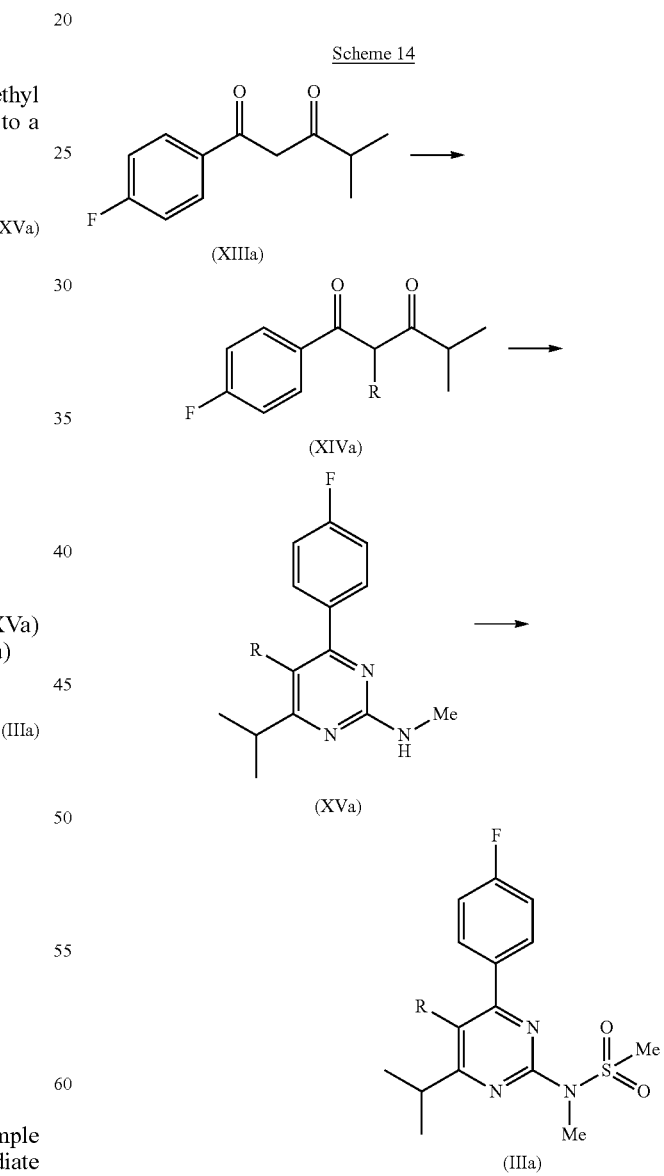

(7) A process for preparing a heterocyclic alkyl derivative of formula (IIIb),

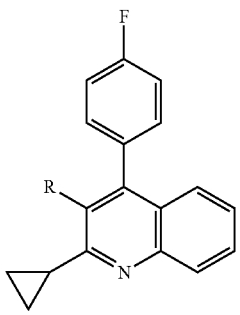

wherein R is a straight or branched, saturated or unsaturated, optionally substituted alkyl moiety, preferably a straight alkyl moiety, more preferably a methyl or an allyl group, the process comprising:

providing a cyclopropylketone compound of formula (XIIb)

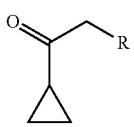

wherein R is as described above, and reacting the compound of formula (XIIb) with 2-amino-4'-fluorobenzophenone to obtain heterocyclic alkyl compound of formula (IIIb)

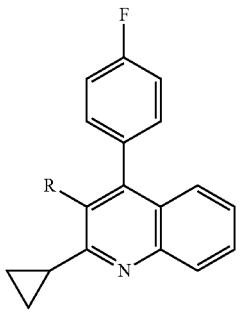

wherein R is as described above.

(8) The process according to item 6, wherein 1-(4-fluorophenyl)-2,4-dimethylpentane-1,3-dione (XIIIa) is converted to the diketone (XIVa)

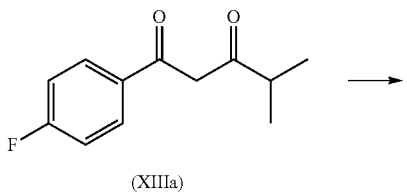

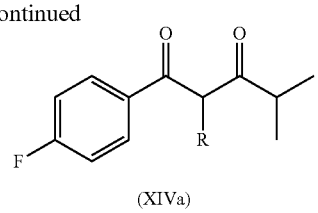

comprising an alkylation reaction in the presence of a base with R being a straight or branched, saturated or unsaturated, optionally substituted alkyl moiety, preferably a straight alkyl moiety, more preferably a methyl or an allyl group.

The alkylating agent is supposed to be an alkyl electrophile. Therefore the alkylating agent is selected from electrophilic alkyl sources which generally are alkyl cations. The corresponding anions comprise halides, carbonates, sulfates, phosphates, triflate, tosylate, benzenesulfonate, ethanesulfonate, methanesulfonate, fluorosulfonates and the like.

In a preferred embodiment of the present invention R is a methyl group and the methylating agent is selected from the group consisting of iodomethane, dimethyl sulfate, trimethyl phosphate, dimethyl carbonate, methyl triflate, methyl tosylate, methyl benzenesulfonate, methyl ethanesulfonate, methyl methanesulfonate, and methyl fluorosulfonate, in particular it is iodomethane.

In another preferred embodiment of the present invention R is an allyl group and the allylating agent is selected from the group of allyl halides and is suitably allyl bromide. The alkylating agent is preferably added in slight excess to the molar stoichiometric amount based on compound of the formula (XIIIa).

(9) The process according to item 6, wherein the diketone of formula (XIVa) is converted to the heterocycle (XVa) in a cyclization reaction with N-methyl guanidine or a salt thereof

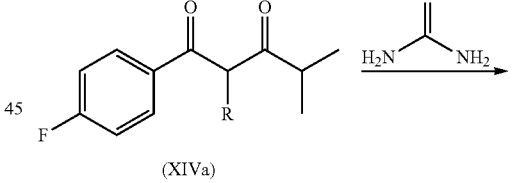

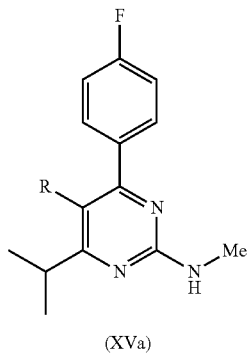

in the presence of a base wherein R is a straight or branched, saturated or unsaturated, optionally substituted alkyl moiety, preferably a straight alkyl moiety, more preferably a methyl or an allyl group.

The source of N-methyl guanidine can be the compound itself, but it can also be selected from derivatives thereof e.g. salts thereof. In a preferred embodiment of the present invention the N-methyl guanidine source is a salt, for example, the hydrochloride.

(10) The process according to item 6, wherein the heterocycle (XVa) is converted to the heterocyclic methyl derivative (IIIa)

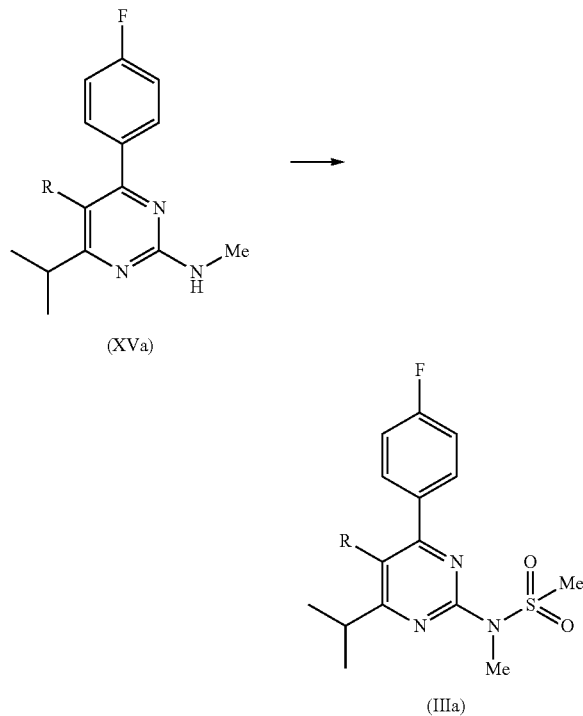

in the presence of a base wherein R is a straight or branched, saturated or unsaturated alkyl moiety, preferably a straight alkyl moiety, more preferably a methyl or an allyl group.

The sulfonization reaction described herein aims to structural modification at the amino group attached to the heterocycle (XVa). The base used for this reaction step is selected from the group consisting of inorganic basic salts and organic bases. The particular structural modification as described herein beneficially requires an electrophilic methanesulfonyl sources such as methanesulfonyl halides. The addition of the methanesulfonyl source is preformed best when particular condition are provided, whereas it is noted that these preferred conditions are not meant to limit the present invention to these particular embodiments. Among these embodiments it is beneficial when (XVa) and the base are stirred in the organic solvent before the methanesulfonyl source is added. Another preferred embodiment of the present invention is that the reaction mixture is cooled below room temperature and that methanesulfonyl source is added at decreased temperatures below room temperature.

(11) The process according to item 7, wherein providing the cyclopropylketone (XIIb) comprises converting suitable cyclopropyl derivatives to the cycloproylketone (XIIb).

Various beneficial embodiments of the process of item 11 can be summarized by the following scheme:

Scheme 15

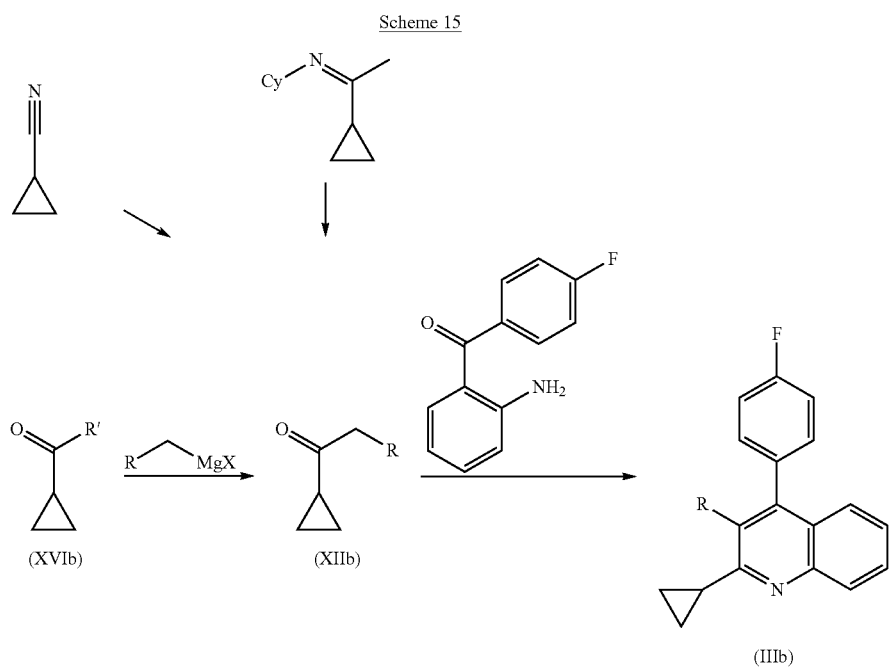

-continued

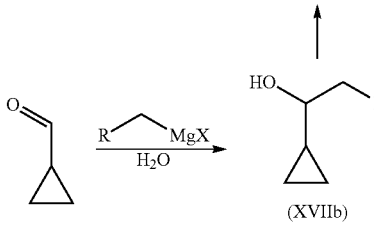

(XVIIb)

In Scheme 15 for compound (XVIb) substituent R' is selected from a group consisting of electron withdrawing groups comprising alkoxy, arylmethoxy, hydroxyl, N,O-dialkylhydroxylamino and halides. R is a straight or branched, saturated or unsaturated, optionally substituted alkyl moiety, preferably a straight alkyl moiety, more preferably a methyl or an allyl group.

The process under item 11 describes the short and simple synthesis of key intermediate (IIIb) for the preparation of Pitavastastin. The preparation benefits from simple starting materials which have to be converted in one or optionally two reaction step to the precursor molecule of the formula (XIIb). Consequently, the intermediate (IIIb) can be prepared in two or three reaction steps respectively from readily available starting materials. Intermediate compound of the formula (IIIb) has not been reported in relation with the preparation of Pitavastatin and therefore opens new and innovative synthetic pathways thereof.

(12) The process according to item 11, wherein providing the cyclopropylketone (XIIb) comprises reacting derivatives of cyclopropanecarboxylic acid (XVIb) with an alkyl Grignard reagent,

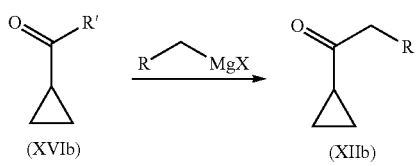

(XVIb)     (XIIb)

wherein R' is selected from a group consisting of electron withdrawing groups comprising alkoxy, arylmethoxy, hydroxyl, N,O-dialkylhydroxylamino, halides, preferably chloride and ethoxy, and R is a straight or branched, saturated or unsaturated, optionally substituted alkyl moiety, preferably a straight alkyl moiety, more preferably a methyl or an allyl group.

The Grignard reagent preferably is an alkyl magnesium halide, preferably a chloride, bromide or iodide. The reaction is preferably carried out under exclusion of moisture. The reaction step represents a simple and fast method of providing the cyclopropylketone (XIIb) starting from readily available compounds.

In a particular embodiment of the present invention R'=H and cyclopropylcarbaldehyde is reacted with an alkyl Grignard reagent with aqueous work up yielding an intermediate (XVIIb). The intermediate (XVIIb) is subsequently oxidized by means of common oxidizing agents in organic chemistry comprising but not being limited to 4-methylmorpholine-N-oxide in the presence of catalytic amounts of tetrapropylammonium perruthenate (TPAP), pyridinium chlorochromate (PCC), pyridinium dichromate (PDC), hydrogen peroxide, 2,2,6,6-tetramethylpiperidine-1-oxyl (TEMPO) in the presence of trichloroisocyanuric acid (TCICA), dimethyl sulfoxide with acetanhydride, and dimethyl sulfoxide with oxalyl chloride (Swern oxidation method), preferably 2,2,6,6-tetramethylpiperidine-1-oxyl (TEMPO) in the presence of trichloroisocyanuric acid (TCICA), and dimethyl sulfoxide with acetanhydride.

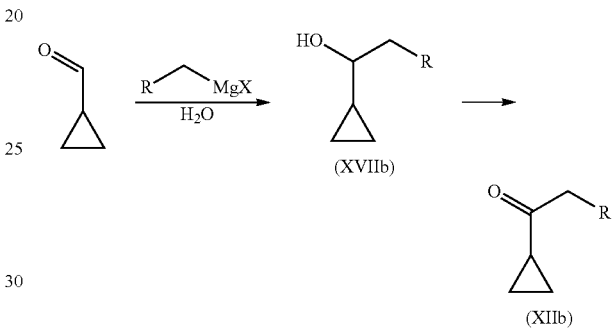

(XVIIb)

(XIIb)

(13) The process according to item 11, wherein providing the cyclopropylketone of formula (XIIb) comprises converting 1-cyclopropyl-1-N-cyclohexylimidoethane to the cyclopropylketone of formula (XIIb)

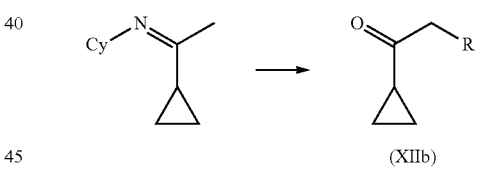

(XIIb)

The conversion 1-cyclopropyl-1-N-cyclohexylimidoethane to the cyclopropylketone of formula (XIIb) proceeds via an alkylation reaction preferably with electrophilic alkyl sources. Thus the alkylating agent is suitably supposed to be an alkyl electrophile. The alkylating agent is preferably selected from electrophilic alkyl sources which generally are alkyl cations. The corresponding anions comprise halides, carbonates, sulfates, triflates, fluorosulfonates and the like. In a preferred embodiment of the present invention R is a methyl group and the methylating agent is selected from the group consisting of iodomethane, dimethyl sulfate, dimethyl carbonate, methyl triflate and methyl fluorosulfonate, in particular it is iodomethane. In another preferred embodiment of the present invention R is an allyl group and the allylating agent is selected from the group of allyl halides and is in particular allyl bromide.

(14) The process according to item 11, wherein providing the cyclopropylketone of formula (XIIb) comprises reacting cyclopropyl nitrile with nucleophilic alkyl sources and subsequent work up in the presence of water.

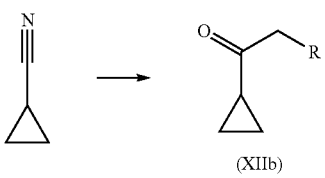

The nucleophilic alkyl sources comprise alkyl Grignard reagents such as alkyl magnesium halide, preferably a chloride, bromide and iodide.

(15) The process according to item 7, wherein converting the cyclopropylketone of formula (XIIb) by reaction with 2-amino-4'-fluorobenzophenone to the heterocyclic methyl derivative (IIIb) requires the presence of an acid.

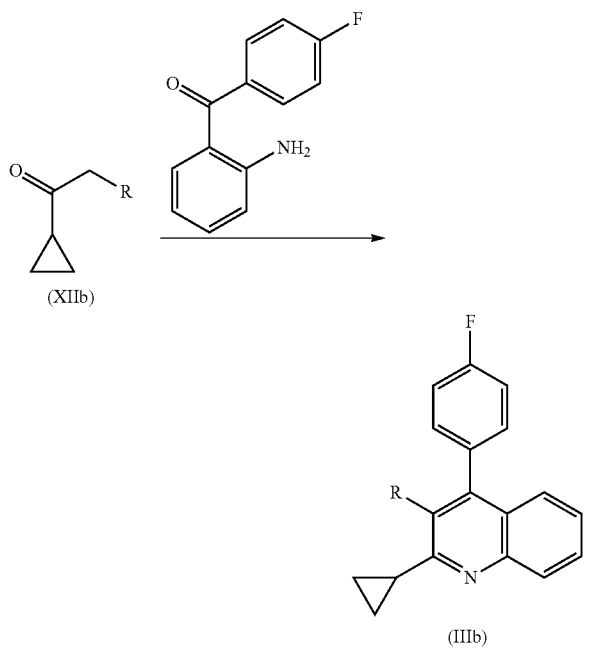

The acid is selected from the group consisting of organic or inorganic acids, diluted or concentrated, comprising but not being limited to hydrochloric acid, sulfuric acid, nitric acid, phosphorous acid, acetic acid, hydrobromic acid, triflic acid, trifluoroacetic acid, methanesulfonic acid, para tuluenesulfonic acid and the like.

(16) The process according to any one of items 1 and 3 to 7, wherein for the preparation of the alcohol (V) the conversion of the heterocyclic methyl derivative (III-Me) proceeds in a one pot reaction

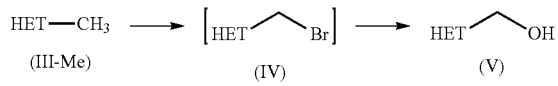

wherein HET is as defined herein.

The conversion of (III-Me) to (V) according to the present application provides an elegant and short process which reduces the expense of labor, material and chemicals by saving practically one complete reaction step. Thus the process according to item 15 is economically and ecologically attractive. The intermediate (IV) can be converted to the alcohol (V) without prior isolation of (IV). Further, the bromination reaction is suitably carried out as a radical bromination using preferably mild N-bromoamide as brominating agent under visible or ultra violet radiation. This is advantageous over bromination reactions using phosphorous tribromide or hydrobromic acid as brominating agents since these brominating agents are either toxic (PBr$_3$) or corrosive and aggressive (H Br) and in this relation difficult to handle. Therefore no special reaction conditions are necessary in order to deal with these problematic properties. Further, conversion of compound (IV) to (V) is accomplished under mild reaction conditions and by means of very cheap and ecologically friendly chemicals. Thus in both steps of the one pot reaction cheap chemicals and mild conditions are applied. In particular, the N-bromoamide as a brominating agent N-bromoamide is selected from the group consisting of N-bromoacetamide, N,N-dibromobenzene sulfonamides, N-bromosuccinimide, N-bromophthalimide, N-bromoglutarimide, 3-bromo-hydantoin and 1,3-dibromo-5,5-dimethyl-hydantoin, preferably it is N-bromosuccinimide. In a preferred embodiment of the invention the bromination reaction is performed without the use of a radical former. In another preferred embodiment of the invention the bromination reaction is carried out in a flow mode. For the aqueous nucleophilic substitution converting the bromide (IV) to the alcohol (V) cheap bases can be used selected from the group consisting of inorganic basic salts comprising carbonates, hydrides and hydroxides, preferably from preferably potassium and sodium carbonates, most preferably it is sodium bicarbonate.

(17) The process according to any one of items 1 and 3 to 7, wherein for the preparation of the aldehyde (I) the alcohol (V) is oxidized with a common oxidizing agent

wherein HET is as defined herein.

(18) The process according to any one of items 2 to 7, wherein for the preparation of the aldehyde (I) the alkylbromide (IV) is oxidized with a common oxidizing agent

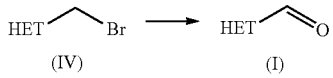

wherein HET is as defined herein.

By oxidizing compound (IV) or (V) as described in the present application a simple reaction pathway for the synthesis of aldehyde (I) is presented starting from the heterocyclic methyl compound (III-Me). In comparison to prior procedures of aldehyde (I) an easier and more economic production is facilitated.

The oxidation of (V) can be carried out in the presence of a prevalent oxidizing agent in organic chemistry comprising but not being limited to 4-methylmorpholine-N-oxide in the presence of catalytic amounts of tetrapropylammonium perruthenate (TPAP), pyridinium chlorochromate (PCC), pyridinium dichromate (PDC), hydrogen peroxide, 2,2,6,6-tetramethylpiperidine-1-oxyl (TEMPO) in the presence of trichloroisocyanuric acid (TCICA), dimethyl sulfoxide with acetanhydride and dimethyl sulfoxide with oxalyl chloride (Swern oxidation method), preferably 2,2,6,6-tetramethylpiperidine-1-oxyl (TEMPO) in the presence of trichloroisocyanuric acid (TCICA), and dimethyl sulfoxide with acetanhydride.

The intermediate (IV) can also serve for direct conversion to aldehyde (I) via Kornblum oxidation whereat dimethyl sulfoxide in the presence of a base is used as an oxidizing agent. Optionally an iodide salt is applied in Kornblum oxidation to facilitate the reaction.

(19) The process according to any one of items 1 and 3 to 7, wherein for the preparation of the aldehyde (I) isomerizing the heterocyclic allyl derivatives (III-al) to the heterocyclic 1-propene (VII) is performed in the presence of a base and a phase transfer catalyst

wherein HET is as defined herein.

Using a phase transfer catalyst is associated with many advantages and is therefore desirable. The amount of organic solvent is reduced and the reaction temperature is often decreased. A process having a step with the use of a phase transfer catalyst being incorporated is therefore economically and ecologically interesting and a contribution to green chemistry. In a preferred embodiment of the present invention the phase transfer catalyst is selected from the group consisting of N-methyl-N,N,N-trioctylammonium chloride, benzyltrimethylammonium chloride and hexadecyltributylphosphonium bromide, preferably N-methyl-N,N,N-trioctylammonium chloride

(20) The process according to any one of items 1 and 3 to 7, wherein for the preparation of the aldehyde (I) the compound of the formula (VII) is oxidized

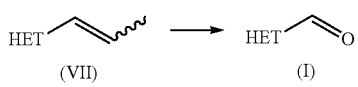

wherein HET is as defined herein.

The various embodiments of items 19 and 20 can be summarized by the following Scheme 16:

Scheme 16

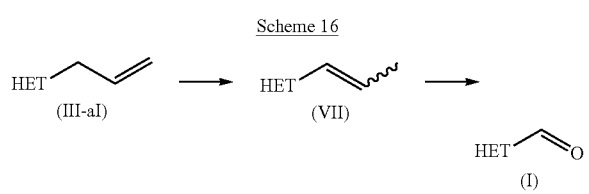

The oxidation of the propene derivative (VII) to the aldehyde (I) proceeds via double bond cleavage upon reaction with a potent oxidation agent. Suitable oxidation agents are for example dimethyldioxirane, either readily prepared or in situ generated by reacting potassium peroxymonosulfate (KHSO$_5$.KHSO$_4$.K$_2$SO$_4$, oxone) with acetone preferably in the presence of ruthenium trichloride, and ozone wherein the side product of the conversion is acetaldehyde.

(21) The process according to any one of items 1 and 3 to 7, wherein for the preparation of the aldehyde (II) compound (III-al) is converted to the heterocyclic alcohol (VIII)

either by bromination and subsequent nucleophilic substitution in a one pot reaction or by epoxidation of the exocyclic double bond and subsequent conversion of a compound of the formula (IX), wherein HET is as defined herein.

The various embodiments of items 19 can be summarized by the following Scheme 17:

Scheme 17

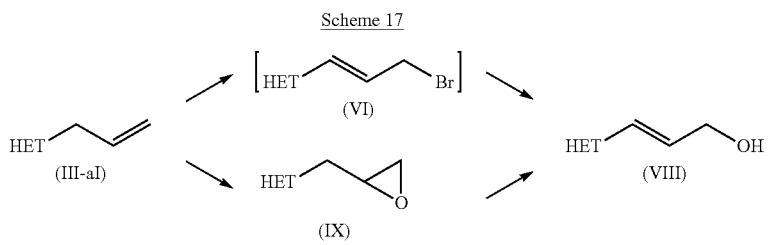

The conversion from the heterocyclic allyl derivate (III-al) to the alcohol (VIII) is either way a simple and short process in view of the preparation of the aldehyde (II). The synthetic route via an intermediate (VI) to the alcohol (VIII) is similarly performed to the conversion of the heterocyclic methyl derivative (III-Me) to the alcohol (V) in a convenient, economically and ecologically desirable one pot reaction. The conversion via the epoxide (IX) is a high yielding process comparably desirable to the process described above through the use of a phase transfer catalyst.

(22) The process according to any one of items 1 and 3 to 7, wherein for the preparation of the aldehyde (II) the conversion of the heterocyclic allyl derivative (III-al) proceeds in a one pot reaction

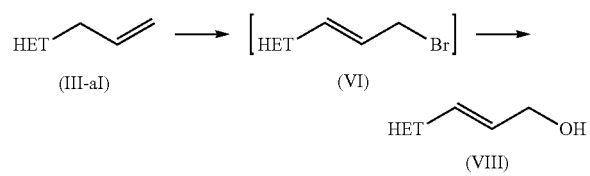

wherein HET is defined as herein.

The heterocyclic allyl derivative (III-al) can be converted to the alcohol (VIII) without prior isolation of the intermediate bromide (VI). Further, the bromination reaction is suitably carried out as a radical bromination using preferably mild N-bromoamide as brominating agent under ultra violet radiation. This is advantageous over bromination reactions using phosphorous tribromide or hydrobromic acid as brominating agents since these brominating agents are either toxic (PBr$_3$) or corrosive and aggressive (HBr) and in this relation difficult to handle. Therefore no special reaction conditions are necessary in order to deal with these problematic properties. Further, conversion of compound (VI) to (VIII) is accomplished under mild reaction conditions and by means of very cheap and ecologically friendly chemicals. Thus in both steps of the one pot reaction cheap chemicals and mild conditions are applied. In particular, the N-bromoamide as a brominating agent N-bromoamide is selected from the group consisting of N-bromoacetamide, N,N-dibromobenzene sulfonamides, N-bromosuccinimide, N-bromophthalimide, N-bromoglutarimide, 3-bromo-hydantoin and 1,3-dibromo-5,5-dimethyl-hydantoin, preferably it is N-bromosuccinimide. In a preferred embodiment of the invention the bromination reaction is performed without the use of a radical former. For the aqueous nucleophilic substitution converting the bromide (VI) to the alcohol (VIII) cheap bases can be used selected from the group consisting of inorganic basic salts comprising carbonates, hydrides and hydroxides, preferably from preferably potassium and sodium carbonates, most preferably it is sodium bicarbonate.

(23) The process according to any one of items 1 and 3 to 7, wherein for the preparation of the aldehyde (II) compound (III-al) is converted via the intermediate (IX)

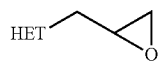
(IX)

to the heterocyclic alcohol (VIII)

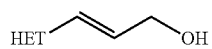
(VIII)

wherein HET is defined as herein.

The process described herein proceeds in two separated reaction steps. The first reaction comprises an epoxidation reaction of the heterocyclic allyl derivative (III-al) to the epoxide (IX). Suitable epoxidation agents are for example dimethyldioxirane, either readily prepared or in situ generated by reacting potassium peroxymonosulfate (KHSO$_5$.KHSO$_4$.K$_2$SO$_4$, oxone) with acetone preferably in the presence of phase transfer catalyst. Another type of agents that can be used for the said transformation consists of peroxide in the presence of metal containing catalysts. In particular when metals applied consists of vanadium and titanium. A process having a step with the use of a phase transfer catalyst being incorporated is in general economically and ecologically interesting and a contribution to green chemistry. Further the conversion is performed in the presence of a cheap base selected from the group consisting of inorganic basic salts comprising carbonates, hydrides and hydroxides, preferably potassium and sodium carbonates, most preferably sodium bicarbonate. The phase transfer catalyst is selected from the group consisting of N-methyl-N,N,N-trioctylammonium chloride, benzyltrimethylammonium chloride, tetrabutylammonium chloride and hexadecyltributylphosphonium bromide.

The second reaction comprises the conversion of the epoxide (IX) to the alcohol (VIII) in the presence of a base or an acid. A suitable base used for the conversion is selected from the group consisting of organic bases such as amides, amidines, tertiary amines including pyridine, triethylamine, 1,4-diazabicyclo[2.2.2]octane (DABCO), most preferably 1,4-diazabicyclo[2.2.2]octane (DABCO). A suitable acid is selected from the group consisting of organic or inorganic acids such as hydrochloric acid, sulfuric acid, nitric acid, phosphorous acid, acetic acid, hydrobromic acid, triflic acid, trifluoroacetic acid, methanesulfonic acid, para tuluenesulfonic acid and the like.

(24) The process according to any one of items 1 and 3 to 7, wherein for the preparation of the aldehyde (II) compound (VIII)

(VIII)

is converted to the heterocyclic aldehyde (II)

(II)

by an oxidation reaction
wherein HET is defined as herein.

The oxidation can be carried out in the presence of prevalent oxidizing agents in organic chemistry comprising but not being limited to 4-methylmorpholine-N-oxide in the presence of catalytic amounts of tetrapropylammonium perruthenate (TPAP), pyridinium chlorochromate (PCC), pyridinium dichromate (PDC), hydrogen peroxide, 2,2,6,6-tetramethylpiperidine-1-oxyl (TEMPO) in the presence of trichloroisocyanuric acid (TCICA), dimethyl sulfoxide with acetanhydride and dimethyl sulfoxide with oxalyl chloride (Swern oxidation method), preferably 2,2,6,6-tetramethylpiperidine-1-oxyl (TEMPO) in the presence of trichloroisocyanuric acid (TCICA), and dimethyl sulfoxide with acetanhydride.

(25) The process according to any one of items 1 to 7, wherein aldehyde (I) is converted to aldehyde (II)

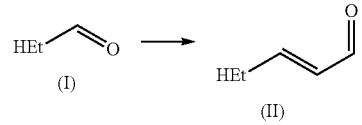

wherein HET is defined as herein.

The optional conversion of the aldehyde (I) to the aldehyde (II) comprises various reaction pathways and intermediate compounds.

In preferred embodiment of the present invention the aldehyde (I) is converted to the aldehyde (II) via an intermediate (X)

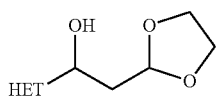

and subsequently via the intermediate (XI)

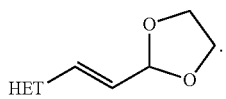

The conversion of the aldehyde (I) to intermediate (X) is preferably performed by reaction with a dioxolanymethyl nucleophile. A suitable dioxolanymethyl nucleophile is a dioxolanymethyl Grignard reagent thus a dioxolanymethyl magnesium halide, preferably a chloride, bromide or iodide. Preferably the intermediate (X) is isolated before being further reacted to the intermediate (XI). The conversion of the intermediate (X) to the intermediate (XI) is preferably performed by dehydration in the presence of an acid. Preferably the intermediate (XI) is isolated before being further reacted to the aldehyde (II).

The second step of the reaction sequence comprises converting the intermediate (XI) to the aldehyde (II) by deprotection of the dioxolanyl group.

Preferably the deprotection is performed in the presence of aqueous acid.

In another preferred embodiment of the present invention the aldehyde (I) is converted to the aldehyde (II) via an intermediate (XI)

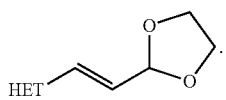

The first step of the conversion comprises the formation of the intermediate (XI) by a Wittig type reaction of the aldehyde (I) with dioxolanylmethylenetriphenylphosphane in the presence of a base. The Wittig type reaction is performed in an organic solvent selected from the group consisting of acetone, ethyl acetate, hydrocarbons, aromatic hydrocarbons, ethers, esters, chlorinated hydrocarbons and acetonitrile or a mixture thereof and the intermediate (XI) is preferably isolated.

The second step of the reaction sequence comprising conversion to the aldehyde (II) is performed as described before in this item.

Yet in another preferred embodiment of the present invention the aldehyde (I) is directly converted in a single reaction step to the aldehyde (II). In this preferred embodiment the aldehyde (I) is converted to the heterocyclic aldehyde (II) by reaction with ethylpyruvate in the presence of pyruvate decarboxylase. Further the aldehyde (I) is also directly converted to aldehyde (II) by reaction with acetaldehyde. Preferably the acetaldehyde is provided from the reaction described under item 20. Optionally this reaction is performed in a pressurizable reaction vessel, preferably in an autoclave. In another preferred embodiment the aldehyde (I), if optionally prepared by ozonolysis as described under item 20, is converted to (II) in a one pot reaction by reacting (I) with acetaldehyde evolved as a side product from the ozonolysis.

The various embodiments of item 25 can be summarized by the following Scheme 18:

Scheme 18

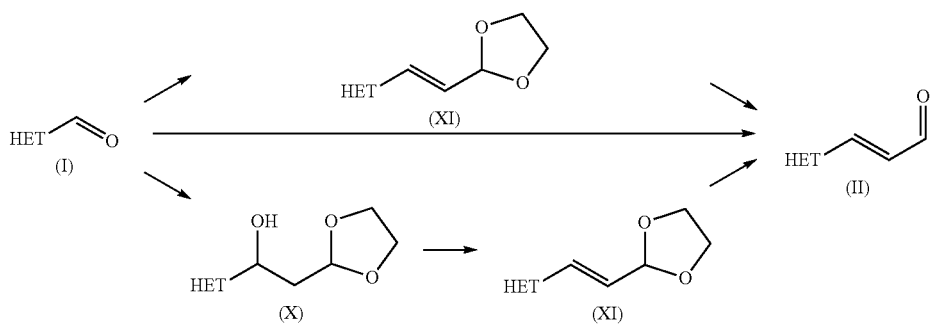

(26) A compound defined by the following formula (XIVa):

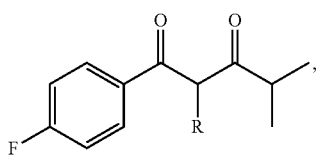

wherein R is a straight or branched, saturated or unsaturated, optionally substituted alkyl moiety, preferably a straight alkyl moiety, more preferably a methyl or an allyl group.

(27) A compound defined by formula (XVIIIa), wherein in the compound of formula (XVIIIa) R" is a substituent selected from the group consisting of allyl, prop-1-enyl, oxiran-2-ylmethyl, 3-bromoprop-1-enyl, 2-dioxolanylethenyl and 2-dioxolanyl-1-hydroxyethyl substituents.

(XVIIIa)

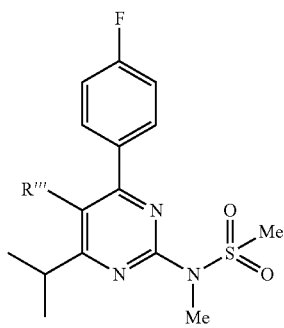

(28) A compound defined by formula (XIXb), wherein R'''' is a substituent selected from the group consisting of methyl, allyl, prop-1-enyl, 3-bromopro-1-enyl, oxiran-2-ylmethyl, 3-hydroxyprop-1-enyl and 2-dioxolanyl-1-hydroxyethyl substituents.

(XIXb)

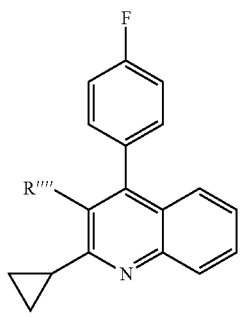

(29) 1-(4-Fluorophenyl)-2,4-dimethylpentane-1,3-dione (XIV-Me-a):

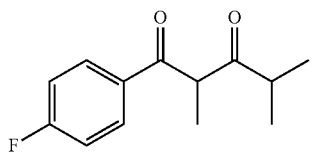 [SMILES: CC(C)C(=O)C(C)C(=O)c1ccc(F)cc1]

(30) 2-Allyl-1-(4-fluorophenyl)-4-methylpentane-1,3-dione (XIV-al-a):

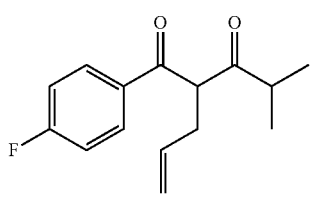 [SMILES: C=CCC(C(=O)c1ccc(F)cc1)C(=O)C(C)C]

(31) 5-Allyl-4-(4-fluorophenyl)-6-isopropyl-N-methylpyrimidin-2-amine (XV-al-a):

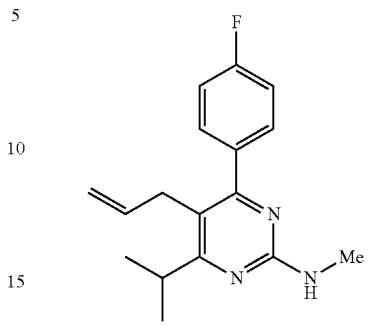

(32) N-(5-Allyl-4-(4-fluorophenyl)-6-isopropylpyrimidin-2-yl)-N-methylmethanesulfonamide (III-al-a):

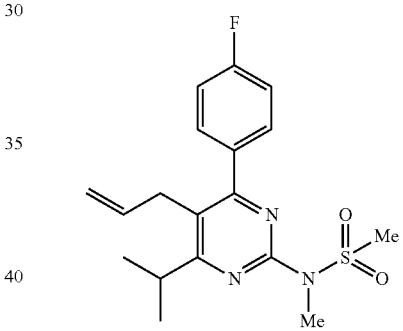

(33) N-(4-(4-Fluorophenyl)-6-isopropyl-5-(prop-1-enyl)pyrimidin-2-yl)-N-methylmethanesulfonamide (VIIa):

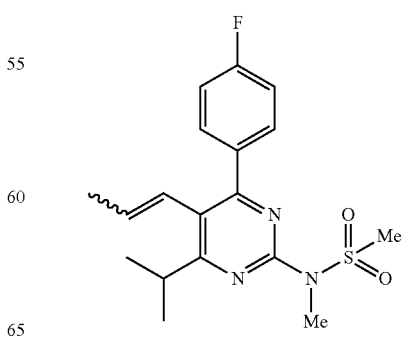

(34) N-(4-(4-Fluorophenyl)-6-isopropyl-5-(oxiran-2-ylmethyl)pyrimidin-2-yl)-N-methylmethanesulfonamide (IXa):

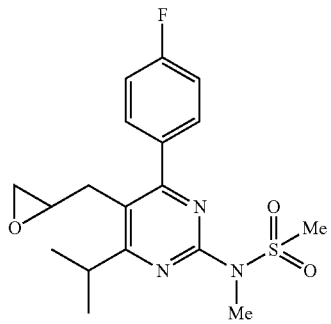 [SMILES: CC(C)c1nc(N(C)S(C)(=O)=O)nc(-c2ccc(F)cc2)c1CC1CO1]

(35) (E)-N-(4-(4-Fluorophenyl)-5-(3-bromoprop-1-enyl)-6-isopropylpyrimidin-2-yl)-N-methylmethanesulfonamide (VIa):

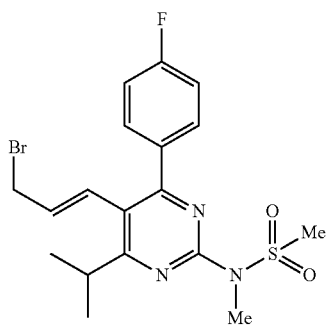 [SMILES: CC(C)c1nc(N(C)S(C)(=O)=O)nc(-c2ccc(F)cc2)c1/C=C/CBr]

(36) N-(4-(4-Fluorophenyl)-6-isopropyl-5-(dioxolanymethylethenyl)pyrimidin-2-yl)-N-methylmethanesulfonamide (XIa):

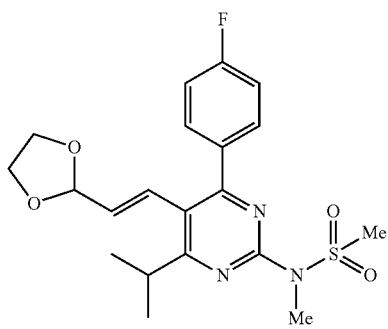 [SMILES: CC(C)c1nc(N(C)S(C)(=O)=O)nc(-c2ccc(F)cc2)c1/C=C/C1OCCO1]

(37) N-(4-(4-Fluorophenyl)-6-isopropyl-5-(2-dioxolanymethyl-1-hydroxyethyl)pyrimidin-2-yl)-N-methylmethanesulfonamide (Xa):

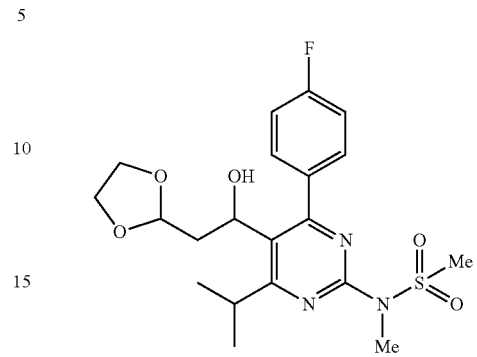

(38) 2-Cyclopropyl-4-(4-fluorophenyl)-3-methylquinoline (III-Me-b):

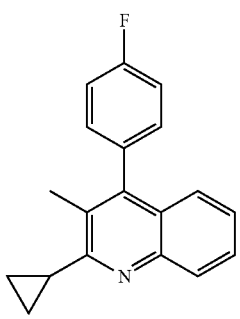 [SMILES: Cc1c(C2CC2)nc2ccccc2c1-c1ccc(F)cc1]

(39) 3-Allyl-2-cyclopropyl-4-(4-fluorophenyl)quinoline (III-al-b):

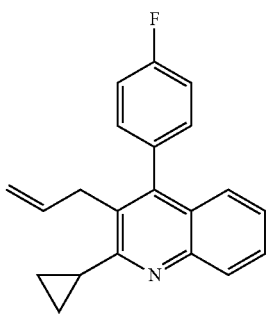 [SMILES: C=CCc1c(C2CC2)nc2ccccc2c1-c1ccc(F)cc1]

(40) 2-Cyclopropyl-4-(4-fluorophenyl)-3-prop-1-enylquinoline (VIIb):

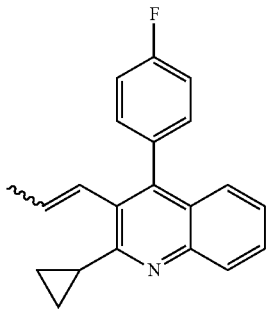

(41) 3-(Bromoprop-1-enyl)-2-cyclopropyl-4-(4-fluorophenyl)quinoline (VIb):

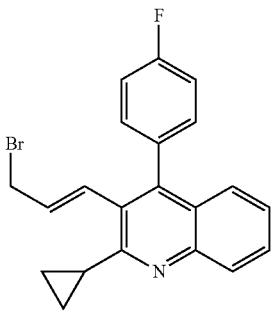

(42) 2-Cyclopropyl-4-(4-fluorophenyl)-3-(oxiran-2-ylmethyl)quinoline (IXb):

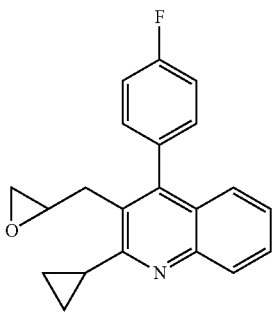 [SMILES: Fc1ccc(-c2c(CC3CO3)c(C3CC3)nc3ccccc23)cc1]

(43) 2-Cyclopropyl-4-(4-fluorophenyl)-3-(3-hydroxyprop-1-enyl)quinoline (VIIIb):

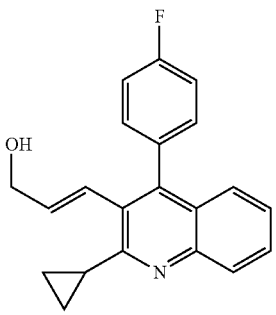 [SMILES: OC/C=C/c1c(C2CC2)nc2ccccc2c1-c1ccc(F)cc1]

(44) 2-Cyclopropyl-3-(2-dioxolanymethyl-1-hydroxyethyl)-4-(4-fluorophenyl)quinoline (Xb)

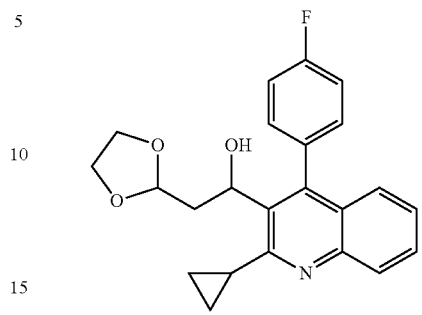

(45) The use of a compound as defined in any one of items 27 to 30 for the synthesis of HMG-CoA reductase inhibitors commonly referred to as "statins".

(46) The use of a compound as defined in any one of items 31 to 37 for the synthesis of Rosuvastatin.

(47) The use of a compound as defined in any one of items 38 to 44 for the synthesis of Pitavastatin.

(48) A process for the preparation of Rosuvastatin or pharmaceutically acceptable salt of Rosuvastatin, comprising the steps of:
 a) carrying out a process for preparing the compound of formula (Ia) according to any one of items 1 to 4, and
 b) subjecting the compound of formula (Ia) to further synthesis steps to yield Rosuvastatin or pharmaceutically acceptable salts thereof.

(49) A process for the preparation of Rosuvastatin or pharmaceutically acceptable salt of Rosuvastatin, comprising the steps of:
 a) carrying out a process for preparing the compound of formula (IIa) according to any one of items 1, 3 and 4, and
 b) subjecting the compound of formula (IIa) to further synthesis steps to yield Rosuvastatin or pharmaceutically acceptable salts thereof.

(50) A process for the preparation of a pharmaceutical composition comprising Rosuvastatin as active ingredient, comprising the steps of:
 a) preparing Rosuvastatin or pharmaceutically acceptable salts thereof according to the process according to item 48 or 49, and
 b) admixing the thus prepared Rosuvastatin or pharmaceutically acceptable salt thereof with at least one pharmaceutically acceptable excipient.

(51) A process for the preparation of Pitavastatin or pharmaceutically acceptable salt of Pitavastatin, comprising the steps of:
 a) carrying out a process for preparing the compound of formula (Ib) according to any one of items 1, 2, 3 and 5, and
 b) subjecting the compound of formula (Ib) to further synthesis steps to yield Pitavastatin or pharmaceutically acceptable salts thereof.

(52) A process for the preparation of Pitavastatin or pharmaceutically acceptable salt of Pitavastatin, comprising the steps of:
 a) carrying out a process for preparing the compound of formula (IIb) according to any one of items 1, 3 and 5, and b) subjecting the compound of formula (IIb) to further synthesis steps to yield Pitavastatin or pharmaceutically acceptable salts thereof.
(53) A process for the preparation of a pharmaceutical composition comprising Pitavastatin as active ingredient, comprising the steps of:
a) preparing Pitavastatin or pharmaceutically acceptable salts thereof according to the process according to item 51 or 52, and
b) admixing the thus prepared Pitavastatin or pharmaceutically acceptable salt thereof with at least one pharmaceutically acceptable excipient.

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

The present invention provides an industrially applicable, economical and simple process for the preparation of key intermediates of statins and particularly of Rosuvastatin and Pitavastatin, two members of the medication class of statins which are competitive inhibitors of the enzyme HMG-CoA reductase, the enzyme that catalyses the first step of cholesterol synthesis. For statins and particularly for the aforementioned Rosuvastatin and Pitavastatin, the synthetic route introduced herein benefits from simple reactions, mild reaction conditions and readily available and cheap chemicals.

The respective starting materials for the syntheses are readily available or easy to synthesize. The starting compound for Rosuvastatin, diketone (XIIIa), is most commonly synthesized by reaction of 4-fluorophenylmethylketone and ethyl 2-methylpropylate. Further, starting compounds for Pitavastatin are simple cyclopropyl carbonyl derivatives of which a wide range of compounds can be used. These cyclopropyl carbonyl derivatives can generally be prepared from cyclopropionic acid and the most suitable congeners can further be used for the synthesis of Pitavastatin. The possibility of selecting the right starting material provides the opportunity of optimization of the whole process because the limitation of only a single reaction pathway due to only one starting compound is not given.

Starting from these materials the present invention provides several synthetic routes to key intermediates of statins, preferably of Rosuvastatin and Pitavastatin. These synthetic routes feature the exclusion of using tedious and reactive DIBAL-H, which requires special reaction conditions and which is expensive. Further the corresponding key intermediates can be prepared via short and simple reaction sequences comprising a 3 step synthesis of the heterocyclic compound (IIIa) starting from the diketone (XIIIa). An economically and ecologically desirable process is provided wherein the aldehydes (Ia) and (IIa) are prepared in 5 reaction steps starting from the diketone (XIIIa) having a one pot reaction incorporated converting compounds of the formula (IIIa) to the compounds (Va) and (VIIIa) respectively. Yet another process is provided wherein the aldehyde (Ia) is prepared from the diketone (XIIIa) incorporating a high yield isomerization of compound of the formula (IIIa) to compound of the formula (VIIa). Similar short and efficient synthetic routes are achievable for the preparation of key intermediates for Pitavastatin starting from derivatives of cyclopropanecarboxylic acid (XVIb). The aldehydes (Ib) and (IIb) can be prepared according to the present invention in 5 reaction steps without the use of DIBAL-H and under exclusion of special reaction conditions.

Furthermore the present invention offers an optional synthetic path for converting the aldehyde (I) to the aldehyde (II). This optional conversion can be performed in different variations providing the possibility of process optimization for each particular substrate. The conversion from aldehyde (I) to the aldehyde (II) can be performed comprising either a Wittig type reaction with or without aqueous work up or a short and simple one step reaction with acetaldehyde or pyruvate decarboxylase.

The term "heterocycle" as used herein includes, if not stated otherwise with respect to particular embodiments, a saturated (e.g. heterocycloalkyl) or unsaturated (e.g. heteroaryl) heterocyclic ring moiety having 3, 4, 5, 6, 7, 8, 9, 10, 11, 12, 13, 14, 15 or 16 ring atoms, at least one of which is selected from nitrogen and oxygen. In particular, heterocyclyl includes a 3- to 10-membered ring or ring system and more particularly a 6- or 10-membered ring, which may be saturated or unsaturated; examples thereof include oxiranyl, aziridinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, ehromenyl, isochromanyl, chromanyl and the like.

More specifically, a unsaturated heterocyclic moiety may have 5, 6, 7, 8, 9 or 10 ring carbon atoms and 1, 2, or 3 ring heteroatoms selected from nitrogen and oxygen. The group may be a polycyclic ring system but often is monocyclic, for example including azetidinyl, pyrrolidinyl, tetrahydrofuranyl, piperidinyl, oxiranyl, pyrazolidinyl, pyrimidinyl, imidazolyl, indolizidinyl, piperazinyl, thiazolidinyl, morpholinyl, thiomorpholinyl, quinolyl and the like.

The term "substituted" as used herein in reference to a structure/moiety/group means that one or more, especially up to 5, more especially 1, 2 or 3, of the hydrogen atoms in said structure/moiety/group are replaced independently of each other by the corresponding number of substituents known to a person skilled in the art. Typical substituents include, without being limited to halogen, fluorophenyl, cyano, nitro, oxo, $NR^1$, —$OR^1$, —$C(O)R^1$, —$C(O)OR^1$, —$OC(O)R^1$, —$S(O)R^1$, $N(R^1)R^2$, $C(O)N(R^1)R^2$, —$N(R^1)SO_2R^1$ and $R^3$, wherein each of $R^1$, $R^2$ and $R^3$ are selected from the group consisting of $C_1$-$C_6$ alkyl, $C_1$-$C_6$ alkoxy, —$(CH_2)_m$-heterocyclyl (m being 1, 2, 4 or 4) and each $R^1$ and $R^2$ may be optionally and independently further substituted with one or more of hydrogen, halogen, cyano, amino, hydroxy, —$C_6$ alkyl and $C_1$-$C_6$ alkoxy. Specific substituents in particular include halogen such as fluoro, chloro and/or bromo, hydroxy, amino, $C_1$-$C_6$ alkyl, cyclic $C_1$-$C_6$ alkyl and $C_1$-$C_6$ alkoxy, and branched $C_1$-$C_6$ alkyl and halogenated aryls such as fluorophenyl. It will be understood that substituents are at positions where they are chemically possible, it being known or evident to the person skilled in the art to decide (either experimentally or theoretically) without inappropriate effort whether a particular substitution is possible. For example, substituents which may be unstable or may affect reactions disclosed herein may be omitted, at least at the relevant stage of intermediate compound or of the affected reaction.

The term "phase transfer catalysts" used herein according to preferred embodiments can be any known phase transfer catalysts typically used in organic synthesis. The phase transfer catalysts can include, without being limited to, (2-methoxyethoxymethyl)triethylammonium halide, (3-crylamidopropyl)trimethylammonium halide, (3-chloro-2-hydroxypropyl)trimethylammonium halide, 1-butyl-1-methylpyrrolidinium halide, acetylcholine halide, benzalkonium halide, benzethonium halide, benzoylcholine halide, benzylcetyldimethylammonium halide hydrate, benzyldimethylphenylammonium halide, benzyldimethylstearylammonium halide hydrate, benzyldimethyltetradecylammonium halide hydrate, benzyltributylammonium halide, benzyltriethylammonium halide, benzyltrimethylammonium halide, beta-methylcholine halide, carbamylcholine halide, chlorocholine halide, choline halide, decyltrimethylammonium halide, diallyldimethylammonium halide, dimethyldistearylammonium halide, DL-carnitine hydrohalide, dodecyltrimethylammonium halide, Girard's Reagent T, hexadecyltrimethyl-ammonium halide, hexadecyltributylphosphonium halide, hexamethonium halide dihydrate, lauroylcholine halide, methacholine halide, methacroylcholine halide, N-methyl-N,N,N-trioctylammonium halide, N-benzylcinchonidinium halide, N-benzylcinchoninium halide, N-benzylquinidinium halide, N-benzyl-quininium halide, n-octyltrimethylammonium halide, phenyltriethylammonium halide, phosphocholine halide calcium salt tetrahydrate, phosphocholine halide sodium salt hydrate, stachydrine hydrohalide, succinylcholine halide, tetraamylammonium halide, tetrabutylammonium halide, tetraethylammonium halide, tetramethylammonium halide, tetrapropylammonium halide, triethylmethylammonium halide, trimethylphenylammonium halide, trimethylstearylammonium halide, trimethyltetradecylammonium halide, trimethyl[2,3-(dioleyloxy)propyl]ammonium halide, trimethyl[3-(triethoxysilyl)propyl]ammonium halide and the like.

According to a preferred option (A) of an embodiment of the present invention the synthesis of heterocyclic aldehyde of formula (Ia) as a key intermediate for Rosuvastatin

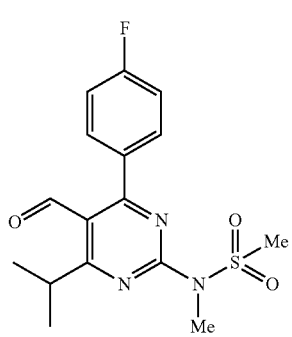

(Ia)

comprises
a. methylating 1-(4-fluorophenyl)-4-methylpentane-1,3-dione (XIIIa) with a electrophilic methyl source which is selected from the group consisting of iodomethane, dimethyl sulfate, dimethyl carbonate, trimethyl phosphate, methyl triflate, methyl tosylate, methyl benzenesulfonate, methyl ethanesulfonate, methyl methanesulfonate, and methyl fluorosulfonate, preferably iodomethane in the presence of a base in a common organic solvent such as acetone, ethyl acetate, hydrocarbons, aromatic hydrocarbons or acetonitrile or mixtures thereof, preferably acetone at preferably ambient temperatures for 1 hour up to 2 days. The base is added to the reaction mixture for deprotonation of the methylene group located between the two carbonyl groups facilitating an electrophilic attack at this particular position. Suitable bases are selected from organic and inorganic bases. Preferably the base is selected from the group consisting of inorganic basic salts comprising carbonates, hydrides and hydroxides. Most preferably the base is selected from the group consisting of carbonates comprising alkaline, alkaline earth and earth metal carbonates and in particular it is potassium carbonate. The amount of base is preferably about 1 to about 1.5 times the molar stoichiometric amount based on compound of the formula (XIIIa). The reaction further can be carried out at a temperature between 0 to 56° C., preferably it is between 19 to 25° C. and is performed for between 1 to 48 hours, for example for about 24 hours.

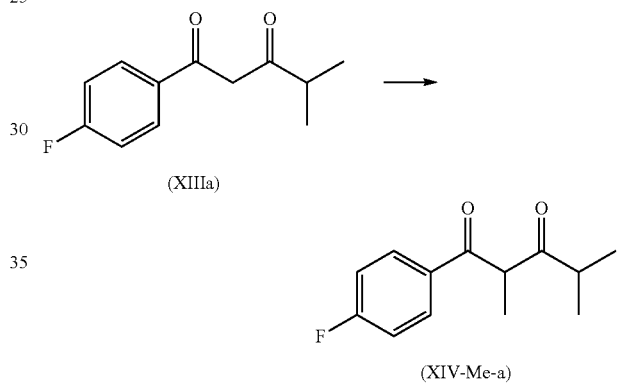

b. converting compound (XIV-Me-a) in a cyclization reaction with N-methyl guanidine hydrochloride to heterocycle (XV-Me-a) in the presence of a base selected from the group consisting of hydrides, comprising alkaline, alkaline earth and earth metal hydrides, preferably sodium hydride, and carbonates, comprising alkaline, alkaline earth and earth metal carbonates, preferably cesium carbonate, in an organic solvent selected from the group consisting of acetone, ethyl acetate, hydrocarbons, aromatic hydrocarbons, ethers, esters, chlorinated hydrocarbons and acetonitrile or a mixture thereof, preferably THF or MeTHF at preferably 40° C. for 10 minutes up to 48 hours. The base is from about 0.5 to about 2 times the molar stoichiometric amount based on compound of the formula (XIV-Me-a), preferably about 1 to about 1.5 times, and in particular it is equimolar and it is added slowly in several portions.

Preferably the amount of the N-methyl guanidine hydrochloride is from about 1 to 3 times the molar stoichiometric amount based on compound of the formula (XIV-Me-a), most preferably it is equimolar. Further the cyclization reaction is carried out for about 10 minutes to 48 hours, preferably for 8 hours and at a temperature between 15 to 66° C., preferably at 40° C. After completion of the cyclization reaction water is added to the reaction mixture.

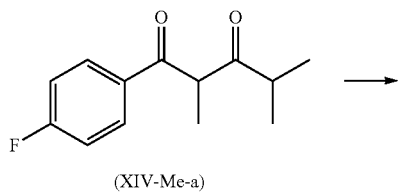

(XIV-Me-a)

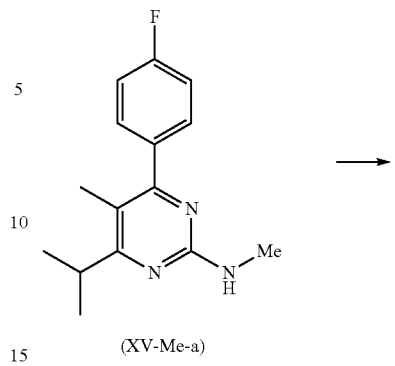

(XV-Me-a)

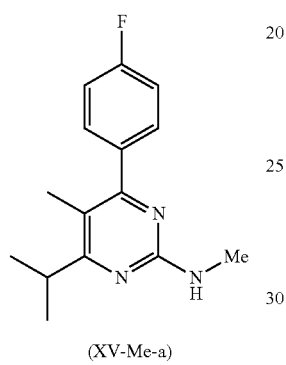

(XV-Me-a)

c. sulfonating the amino group in (XV-Me-a) to compound (III-Me-a) with a methylsulfonization source, in the presence of a base selected from the group consisting of organic bases such as amides, amidines, tertiary amines including pyridine, triethylamine, preferably triethylamine, which is added in an initial amount from about 1 to about 6 times the molar stoichiometric amount based on compound of the formula (XV-Me-a), preferably it is about 1.2 times, in a solvent selected from the group consisting of acetone, ethyl acetate, hydrocarbons, aromatic hydrocarbons, ethers, esters, chlorinated hydrocarbons and acetonitrile or a mixture thereof, preferably in dichloromethane.

Preferably the electrophilic methanesulfonyl source is methanesulfonyl chloride and it is added to the reaction mixture in an initial amount from about 1 to about 3 times the molar stoichiometric amount based on compound of the formula (XV-Me-a), more preferably about 2 times.

The reaction mixture is cooled below room temperature and the methanesulfonyl source is added at decreased temperatures below room temperature, preferably between −20° C. and 10° C., more preferably at 0° C. In another preferred embodiment the methanesulfonyl source is added very slowly to the reaction mixture and during the slow addition the temperature in the reaction vessel is kept at the preferred temperature below room temperature. After the addition the sulfonization reaction is performed for 1 to 48 hours, preferably for about 24 hours at preferably ambient temperatures.

(III-Me-a)

d. brominating (III-Me-a) at the aryl methyl group preferably in a radical bromination reaction with a brominating agent preferably N-bromosuccinimide, in an organic solvent selected from the group consisting of acetone, ethyl acetate, hydrocarbons, aromatic hydrocarbons, ethers, esters, chlorinated hydrocarbons and acetonitrile or a mixture thereof, preferably in acetonitrile, under treatment of visible or ultraviolet radiation of 200-400 nm in batch or flow mode at ambient temperatures for 2 to 10 hours,

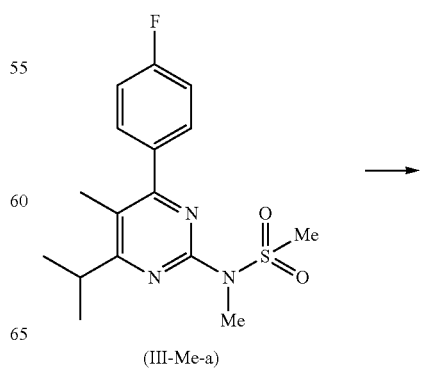

(III-Me-a)

-continued

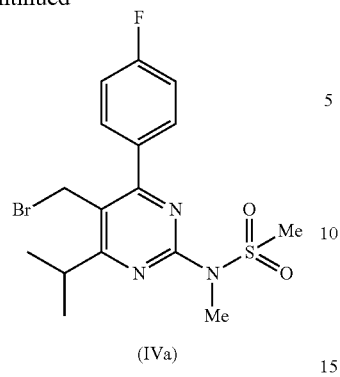

(IVa)

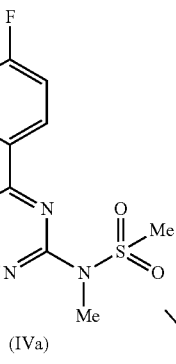

(IVa)

e. converting (IVa) without being isolated to alcohol (Va) by nucleophilic substitution in the presence of a base selected from the group consisting of carbonates comprising alkaline, alkaline earth and earth metal carbonates, preferably potassium and sodium carbonates, most preferably sodium bicarbonate in aqueous form at a temperature between ambient temperature and reflux conditions for 10 minutes up to 24 hours

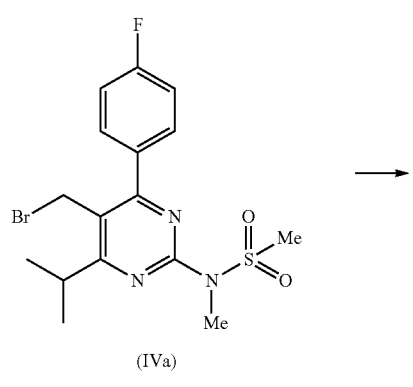

(IVa)

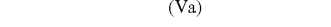

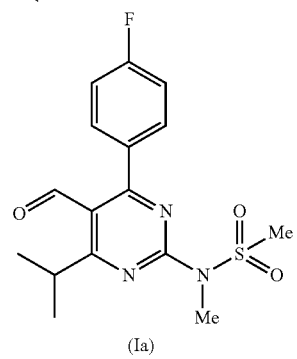

(Ia)

(Va)

According to a preferred option (B) of an embodiment of the present invention the synthesis of heterocyclic aldehyde of formula (Ia) as a key intermediate for Rosuvastatin

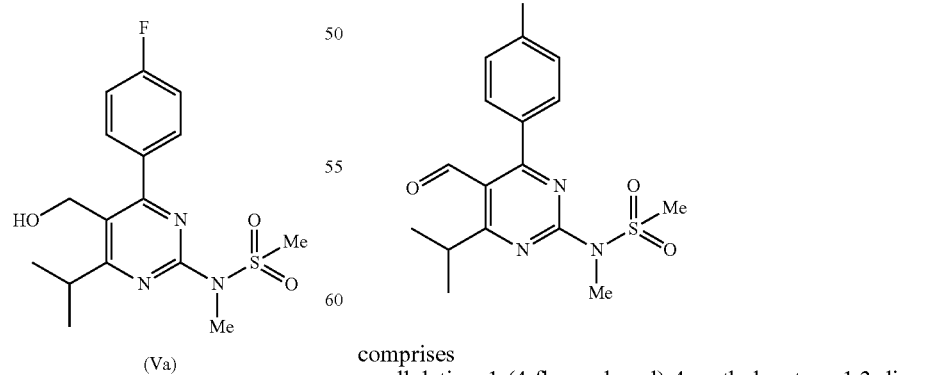

(Va)

f. oxidizing (IVa) or (Va) to heterocyclic aldehyde (Ia) in the presence of an oxidizing agent selected from oxidizing agents in organic chemistry comprises
g. allylating 1-(4-fluorophenyl)-4-methylpentane-1,3-dione (XIIIa) to (XIV-al-a) with a electrophilic allyl source which is selected from the group consisting of allyl halides, preferably allyl bromide in the presence of a base in an organic solvent such as acetone, ethyl acetate, hydrocarbons, aromatic hydrocarbons or acetonitrile or mixtures thereof, preferably acetone at preferably ambient temperatures for 1 hour up to 2 days.

The base is added to the reaction mixture for deprotonation of the methylene group located between the two carbonyl groups facilitating an electrophilic attack at this particular position. Suitable bases are selected from organic and inorganic bases. Preferably the base is selected from the group consisting of inorganic basic salts comprising carbonates, hydrides and hydroxides. Most preferably the base is selected from the group consisting of carbonates comprising alkaline, alkaline earth and earth metal carbonates and in particular it is potassium carbonate. The amount of base is preferably about 1 to about 1.5 times the molar stoichiometric amount based on compound of the formula (XIIIa). The reaction further can be carried out at a temperature between 0 to 56° C., preferably it is between 19 to 25° C. and is performed for between 1 to 48 hours, for example for about 4 hours.

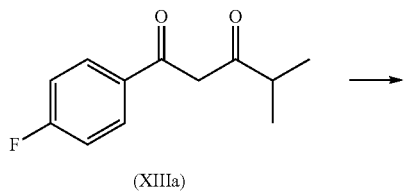

(XIIIa)

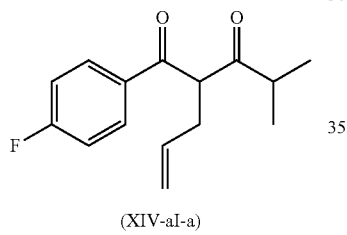

(XIV-aI-a)

h. converting compound (XIV-al-a) in a cyclization reaction with N-methyl guanidine hydrochloride to heterocycle (XV-al-a) in the presence of a base selected from the group consisting of hydrides comprising alkaline, alkaline earth and earth metal hydrides, preferably sodium hydride, and carbonates, comprising alkaline, alkaline earth and earth metal carbonates, preferably cesium carbonate, in an organic solvent selected from the group consisting of acetone, ethyl acetate, hydrocarbons, aromatic hydrocarbons, ethers, esters, chlorinated hydrocarbons and acetonitrile or a mixture thereof, preferably THF or MeTHF at preferably 40° C. for 10 minutes up to 48 hours. The base is from about 0.5 to about 2 times the molar stoichiometric amount based on compound of the formula (XIV-al-a), preferably about 1 to about 1.5 times, for example, equimolar and it is added slowly in several portions.

Preferably the amount of the N-methyl guanidine hydrochloride is from about 1 to 3 times the molarstoichiometric amount based on compound of the formula (XIV-al-a), most preferably it is equimolar. Further the cyclization reaction is carried out for about 10 minutes to 48 hours, preferably for 1 hour and at a temperature between 15 to 66° C., preferably at 40° C. After completion of the cyclization reaction water is added to the reaction mixture.

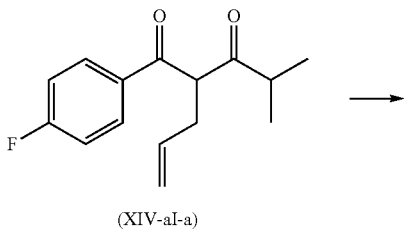

(XIV-aI-a)

(XV-aI-a)

i. sulfonating the amino group in (XV-al-a) to compound (III-al-a) with a methylsulfonization source, in the presence of an organic base, in a solvent selected from the group consisting of acetone, ethyl acetate, hydrocarbons, aromatic hydrocarbons, ethers, esters, chlorinated hydrocarbons and acetonitrile or a mixture thereof, preferably in dichloromethane, at decreased temperatures of about −20 to 10° C., for 1 hour up to two days.

In a preferred embodiment of the present invention the base used for the sulfonization reaction is selected from the group consisting of organic bases such as amides, amidines, tertiary amines including pyridine, triethylamine, preferably it is triethylamine, which is added in an initial amount from about 1 to about 6 times the molar stoichiometric amount based on compound of the formula (XV-al-a), preferably it is about 4 times.

Preferably the electrophilic methanesulfonyl source is methanesulfonyl chloride and it is added to the reaction mixture in an initial amount from about 1 to about 3 times the molar stoichiometric amount based on compound of the formula (XV-al-a), more preferably about 2.5 times.

The reaction mixture is cooled below room temperature and the methanesulfonyl source is added at decreased temperatures below room temperature, preferably between −20° C. and 10° C., more preferably at −5° C. In another preferred embodiment the methanesulfonyl source is added very slowly to the reaction mixture and during the slow addition the temperature in the reaction vessel is kept at the preferred temperature below room temperature. After the addition the sulfonization reaction is performed for 1 to 48 hours, preferably for about 10 hours. In a preferred embodiment of the present invention the temperature of the reaction mixture is kept at the preferred temperature below room temperature.

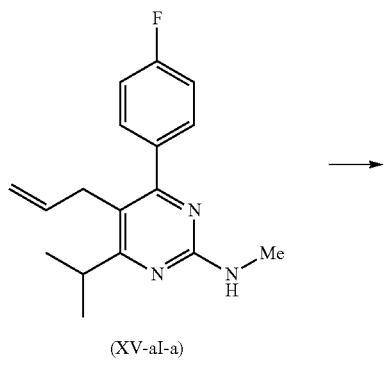

(XV-aI-a)

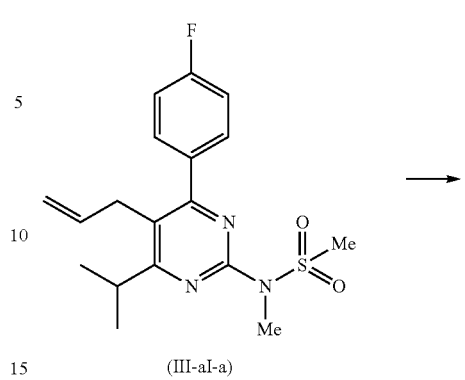

(III-aI-a)

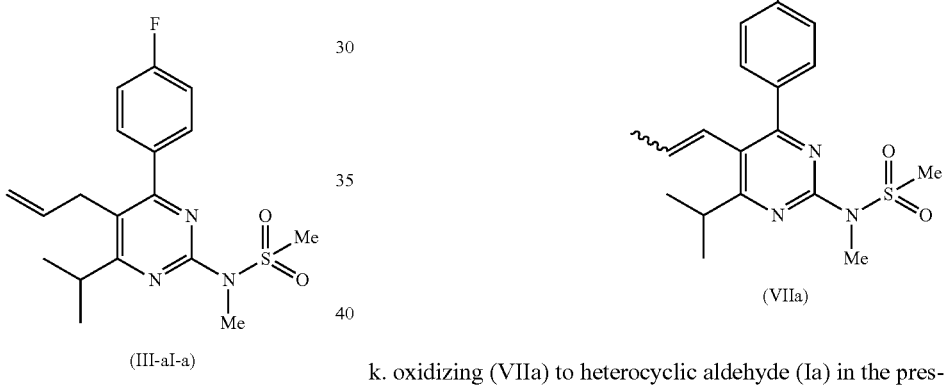

(III-aI-a)     (VIIa)

j. converting (III-al-a) by isomerization to compound (VIIa) in the presence of a base selected from the group consisting of hydroxides comprising alkaline, alkaline earth and earth metal hydroxides, preferably potassium in a solvent selected from the group consisting of acetone, ethyl acetate, hydrocarbons, aromatic hydrocarbons and acetonitrile or a mixture thereof, preferably toluene in the presence of water and a phase transfer catalyst selected from the group consisting of N-methyl-N,N,N-trioctylammonium chloride, benzyltrimethylammonium chloride and hexadecyltributylphosphonium bromide, preferably N-methyl-N,N,N-trioctylammonium chloride at a temperature between 0 and 90° C. for 1 hour up to 2 days.

The phase transfer catalyst is used with an initial amount from about 0.001 to about 1 times the molar stoichiometric amount based on compound (III-al-a), preferably about 0.005 to 0.5 times, more preferably about 0.01 to 0.2 times and in particular it is 0.02 times. The base is applied only in catalytic amount from about 0.05 to about 0.5 times the molar stoichiometric amount based on compound (III-al-a), preferably about 0.2 times. Furthermore, the isomerization is carried out at a temperature between 0 to 90° C., more preferably between 19 to 25° C.

k. oxidizing (VIIa) to heterocyclic aldehyde (Ia) in the presence of an oxidizing agent for double bond cleavage selected from suitable oxidizing agents in organic chemistry, preferably selected from ozone or the combination of potassium peroxymonosulfate ($KHSO_5 \cdot KHSO_4 \cdot K_2SO_4$, oxone) in the presence of catalytic amounts of ruthenium trichloride.

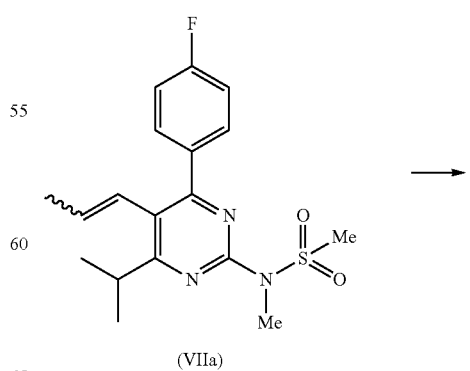

(VIIa)

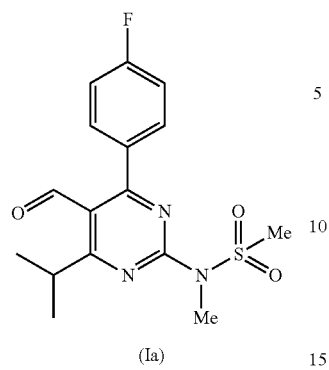

(Ia)

According to a preferred option (C) of an embodiment of the present invention the synthesis of heterocyclic aldehyde of formula (IIa) as a key intermediate for Rosuvastatin

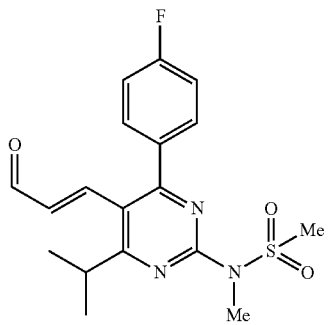

(IIa)

comprises l. providing (III-al-a) as described under Option B, m. brominating (III-al-a) at the terminal allyl carbon atom preferably in a radical bromination reaction with a brominating agent preferably with N-bromosuccinimide in an organic solvent selected from the group consisting of acetone, ethyl acetate, hydrocarbons, aromatic hydrocarbons, ethers, esters, chlorinated hydrocarbons and acetonitrile or a mixture thereof, preferably in carbon tetrachloride, under treatment of visible or ultraviolet radiation of 200-400 nm in batch or flow mode, at a temperature of about 15 to 50° C. for 2 to 10 hours,

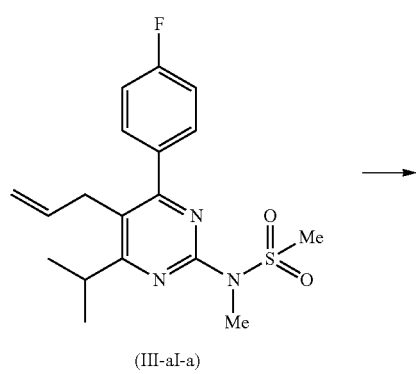

(III-al-a)

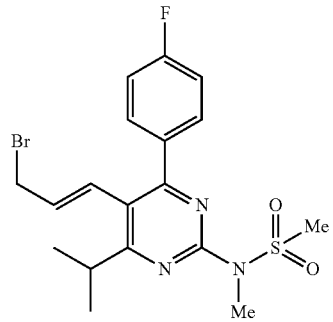

(VIa)

n. converting (VIa) without being isolated to alcohol (VIIIa) by nucleophilic substitution in the presence of a base selected from the group consisting of carbonates comprising alkaline, alkaline earth and earth metal carbonates, preferably sodium bicarbonate in aqueous form at a temperature between ambient temperature and reflux conditions for 10 minutes up to 24 hours.

(VIa)

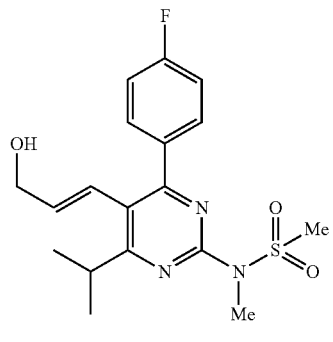

(VIIIa)

o. oxidizing (VIIIa) in the presence of an oxidizing agent selected from oxidizing agents in organic chemistry.

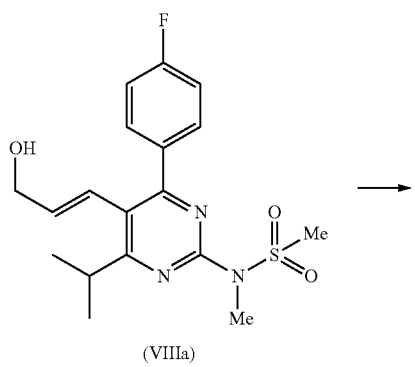

(VIIIa)

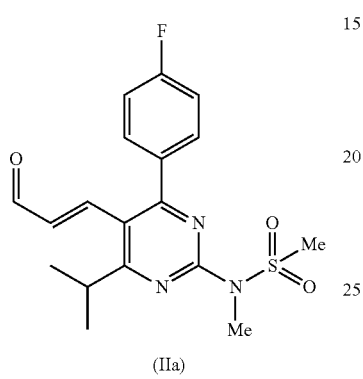

(IIa)

According to a preferred option (D) of an embodiment of the present invention the synthesis of heterocyclic aldehyde of formula (IIa) as a key intermediate for Rosuvastatin (IIa)

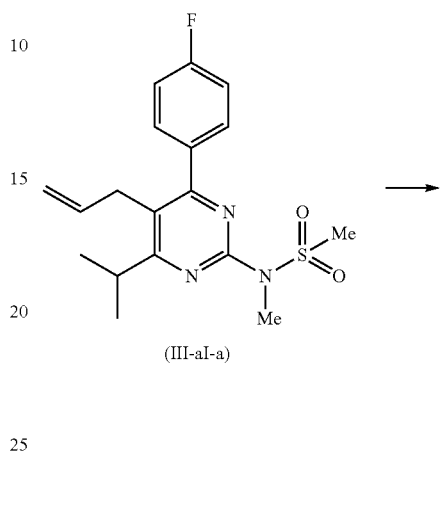

comprises
p. providing (III-al-a) as described under Option B,
q. oxidizing (III-al-a) to (IXa) by reaction with dimethyldioxirane, wherein the side product of the conversion is acetone, optionally in situ generated by reacting potassium peroxymonosulfate with acetone in the presence of a base selected from the group consisting of carbonates comprising alkaline, alkaline earth and earth metal carbonates, preferably sodium bicarbonate in an organic solvent selected from the group consisting of acetone, ethyl acetate, hydrocarbons, aromatic hydrocarbons, ethers, esters, chlorinated hydrocarbons and acetonitrile or a mixture thereof, preferably a mixture of dichloromethane and acetone, in the presence of water and a phase transfer catalyst selected from the group consisting of N-methyl-N,N,N-trioctylammonium chloride, benzyltrimethylammonium chloride, tetrabutylammonium chloride and hexadecyltributylphosphonium bromide, at preferably ambient temperatures for about 10 hours.

The phase transfer catalyst preferably is tetrabutylammonium chloride in an amount from about 0.01 to 0.5 times, preferably 0.1 times of the initial amount of (III-al-a). The oxidizing agent is added precooled at a temperature between −5 and 5° C., preferably at 0° C., and at a slow pace.

(III-aI-a)

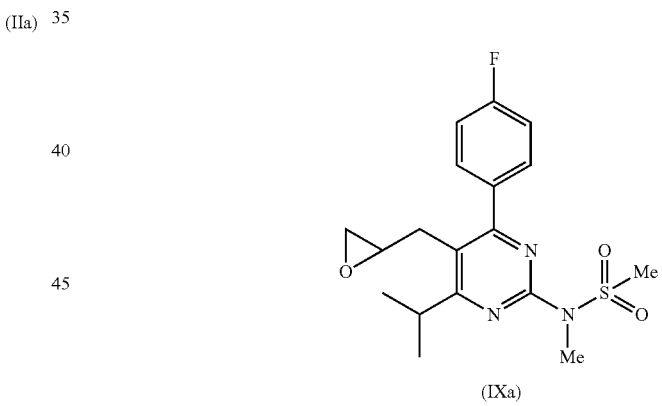

(IXa)

r. converting (IXa) to (VIIIa) in the presence of a base selected from the group consisting of organic bases such as amides, amidines, tertiary amines including pyridine, triethylamine, 1,4-diazabicyclo[2.2.2]octane (DABCO), preferably 1,4-diazabicyclo[2.2.2]octane (DABCO) in an organic solvent selected from the group consisting of acetone, ethyl acetate, hydrocarbons, aromatic hydrocarbons, ethers, esters, chlorinated hydrocarbons and acetonitrile or a mixture thereof, preferably 1,4-dioxane at a temperature between 0 to 101° C. preferably at only slightly elevated temperatures between 35 to 45° C. for 1 hour to 48 hours.

The initial amount of the base is from about 1 to about 8 times the molar stoichiometric amount based on compound (IXa), preferably about 2 times.

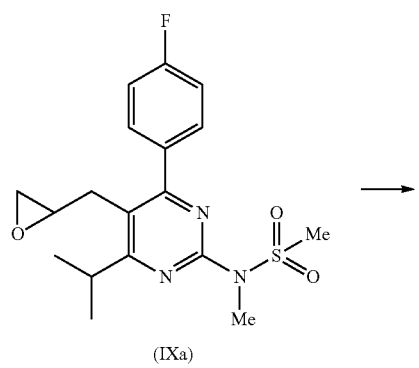

(IXa)

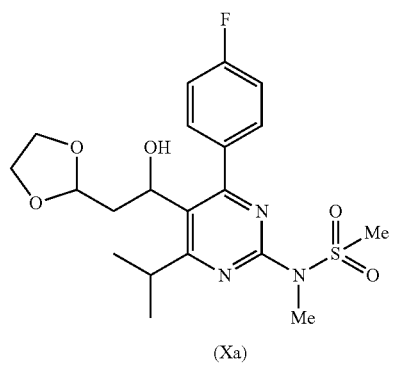

(Xa)

v. converting hydroxyl compound (Xa) to intermediate (XIa) by dehydration in the presence of an acid,

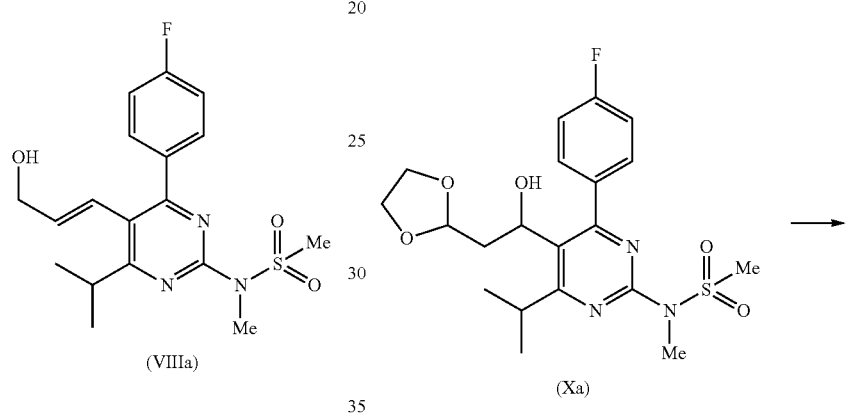

(VIIIa)  (Xa)

s. oxidizing (VIIIa) to heterocyclic aldehyde (IIa) as described in Option C.

According to a preferred option (E) of an embodiment of the present invention the synthesis of heterocyclic aldehyde of formula (IIa) as a key intermediate for Rosuvastatin comprises t. providing heterocyclic aldehyde (Ia) as described in Option A or B, u. converting the aldehyde (Ia) to hydroxyl compound (Xa) by reaction with an dioxolanymethyl nucleophile preferably a dioxolanymethyl Grignard reagent in an organic solvent selected from the group consisting of acetone, ethyl acetate, hydrocarbons, aromatic hydrocarbons, ethers, esters, and acetonitrile or a mixture thereof,

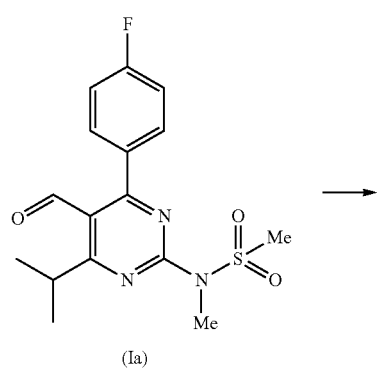

(Ia)

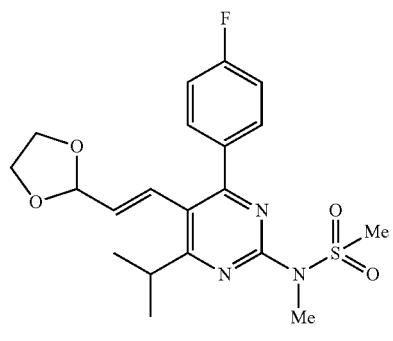

(XIa)

w. converting (XIa) to heterocyclic aldehyde (IIa) by deprotection of the dioxolanyl group in the presence of aqueous acid.

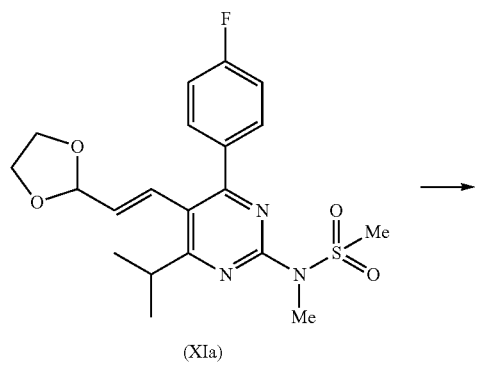

(XIa)

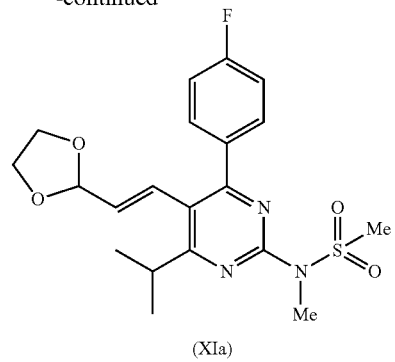

(XIa)

z. converting (XIa) to heterocyclic aldehyde (IIa) as described under Option E.

According to a preferred option (G) of an embodiment of the present invention the synthesis of heterocyclic aldehyde of formula (IIa) as a key intermediate for Rosuvastatin comprises aa. providing heterocyclic aldehyde (Ia) as described in Option A or B, bb. converting (Ia) directly to heterocyclic aldehyde (IIa) by reaction with ethylpyruvate in the presence of pyruvate decarboxylase.

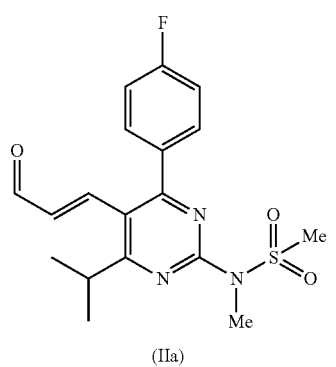

(IIa)

According to a preferred option (F) of an embodiment of the present invention the synthesis of heterocyclic aldehyde of formula (IIa) as a key intermediate for Rosuvastatin comprises x. providing heterocyclic aldehyde (Ia) as described in Option A or B, y. converting (Ia) to intermediate (XIa) by a Wittig type reaction with dioxolanylmethylenetriphenylphosphane in the presence of a base selected from the group consisting of inorganic basic salts and organic bases in an organic solvent selected from the group consisting of acetone, ethyl acetate, hydrocarbons, aromatic hydrocarbons, ethers, esters, chlorinated hydrocarbons and acetonitrile or a mixture thereof,

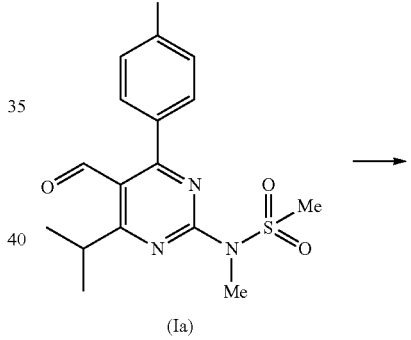

(Ia)

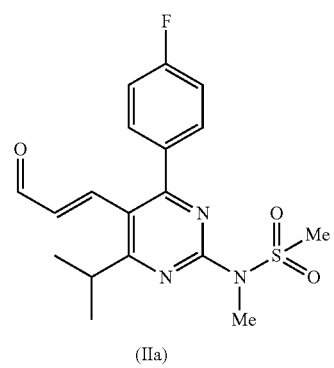

(IIa)

According to a preferred option (H) of an embodiment of the present invention the synthesis of heterocyclic aldehyde of formula (IIa) as a key intermediate for Rosuvastatin comprises cc. providing heterocyclic aldehyde (Ia) as described in Option A or B, dd. converting (Ia) directly to heterocyclic aldehyde (IIa) by reaction with acetaldehyde.

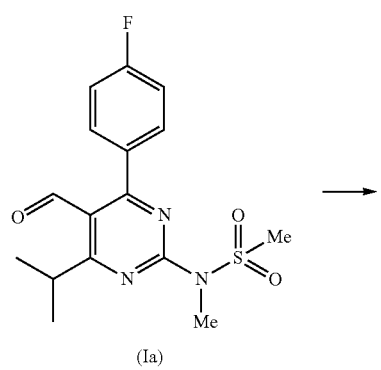

(Ia)

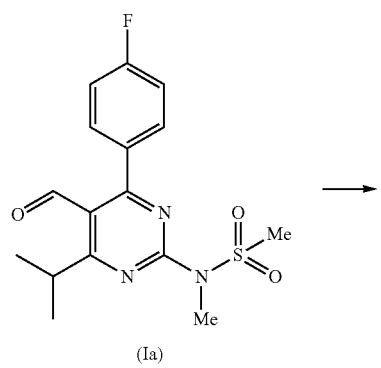

(Ia)

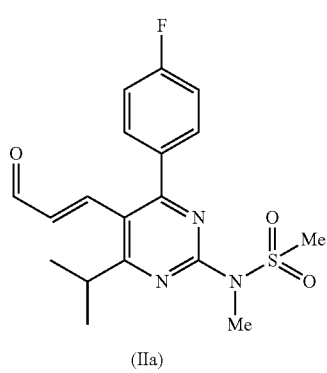

(IIa)

According to a preferred option (I) of an embodiment of the present invention the synthesis of ketone of formula (XII-Me-b) as a key intermediate for Pitavastatin comprises ee. reacting cyclopropylcarbaldehyde with an ethyl Grignard reagent, preferably an ethyl magnesium halide, more preferably a chloride, bromide or iodide reagent in an organic solvent selected from the group consisting of acetone, ethyl acetate, hydrocarbons, aromatic hydrocarbons, ethers, esters, and acetonitrile or a mixture thereof, preferably an ether type solvent, more preferably in THF or diethyl ether and subsequent aqueous work up to 1-cyclopropyl-1-hydroxypropane,

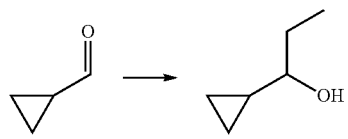

ff. oxidizing 1-cyclopropyl-1-hydroxypropane to cyclopropylpropanone (XII-Me-b) with an oxidizing agent selected from oxidizing agents in organic chemistry,

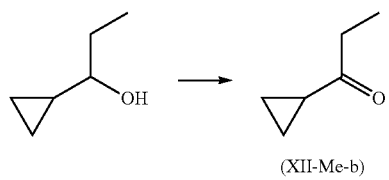

(XII-Me-b)

According to a preferred option (J) of an embodiment of the present invention the synthesis of ketone of formula (XII-Me-b) as intermediate for Pitavastatin comprises gg. converting derivatives of cyclopropanecarboxylic acid (XVIb), wherein R' is selected from a group consisting of electron withdrawing groups comprising alkoxy, arylmethoxy, hydroxyl, N,O-dialkylhydroxylamino and halides, preferably cyclopropanecarboxylic chloride and cyclopropanecarboxylic ethyl ester to cyclopropylpropanone (XII-Me-b) by reaction with an ethyl Grignard reagent, preferably an ethyl magnesium halide, more preferably a chloride, bromide or iodide reagent in an organic solvent selected from the group consisting of acetone, ethyl acetate, hydrocarbons, aromatic hydrocarbons, ethers, esters, and acetonitrile or a mixture thereof, preferably an ether type solvent,

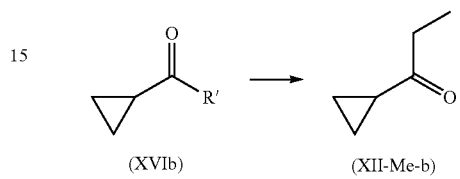

(XVIb)                (XII-Me-b)

According to a preferred option (K) of an embodiment of the present invention the synthesis of ketone of formula (XII-al-b) as intermediate for Pitavastatin comprises hh. reacting cyclopropyl derivatives (XVIIb), wherein R'' is selected from a group consisting of electron withdrawing groups comprising alkyl carboxylates, aryl carboxylates, carboxyl halides and cyanide, preferably cyclopropanecarboxylic chloride, cyclopropyl nitrile and cyclopropanecarboxylic ethyl ester with an n-butenyl Grignard reagent, preferably an n-butenyl magnesium halide, more preferably a chloride, bromide or iodide reagent in an organic solvent selected from the group consisting of acetone, ethyl acetate, hydrocarbons, aromatic hydrocarbons, ethers, esters, and acetonitrile or a mixture thereof, preferably an ether type solvent and subsequent aqueous work up to compound (XII-al-b),

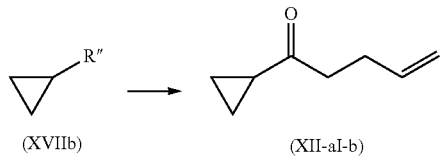

(XVIIb)                (XII-al-b)

According to a preferred option (L) of an embodiment of the present invention the synthesis of ketone of formula (XII-al-b) as intermediate for Pitavastatin comprises ii. converting 1-cyclopropyl-1-N-cyclohexylimidoethane to 1-cyclopropylpent-4-enone (XII-al-b) by an allylation reaction with an electrophilic allyl sources as allylating reagent selected from the group consisting of allyl halides, preferably allyl bromide.

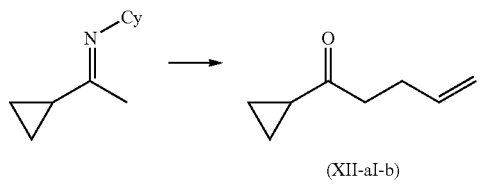

(XII-al-b)

According to a preferred option (M) of an embodiment of the present invention the synthesis of heterocyclic aldehyde of formula (Ib) as a key intermediate for Pitavastatin

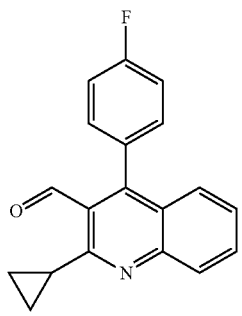

(Ib)

comprises jj. converting compound (XII-Me-b) in a cyclization reaction with 2-amino-4'-fluorobenzophenone to heterocycle (III-Me-b) in the presence of an acid selected from the group consisting of inorganic acids, diluted or concentrated, comprising hydrochloric acid, sulfuric acid, nitric acid, phosphorous acid, acetic acid, hydrobromic acid, triflic acid, trifluoroacetic acid, methanesulfonic acid, para toluenesulfonic acid and the like,

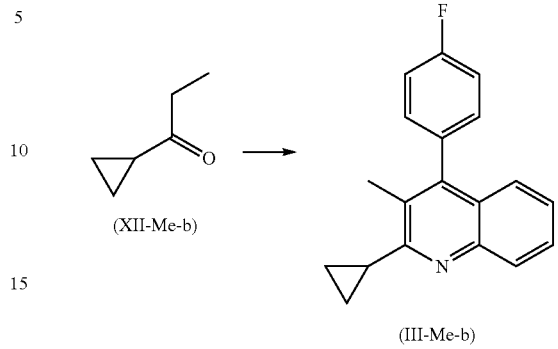

kk. converting (III-Me-b) to heterocyclic aldehyde (Ib) via (IVb) and (Vb) according to the conversion of (III-Me-a) via intermediates (IVa) and (Va) to aldehyde (Ia) as described in Option A d-f.

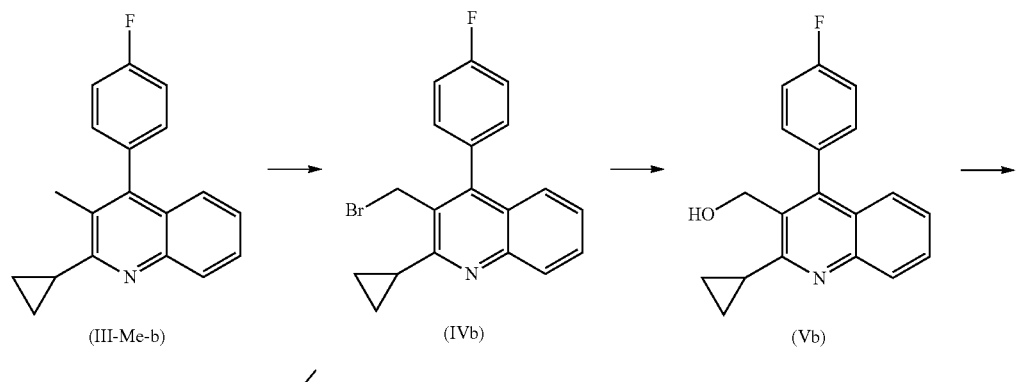

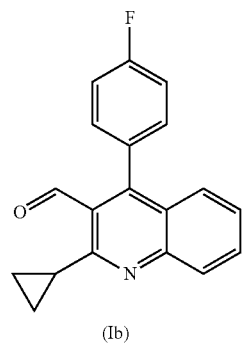

(Ib)

According to a preferred option (N) of an embodiment of the present invention the synthesis of heterocyclic aldehyde of formula (Ib) as a key intermediate for Pitavastatin

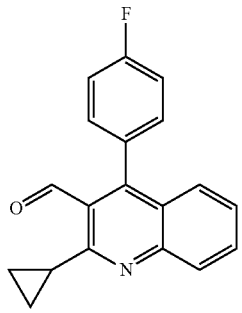

(Ib)

comprises ll. providing (XII-aI-b) as described in Options K and L, mm. converting 1-cyclopropylpent-4-enone (XII-aI-b) to the heterocyclic allyl derivative (III-aI-b) by reaction with 2-amino-4'-fluorobenzophenone in the presence of an acid selected from the group consisting of inorganic acids, diluted or concentrated, comprising hydrochloric acid, sulfuric acid, nitric acid, phosphorous acid, acetic acid, hydrobromic acid, triflic acid, trifluoroacetic acid, methanesulfonic acid, para toluenesulfonic acid and the like,

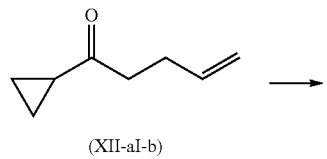

(XII-aI-b)

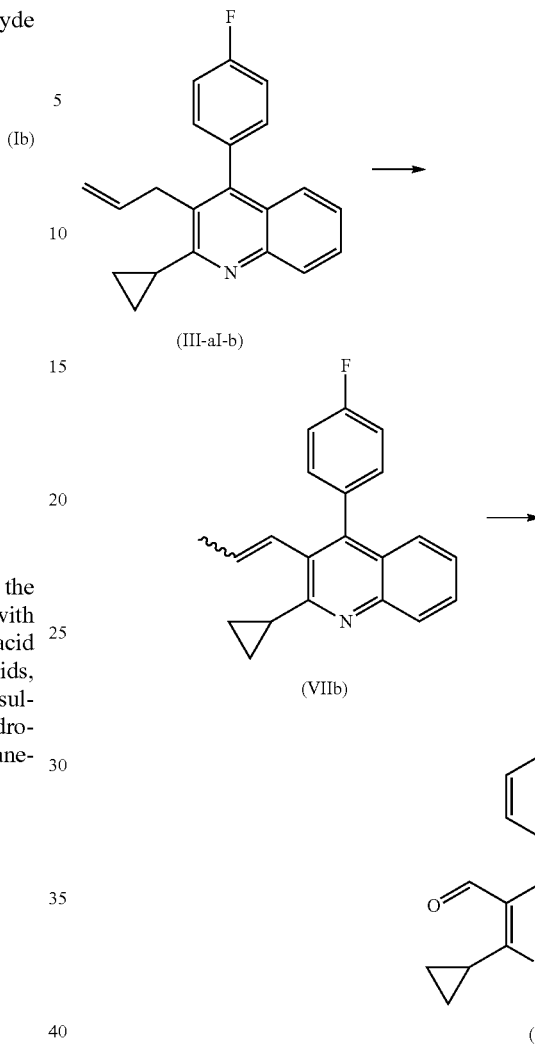

nn. converting (III-aI-b) to heterocyclic aldehyde (Ib) via intermediate (VIIb) to aldehyde (Ib) according to the conversion of (VIIa) to (Ia) as described in Option B j-k.

According to a preferred option (O) of an embodiment of the present invention the synthesis of heterocyclic aldehyde of formula (IIb) as a key intermediate for Pitavastatin

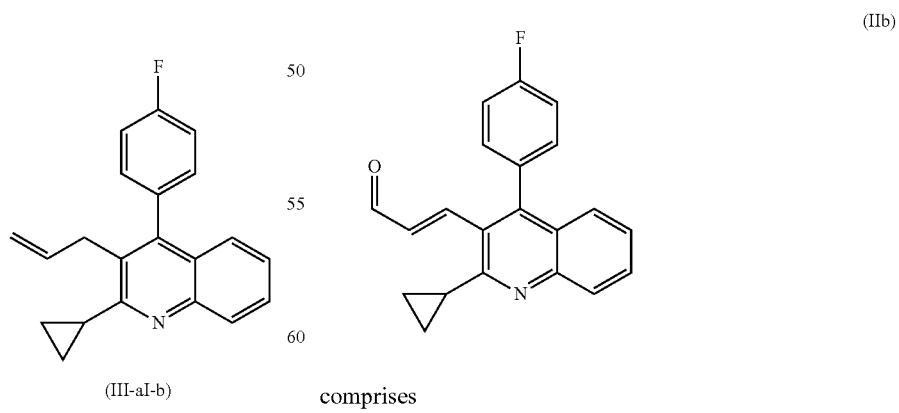

comprises oo. providing (III-aI-b) as described under Options K and L, pp. converting (III-aI-b) via intermediates (VIb) and (VIIIb) to heterocyclic aldehyde (IIb) according to the conversion of (III-aI-a) to (IIa) as described in Option C m-o.

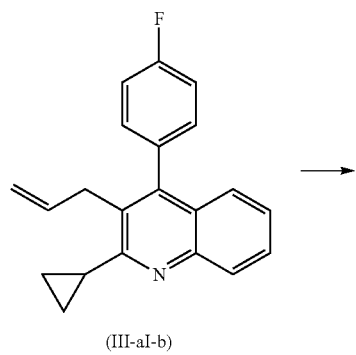

(III-aI-b)

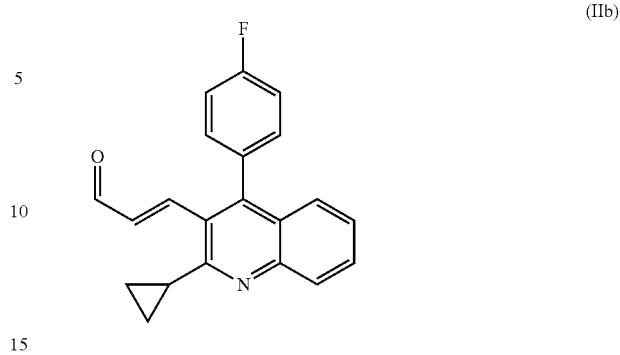

(IIb)

comprises qq. providing (III-al-b) as described under Options K and L, rr. converting (III-al-b) via intermediates (VIb) and (VIIIb) to heterocyclic aldehyde (IIb) according to the conversion of (III-al-a) to (IIa) as described in Option D q-s.

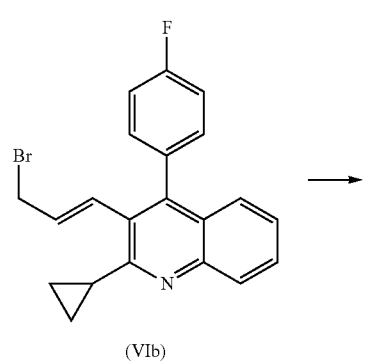

(VIb)

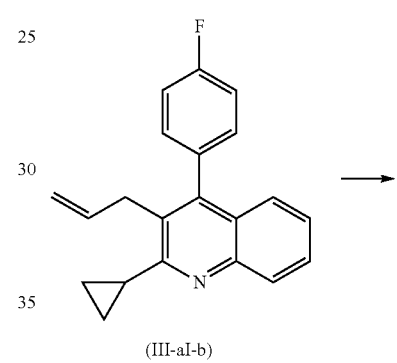

(III-aI-b)

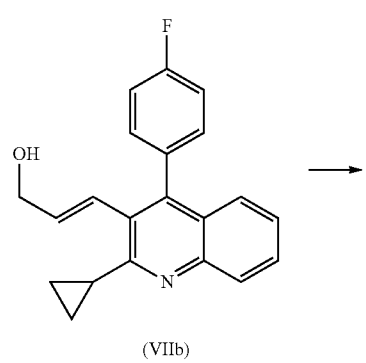

(VIIb)

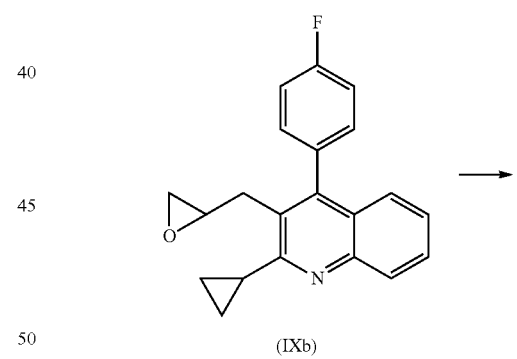

(IXb)

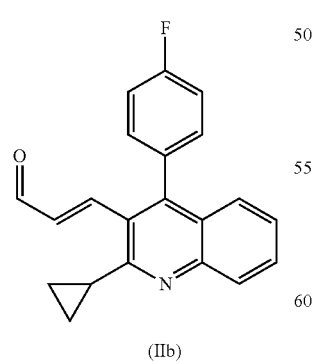

(IIb)

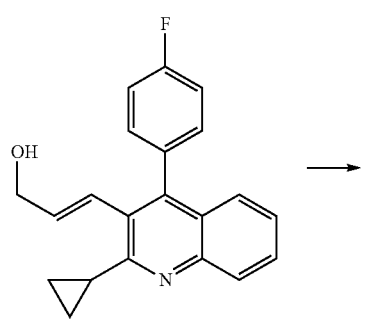

(VIIIb)

According to a preferred option (P) of an embodiment of the present invention the synthesis of heterocyclic aldehyde of formula (IIb) as a key intermediate for Pitavastatin

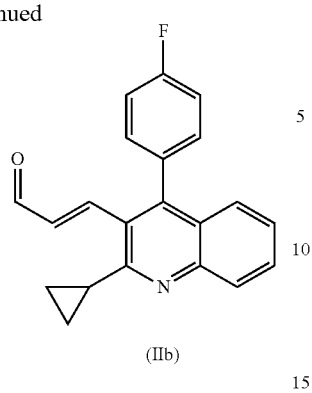

(IIb)

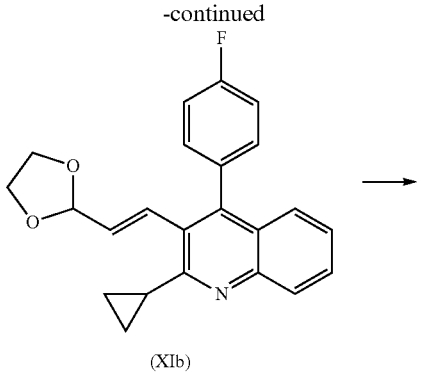

(XIb)

According to a preferred option (Q) of an embodiment of the present invention the synthesis of heterocyclic aldehyde of formula (IIb) as a key intermediate for Pitavastatin comprises ss. providing heterocyclic aldehyde (Ib) as described in Option I or J, tt. converting (Ib) via intermediates (Xb) and (XIb) to heterocyclic aldehyde (IIb) according to the conversion of (Ia) to (IIa) as described in Option E u-w,

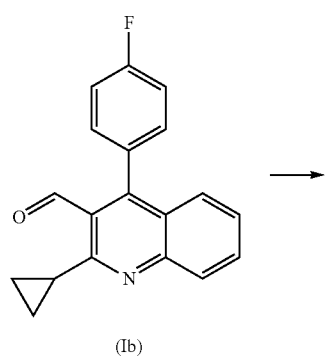

(Ib)

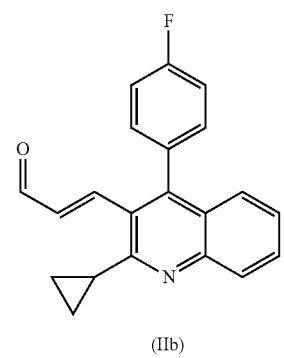

(IIb)

According to a preferred option (R) of an embodiment of the present invention the synthesis of heterocyclic aldehyde of formula (IIb) as a key intermediate for Pitavastatin comprises uu. providing heterocyclic aldehyde (Ib) as described in Option I or J, vv. converting (Ib) to heterocyclic aldehyde (IIb) according to the conversion of (Ia) to (IIa) as described in Options H and I.

The key intermediate compounds of formula I and II can then be subjected to further synthesis steps in order to yield Rosuvastatin or pharmaceutically acceptable salts thereof or Pitavastatin or pharmaceutically acceptable salts thereof by synthesis routes known to or readily devisable by a person skilled in the art. As shown in the schemes below, following synthesis routes may be applied:

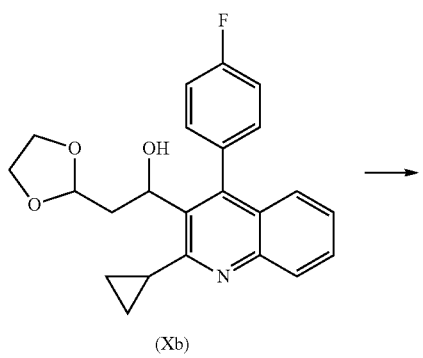

(Xb)

Scheme 19
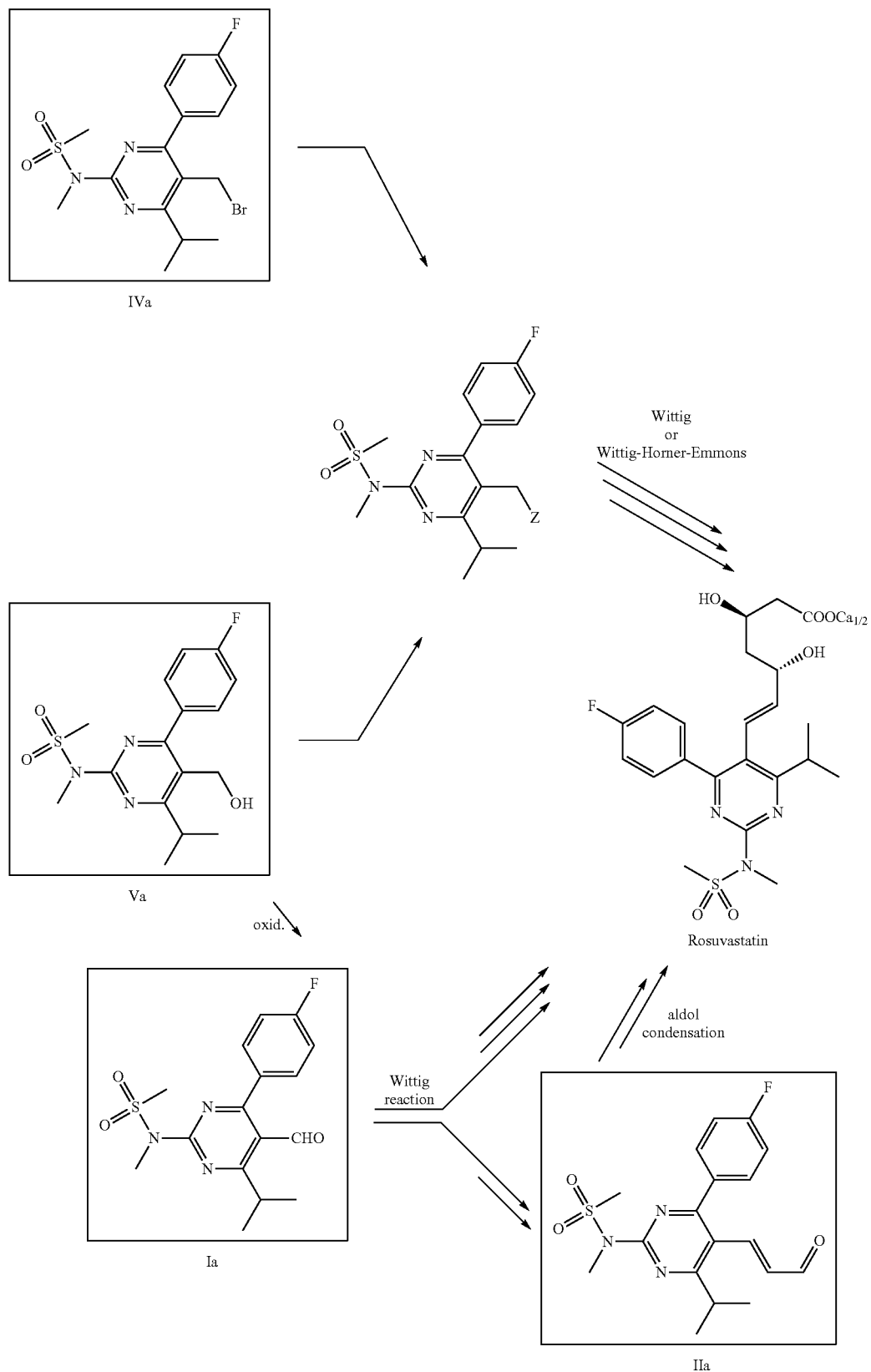

-continued
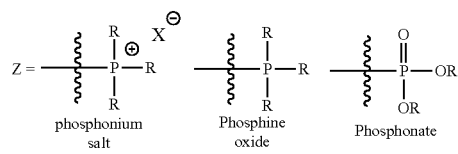
Scheme 20
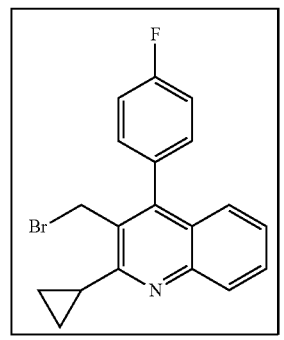
IVb
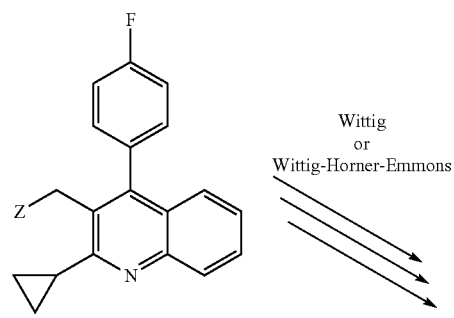
Wittig
or
Wittig-Horner-Emmons
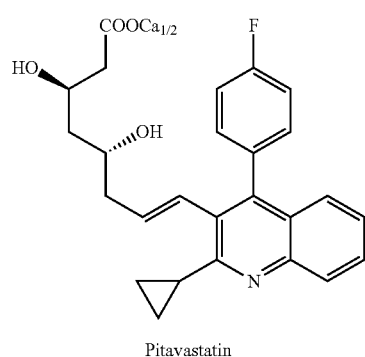
Pitavastatin
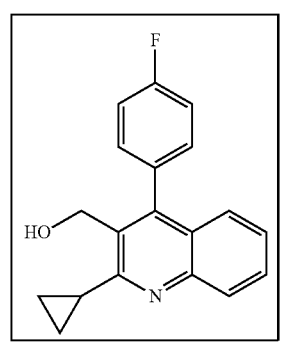
Vb
oxid.

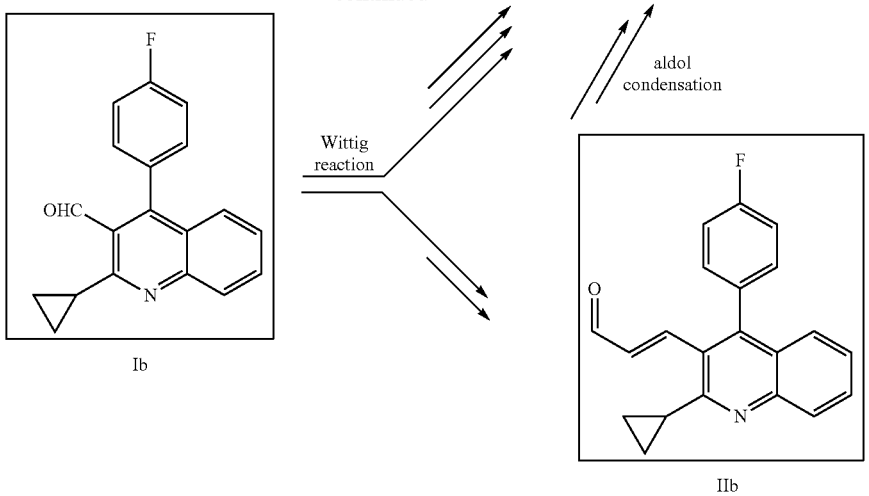

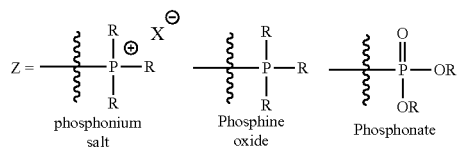

For preparing a pharmaceutical composition comprising Rosuvastatin and Pitavastatin or respective pharmaceutically acceptable salts thereof as active ingredients, first the respective pharmaceutical composition or pharmaceutically acceptable salts thereof is provided by the process as described above.

Then, the thus prepared respective pharmaceutical composition or pharmaceutically acceptable salts thereof is suitably admixed with at least one suitable pharmaceutically acceptable excipient. Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology.

Preferably, excipients may be selected from the group consisting of lactose, microcrystalline cellulose, cellulose derivatives, e.g. hydroxypropylcellulose, polyacrylates, calcium carbonate, starch, colloidal silicone dioxide, sodium starch glycolate, talc, magnesium stearate, polyvinylpyrrolidone, polyethylene glycol and other excipients known in the field of the pharmaceutical technology.

EXPERIMENTAL PROCEDURES

Example 1

Preparation of 1-(4-fluorophenyl)-2,4-dimethylpentane-1,3-dione (MDK)

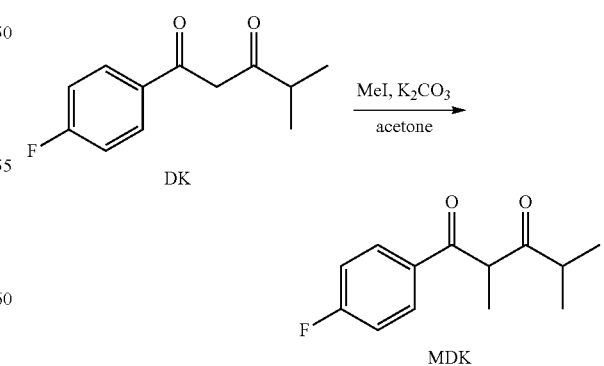

A mixture of DK (1.0 g, 4.8 mmol), $K_2CO_3$ (0.67 g, 4.8 mmol) and MeI (0.37 mL, 6.0 mmol) in acetone (1.5 mL) was stirred at room temperature for 24 hours. N-heptane (1.5 mL)

was added. Solids were filtered off and washed with acetone/n-heptane=1/1 (10 mL). Combined organic fractions were concentrated and re-dissolved in ethyl acetate (5 mL). Organic phase was washed with HCl (2 M, 3×5 mL), NaHCO$_3$ (saturated solution in water, 3×3 mL), brine (10 mL), dried over magnesium sulfate and concentrated to give 1.01 g (95% yield) of MDK.

$^1$H NMR (CDCl$_3$): δ 1.01 (3H, d, J=6.9 Hz), 1.08 (3H, d, J=6.8 Hz), 1.42 (3H, d, J=7.0 Hz), 2.75 (1H, sep, J=6.8 Hz), 4.58 (1H, q, J=7.0 Hz), 7.13 (2H, m), 7.98 (2H, m) ppm. $^{13}$C NMR (CDCl$_3$): δ 13.6, 18.5, 19.0, 39.3, 54.5, 115.8, 116.1, 131.2, 131.3, 132.4, 132.5, 164.6, 167.2, 195.9, 210.7 ppm.

Example 2

Preparation of 4-(4-fluorophenyl)-6-isopropyl-N,5-dimethylpyrimidin-2-amine (CMDK)

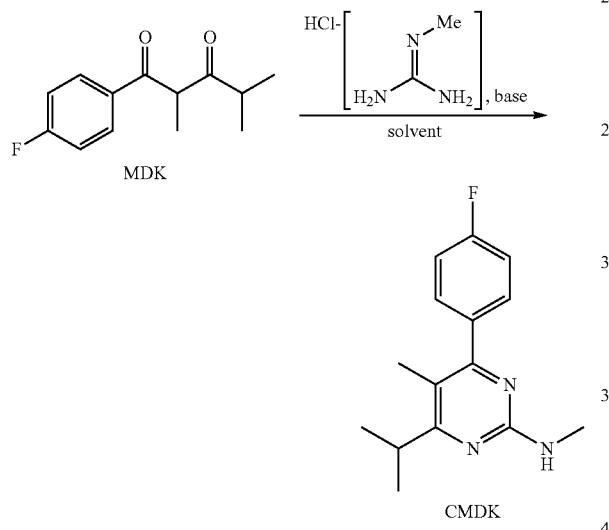

a) with NaH base and THF solvent:

A mixture of MDK (36.0 g, 0.162 mol) and N-methyl guanidine HCl salt (17.8 g, 0.162 mol) in dry THF (200 mL) was stirred at room temperature for 10 min. To a resulting suspension NaH (60% in mineral oil, 6.52 g, 0.162 mol) was added in 3 portions over 10 min and the reaction mixture was stirred at 40° C. for 8 hours. Water (20 mL) was then added and reaction mixture was left to cool to room temperature. Solvent was evaporated under reduced pressure and resulting oil was re-dissolved in MTBE (200 mL). Phases were separated and MTBE fraction was further washed with NH$_4$Cl (saturated water solution, 2×20 mL), water (1×20 mL), NaHCO$_3$ (saturated solution in water, 3×50 mL), brine (50 mL), dried over magnesium sulfate and concentrated to 1/10 of volume. Resulting precipitate was filtered off and washed with methanol (2×20 mL) to afford 20 g (48% yield) of CMDK as colorless solid.

b) with Cs$_2$CO$_3$ base and MeTHF solvent:

A mixture of 1-(4-fluorophenyl)-2,4-dimethylpentane-1,3-dione (MDK, 1.00 g, 4.5 mmol), N-methyl guanidine hydrochloride salt (0.49 g, 4.5 mmol) and Cs$_2$CO$_3$ (2.61 g, 8.0 mmol) in MeTHF (10 mL) was stirred at 40° C. for 10 h. The resulting suspension was cooled down to room temperature. Water (10 mL) and MeTHF (10 mL) were added. Layers were separated and the water layer was back-extracted with MeTHF (10 mL). The combined MeTHF fractions were washed with brine (20 mL) and dried over magnesium sulphate. Then, approximately 90% of the solvent was evaporated under reduced pressure and methanol (5 mL) was added to the resulting oily residue. White crystalline precipitate was collected by filtration, washed with ice-cold methanol (5 mL) and dried to afford the pyrimidine derivative CMDK (1.1 g, 92%) as pale yellow solid.

$^1$H NMR (CDCl$_3$): δ 1.25 (6H, d, J=6.7 Hz), 2.11 (3H, s), 2.93 (3H, d, J=5.1 Hz), 3.18 (1H, sep, J=6.7 Hz), 5.15 (1H, m), 7.12 (2H, m), 7.48 (2H, m) ppm. $^{13}$C NMR (CDCl$_3$): δ 13.8, 21.0, 28.3, 31.4, 112.8, 114.9, 115.1, 130.6, 130.7, 135.99, 136.02, 161.0, 161.5, 163.9, 164.9, 174.9 ppm.

Example 3

Preparation of N-(4-(4-fluorophenyl)-6-isopropyl-5-methylpyrimidin-2-yl)-N-methylmethanesulfonamide (PMDME)

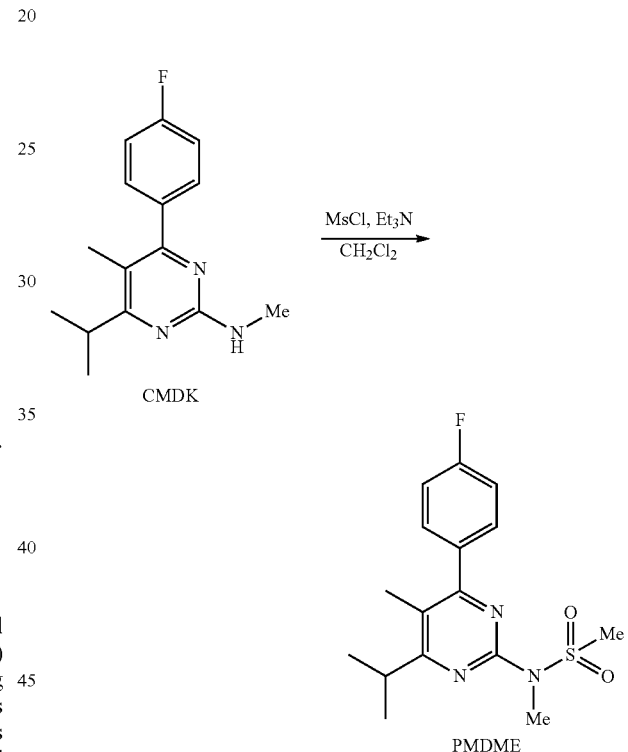

a) A solution of CMDK (1.0 g, 3.86 mmol) and Et$_3$N (0.65 mL, 4.63 mmol) in CH$_2$Cl$_2$ (10 mL) was cooled to 0° C. MsCl (0.6 mL, 7.72 mmol) was added and reaction was left to gradually warm to room temperature over 2 hours and left to stir at room temperature for 24 hours. CH$_2$Cl$_2$ (10 mL) and HCl (2 M, 10 mL) were added to reaction mixture and phases were separated. Organic phase was washed with HCl (2 M, 2×5 mL), NaHCO$_3$ (saturated water solution, 3×10 mL), brine (20 mL), dried over magnesium sulfate and solvent was evaporated under reduced pressure. CH$_2$Cl$_2$ (5 mL) and ethyl acetate/n-hexane=1/20 (1 mL) were added. Precipitated solids were filtered off and washed with ethyl acetate/n-hexane=1/20 (5 mL) to give 780 mg (60% yield) of PMDME.

b) A solution of CMDK (1.0 g, 3.86 mmol) in dichloromethane (15 mL) was prepared under dry atmosphere (N$_2$) and cooled to −5° C. Then Et$_3$N (2.15 mL, 15.4 mmol, 4.0 equiv.) was added via a syringe and the reaction mixture was stirred for 10 min. A solution of MsCl (750 μL, 9.65 mmol, 2.5 equiv.) in dry dichloromethane (1.0 mL) was prepared and slowly added (flow rate=250 μL/h) into the reaction mixture via a syringe. The stirring was continued for additional 8 h at −5° C. After dilution with dichloromethane (5 mL) and gradually warming up to room temperature, the reaction mixture was washed with water (6 mL). Aqueous layer was back-extracted with dichloromethane (5 mL) and the combined organic layers were washed with HCl (1 M, 3×6 mL), saturated aq. NaHCO$_3$ solution (3×6 mL) and brine (2×7 mL). The organic layers were passed through a thin pad of silica gel-MgSO$_4$ (prewashed with 5 mL of dichloromethane) and n-hexane (10 mL) is added. Solvents are evaporated to 1/5 of the initial volume, solids filtered off and washed with MeOH (7 mL). Filtrate is evaporated to half volume, precipitate filtered off and combined with previously filtered solids to give 1.18 g (91% yield) of 5-methylpyrimidine PMDME as colorless crystals.

$^1$H NMR (CDCl$_3$): δ 1.30 (6H, d, J=6.7 Hz), 2.27 (3H, s), 3.29 (1H, sep, J=6.7 Hz), 3.50 (3H, s) 3.54 (3H, s), 7.14 (2H, m), 7.55 (2H, m) ppm. $^{13}$C NMR (CDCl$_3$): δ 14.1, 21.1, 31.7, 32.9, 42.2, 114.9, 115.2, 118.5, 131.0, 131.1, 134.57, 134.60, 156.6, 161.7, 164.2, 164.5, 175.2 ppm.

Example 4

Preparation of N-(4-(4-fluorophenyl)-5-bromomethyl-6-isopropylpyrimidin-2-yl)-N-methylmethanesulfonamide (PMDBR) and N-(4-(4-fluorophenyl)-5-hydroxymethyl-6-isopropylpyrimidin-2-yl)-N-methylmethanesulfonamide (PMDOH) via N-(4-(4-fluorophenyl)-5-bromomethyl-6-isopropylpyrimidin-2-yl)-N-methylmethanesulfonamide (PMDBR)

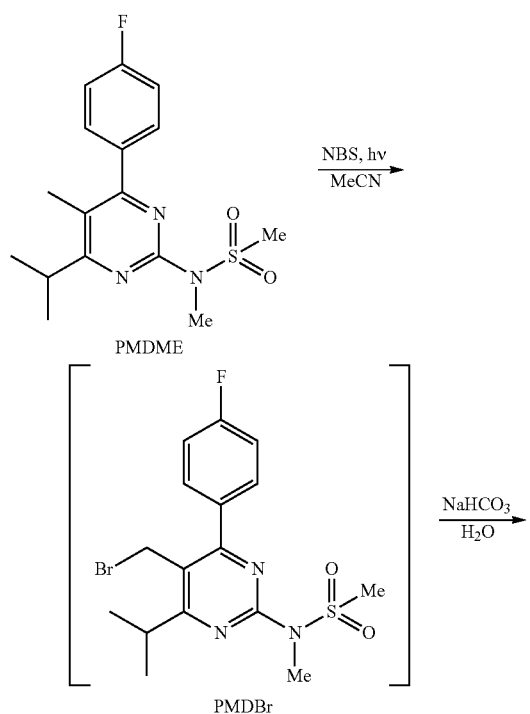

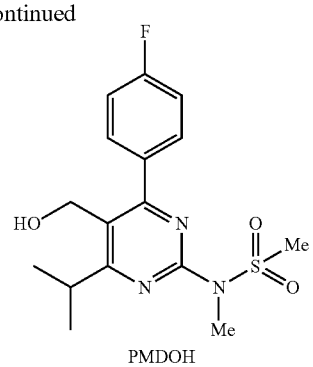

PMDOH a) Batch synthesis of PMDBR (i) Low pressure Hg-lamp: PMDME (3.94 g, 11.7 mmol, 1 equiv.) and N-bromosuccinimide (NBS) (2.1 equiv.) were dissolved in 75 mL of acetonitrile. The mixture was stirred and irradiated in a photo reactor with light of a wavelength λ=254 nm (low pressure Hg-lamp, P=6 W) for 68 hours at ambient temperature (about 20° C.). The obtained dark red solution was diluted with H$_2$O (70 mL). Precipitate was filtered off and washed with MeOH/H$_2$O=1/1 (30 mL) and MeOH (10 mL) to afford 3.88 g of PMDBR (80% yield) as off-white crystals.

(ii) Medium pressure Hg-lamp: PMDME (8.00 g, 23.7 mmol, 1 equiv.) and N-bromosuccinimide (NBS) (2.1 equiv.) are dissolved in acetonitrile (70 mL) and transferred to photo reactor. Reactor is sealed and flushed with nitrogen for 10 min. The mixture is stirred and irradiated with a medium pressure Hg-lamp (P=150 W, polychromatic emission spectra between 200 and 400 nm) for 24 hours. Medium pressure Hg-lamp is in a quartz immersion jacket cooled with water and stabilized at 40-45° C. The obtained red colored solution is diluted with H$_2$O (100 mL) and methanol (10 mL). Precipitate is filtered off and recrystallized from ethyl acetate to afford 7.1 g of PMDBR (72% yield) as yellow crystals.

b) Flow mode synthesis of PMDBR

Flow reactor is prepared by 30 min of medium pressure Hg-lamp stabilization within a quartz jacket with water cooling stabilization to 40-45° C. Care must be taken to seal the reactor with aluminium foil against stray radiation. Starting PMDME (11.4 g, 38.6 mmol, 1 equiv.) and N-bromosuccinimide (NBS) (2.1 equiv.) are dissolved in acetonitrile (100 mL), sealed and flushed for 10 min with nitrogen. Solution is pumped via a syringe pump through a pre-prepared flow reactor with the flow rate of 600 μL per minute (30 min retention time). When reaction mixture is collected (50 mL), water (70 mL) and MeOH (5 mL) are added and precipitate filtered. Precipitate is recrystallized form ethyl acetate to afford 7.1 g (89% yield) of PMDBR as yellow crystalline solid.

$^1$H NMR (CDCl$_3$): δ 1.35 (6H, d, J=6.6 Hz), 3.46-3.52 (4H, m), 3.56 (3H, s), 4.48 (2H, s) 7.20 (2H, m), 7.81 (2H, m) ppm. $^{13}$C NMR (CDCl$_3$): δ 21.9.1, 27.7, 31.5, 33.1, 42.5, 115.5, 115.7, 119.3, 130.7, 130.8, 133.5, 133.6, 157.9, 162.3, 164.8, 165.6, 177.5 ppm.

c) One-pot synthesis of PMDOH (PMDME) (113. mg, 0.33 mmol, 1 equiv.) and N-bromosuccinimide (NBS) (119 mg, 0.66 mmol, 2 equiv.) were dissolved in 2 mL of acetonitrile. The mixture was irradiated with light of a wavelength λ=254 nm for 4 hours at ambient temperature (about 20° C.). The obtained yellow solution of PMDBR was diluted with 1 mL of acetonitrile. After 2 mL of saturated NaHCO₃ solution was added, the obtained mixture was further stirred under reflux for 4 hours. Then the mixture was cooled to room temperature, water (10 mL) was added and the mixture was extracted with CH₂Cl₂ (3×10 mL). The combined organic phases were washed with 10 mL of brine, and the obtained solution was dried with Na₂SO₄. Solvent was removed under the reduced pressure to give 110.8 mg (95%) of crude N-(4-(4-fluorophenyl)-5-(hydroxymethyl)-6-isopropylpyrimidin-2-yl)-N-methylmethanesulfonamide (PMDOH), which contained 77% of N-(4-(4-fluorophenyl)-5-(hydroxymethyl)-6-isopropylpyrimidin-2-yl)-N-methyl-methanesulfonamide (PMDOH) as determined by ¹H-NMR integral. This product was further purified by crystallization from MTBE/hexane mixture to afford pure material (HPLC area %=99.6) with T$_m$=140-141° C.

¹H NMR (CDCl₃): δ 1.30 (6H, d, J=6.6 Hz), 2.51 (1H, s), 3.44-3.50 (4H, m), 3.54 (3H, s) 4.58 (2H, d, J=2.5 Hz), 7.11 (2H, m), 7.79 (2H, m) ppm.

Example 5

Preparation of 2-allyl-1-(4-fluorophenyl)-4-methyl-pentane-1,3-dione (ALDK)

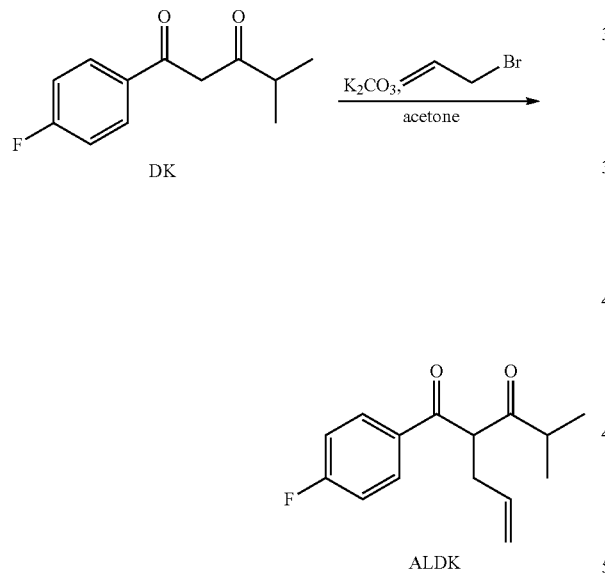

A mixture of DK (200 g, 0.962 mol) and K₂CO₃ (146 g, 1.05 mol) in acetone (500 mL) was stirred at room temperature for 10 min. To a reaction suspension, allylbromide (92 mL, 1.15 mol) was added dropwise during 10 min and reaction suspension was left to stir for 4 hours at room temperature. The solids were filtered off and washed with acetone (2×100 mL) and organic fractions combined and evaporated. Residue was re-dissolved in MTBE (500 mL) and washed with HCl (2 M, 2×100 mL), NaHCO₃ (saturated solution in water, 100 mL), brine (200 mL), dried over magnesium sulfate and evaporated under reduced pressure to afford 231 g (96% yield) of ALDK as colorless oil.

¹H NMR (CDCl₃): δ 0.99 (3H, d, J=6.9 Hz), 1.04 (3H, d, J=6.7 Hz), 2.65 (3H, m), 4.60 (1H, t, J=6.9 Hz), 4.98-5.08 (2H, m), 5.67-5.76 (1H, m), 7.14 (2H, m), 7.99 (2H, m) ppm.

¹³C NMR (CDCl₃): δ 18.3, 18.9, 32.9, 39.6, 60.5, 115.9, 116.1, 117.4, 131.3, 131.4, 132.8, 132.9, 134.6, 164.7, 167.3, 194.3, 208.9 ppm.

Example 6

Preparation of 5-allyl-4-(4-fluorophenyl)-6-isopropyl-N-methylpyrimidin-2-amine (CALDK)

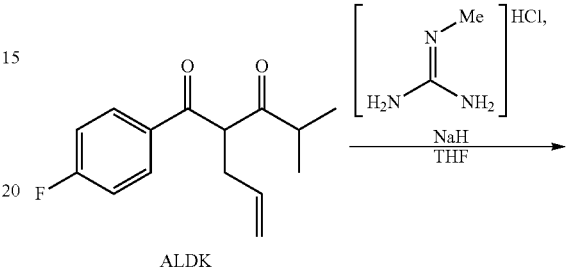

A mixture of ALDK (2.0 g, 8.68 mmol) and N-methyl guanidine HCl salt (3.8 g, 34.7 mmol) in dry tetrahydrofuran (THF) (50 mL) was stirred at room temperature for 20 min. NaH (60% suspension in mineral oil, 1.39 g, 34.7 mmol) was added in 2 portions during 10 min and reaction was kept at constant temperature of 25° C. for 48 hours. Tetrahydrofuran (THF, 20 mL) was added, solids were filtered off and washed thoroughly with THF (2×10 mL). Organic fractions were combined and solvent was evaporated. Crude solids were purified by reverse phase colomn chromatography to afford 0.74 g (30% yield) of CALDK as colorless solid.

¹H NMR (CDCl₃): δ 1.23 (6H, d, J=6.7 Hz), 3.02 (3H, d, J=5.1 Hz), 3.11 (1H, sep, J=6.7 Hz), 3.21 (2H, m), 4.84-4.89 (1H, m), 4.98 (1H, m), 5.10-5.14 (1H, m), 5.93-6.02 (1H, m), 7.09 (2H, m), 7.50 (2H, m) ppm. ¹³C NMR (CDCl₃): δ 21.8, 28.4, 30.9, 31.4, 114.3, 114.9, 115.1, 115.7, 130.1, 130.2, 135.81, 135.84, 137.6, 161.5, 161.7, 164.1, 166.1, 176.1 ppm.

Example 7

Preparation of N-(5-allyl-4-(4-fluorophenyl)-6-isopropylpyrimidin-2-yl)-N-methylmethane-sulfonamide (MCALDK)

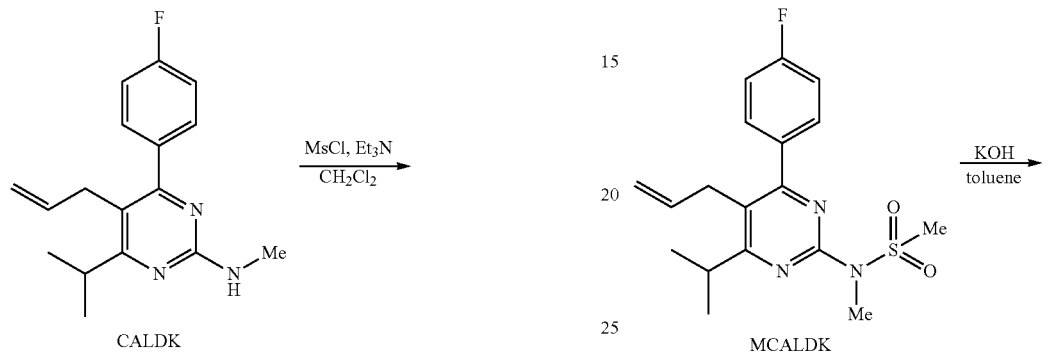

CALDK (30 g, 0.105 mol) was dissolved in dry $CH_2Cl_2$ (420 mL) and $Et_3N$ (58 mL, 0.42 mol) was added. Reaction mixture was cooled to −5° C. and MsCl (20 mL, 0.263 mol) in dry $CH_2Cl_2$ (30 mL) was added over 7 hours. Reaction mixture was left to stir at −5° C. for additional 10 hours. Dichloromethane (100 mL) was added and mixture was left to warm to room temperature. Organic phase was washed with water (100 mL), HCl (1 M, 3×200 mL), $NaHCO_3$ (saturated solution in water, 3×200 mL), brine (2×200 mL) and filtered though magnesium sulfate silica gel trap. N-hexane (150 mL) was added and organic phase was evaporated under reduced pressure. Precipitated solid was filtered off and washed with methanol (130 mL) to afford 32 g (90% yield) of MCALDK as colorless solid.

$^1H$ NMR ($CDCl_3$): δ 1.28 (6H, d, J=6.7 Hz), 3.23 (1H, sep, J=6.7 Hz), 3.37 (2H, m), 3.53 (3H, s), 3.57 (3H, s), 4.87-4.92 (1H, m), 5.21-5.24 (1H, m), 6.00-6.09 (1H, m), 7.13 (2H, m), 7.61 (2H, m) ppm. $^{13}C$ NMR ($CDCl_3$): δ 21.9, 31.4, 31.5, 33.1, 42.4, 115.1, 115.3, 116.7, 119.7, 130.7, 130.8, 134.5, 134.6, 136.6, 157.4, 162.1, 164.6, 165.7, 176.6 ppm.

Example 8

Preparation of N-(4-(4-fluorophenyl)-6-isopropyl-5-(prop-1-enyl)pyrimidin-2-yl)-N-methyl-methane-sulfonamide (PMCALDK)

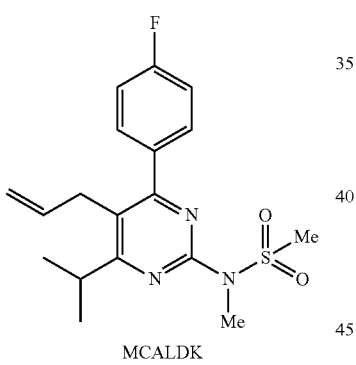

A mixture of MCALDK (0.4 g, 1.1 mmol), KOH (8 M, 28 μL, 0.22 mmol) and ALIQUAT 336 (10 μL, 0.022 mmol) in toluene (8 mL) was stirred at room temperature for 24 hours. Organic phase was washed with water (3×10 mL), brine (2×20 mL), dried over magnesium sulfate and evaporated under reduced pressure to afford 160 mg (80% yield) of PMCALDK as white solid.

$^1$H NMR (CDCl$_3$): δ 1.25 (6H, d, J=6.7 Hz), 1.76-1.78 (3H, m), 3.35-3.42 (1H, m), 3.50 (3H, s), 3.56 (3H, s), 5.48-5.54 (1H, m), 6.25-6.29 (1H, m), 7.08 (2H, m), 7.67 (2H, m) ppm.

Example 9

Preparation of N-(4-(4-fluorophenyl)-6-isopropyl-5-(oxiran-2-ylmethyl)pyrimidin-2-yl)-N-methyl-methanesulfonamide (PMDEPO)

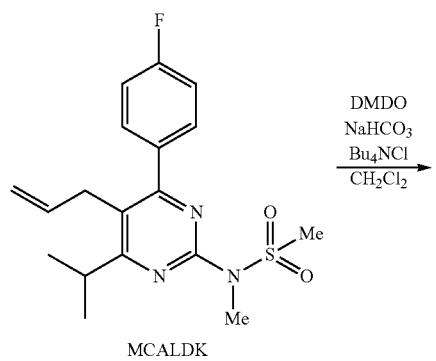

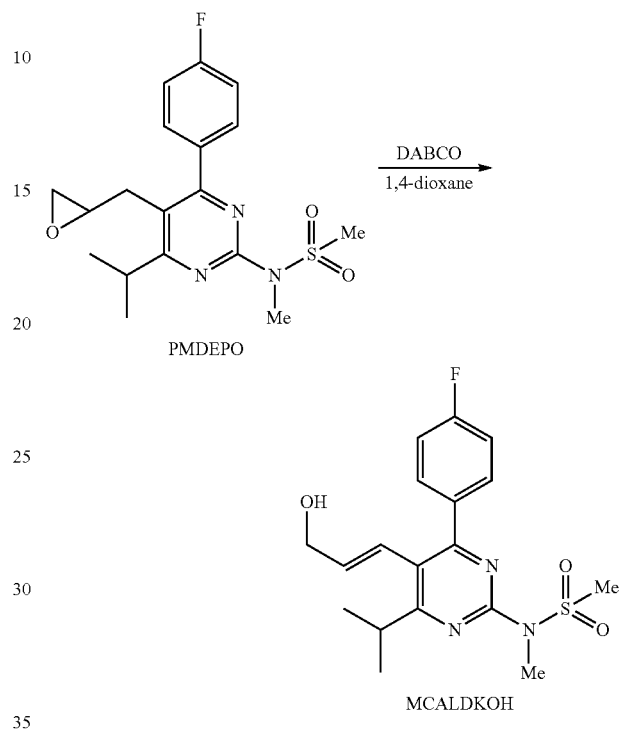

MCALDK (0.73 g, 2 mmol) was dissolved in CH$_2$Cl$_2$ (25 mL) and water (10 mL), NaHCO$_3$ (saturated solution in water, 5 mL), acetone (10 mL) and Bu$_4$NCl (10 mg, 0.2 mmol) were added. The reaction mixture was left to stir at room temperature with continuous addition of NaHCO$_3$ (4.4 g in 50 mL of water) and Oxone (12.3 g in 40 mL of water) over 6 hours. The syringe with Oxone solution was cooled to 0° C. After the complete addition of reactants the solution was stirred for additional 10 hours at room temperature. Water (10 mL) was added and solvent was removed under reduced pressure. Aqueous phase was extracted with dichloromethane (3×10 mL), organic fractions were dried over magnesium sulfate and evaporated to afford 710 mg (95% yield) of PMDEPO as colorless solid.

$^1$H NMR (CDCl$_3$): δ 1.35 (6H, m), 2.32 (1H, m), 2.74 (1H, m), 2.95-3.10 (3H, m), 3.39 (1H, m), 3.53 (3H, s), 3.57 (3H, s), 7.19 (2H, m), 7.57 (2H, m) ppm. $^{13}$C NMR (CDCl$_3$): δ 21.8, 22.1, 29.2, 31.8, 33.1, 42.4, 46.6, 51.5, 115.3, 115.5, 118.1, 130.8, 130.9, 134.6, 157.3, 161.8, 164.3, 166.5, 176.4 ppm.

Example 10

Preparation of (E)-N-(4-(4-fluorophenyl)-5-(3-hydroxyprop-1-enyl)-6-isopropylpyrimidin-2-yl)-N-methylmethanesulfonamide (MCALDKOH)

A mixture of PMDEPO (70 mg, 0.185 mmol) and DABCO (42 mg, 0.37 mmol) in 1,4-dioxane (1 mL) was stirred at 40° C. for 24 hours. Solvent was removed under reduced pressure and resulting oil was redissolved in CH$_2$Cl$_2$ (10 mL). Organic phase was washed with water (10 mL), brine (10 mL), dried over magnesium sulfate and concentrated. Product was purified on colomn chromatography to afford 15 mg (21% yield) of MCALDKOH.

$^1$H NMR (CDCl$_3$): δ 1.27 (6H, d, J=6.7 Hz), 1.60 (1H, s), 3.39 (1H, sep, J=6.7 Hz), 3.52 (3H, s), 3.58 (3H, s), 4.21-4.22 (2H, m), 5.66 (1H, dt, J$_1$=16.2 Hz, J$_2$=5.1 Hz), 6.59 (1H, m), 7.11 (2H, m), 7.66 (2H, m) ppm. $^{13}$C NMR (CDCl$_3$): δ 21.6, 31.9, 33.0, 42.4, 63.1, 114.9, 115.1, 121.1, 123.7, 131.9, 132.0, 134.4, 136.3, 157.3, 161.9, 163.5, 164.5, 174.8 ppm.

Example 11

Preparation of (E)-N-(4-(4-fluorophenyl)-5-(3-hydroxyprop-1-enyl)-6-isopropylpyrimidin-2-yl)-N-methylmethanesulfonamide (MCALDKOH)

MCALDK (363 mg, 1 mmol) was dissolved in CCl$_4$ (8 mL), N-bromosuccinimide (178 mg, 1 mmol) and benzoil peroxide (10 mg, 0.05 mmol) were added. Reaction mixture was stirred at reflux for 18 hours to give MCALDKBR (spectroscopic data: $^1$H NMR (CDCl$_3$): δ 2.03 (6H, d, J=6.7 Hz), 4.11 (1H, sep, J=6.7 Hz), 4.26 (3H, s), 4.32 (3H, s), 4.78 (2H, dd, J$_1$=7.7 Hz J$_2$=0.9 Hz), 6.45-6.53 (1H, m), 7.32-7.36 (1H, m), 7.87 (2H, m), 7.40 (2H, m) ppm. $^{13}$C NMR (CDCl$_3$): δ 21.7, 32.0, 32.2, 33.0, 42.4, 115.1, 115.3, 120.0, 128.3, 132.1, 132.2, 132.4, 133.9, 134.0, 158.0, 162.2, 163.7, 164.7, 171.1, 175.0, ppm).

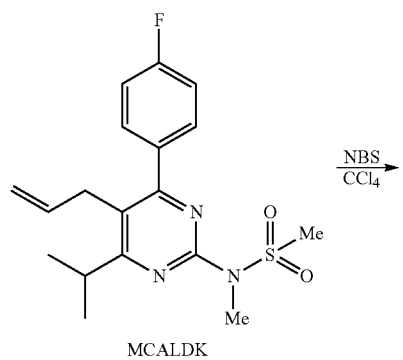

MCALDK

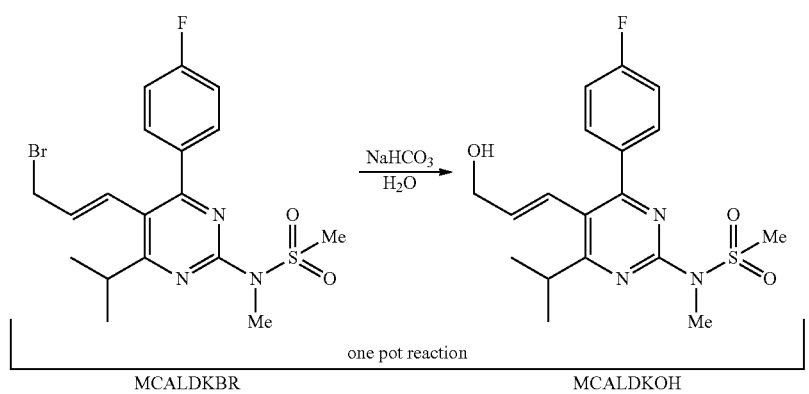

MCALDKBR          MCALDKOH

After, ALIQUAT 336 (0.1 mmol) was added and saturated solution of NaHCO₃ in water (20 mL). Reaction mixture was then heated to 100° C. and stirred for 60 min. After cooling to room temperature, organic phase was separated, dried with brine (10 mL) and magnesium sulfate and concentrated. After concentration the product was purified with colomn chromatography to afford 40 mg (10% yield) of MCALDKOH.

¹H NMR (CDCl₃): δ 1.27 (6H, d, J=6.7 Hz), 1.60 (1H, s), 3.39 (1H, sep, J=6.7 Hz), 3.52 (3H, s), 3.58 (3H, s), 4.21-4.22 (2H, m), 5.66 (1H, dt, J₁=16.2 Hz, J₂=5.1 Hz), 6.59 (1H, m), 7.11 (2H, m), 7.66 (2H, m) ppm. ¹³C NMR (CDCl₃): δ 21.6, 31.9, 33.0, 42.4, 63.1, 114.9, 115.1, 121.1, 123.7, 131.9, 132.0, 134.4, 136.3, 157.3, 161.9, 163.5, 164.5, 174.8 ppm.

Example 12

Preparation of N-(4-(4-fluorophenyl)-5-formyl-6-isopropylpyrimidin-2-yl)-N-methylmethane-sulfonamide (PMDCHO)

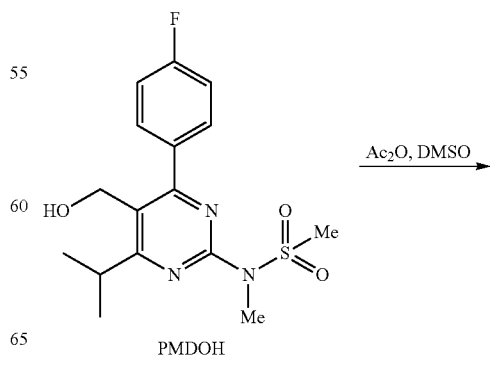

PMDOH

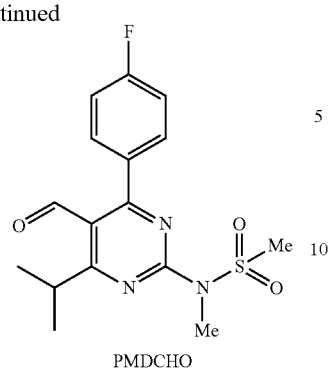

a) from PMDOH:

PMDOH (2.0 g, 5.68 mmol, 1 equiv.) was dissolved in DMSO (10 mL) and reaction mixture was heated to 85° C. Ac$_2$O (4 equiv.) was slowly added (150 µL/h) and reaction was left to stir for 17 hours. Reaction mixture was diluted with H$_2$O (15 mL) and solids were filtered off. Collected precipitate was re-disolved in EtOAc (20 mL), washed with H$_2$O (5 mL) and brine (10 mL). Solvent was evaporated under reduced pressure to give crude solid. Product was further purified by crystallization from EtOAc to afford 0.78 g (39% yield) of PMDCHO as colorless crystals.

b) from PMDBR (Kornblum oxidation):

NaHCO$_3$ (220 mg, 2.6 mmol, 1.1 equiv.) and NaI (10 mol %) were dissolved in DMSO (5 mL) and cooled to 20° C. Then, PMDBR (1.0 g, 2.4 mmol, 1 equiv.) in DMSO (5 mL) was slowly added via a syringe pump during 1 h and reaction was left to stir for 24 h. Reaction mixture was then warmed to 70° C. and Ac$_2$O (5 equiv.) was added dropwise. Reaction was left to stir for additional 3 hours. After cooling on an ice bath, water (20 mL) was slowly added and precipitate was filtered off to afford 0.78 g (93%) of PMDCHO.

$^1$H NMR (CDCl$_3$): δ 1.30 (6H, d, J=6.7 Hz), 3.53 (3H, s), 3.62 (3H, s), 3.99 (1H, sep, J=6.7 Hz), 7.21 (2H, m), 7.61 (2H, m), 9.95 (1H, s) ppm. $^{13}$C NMR (CDCl$_3$): δ 21.6, 31.9, 33.0, 42.4, 115.8, 116.0, 119.5, 132.5, 132.6, 158.7, 163.1, 165.6, 169.7, 178.9, 190.4 ppm.

Example 13

Preparation of (E)-N-(4-(4-fluorophenyl)-6-isopropyl-5-(3-oxoprop-1-enyl)pyrimidin-2-yl)-N-methyl-methanesulfonamide (PMDOPEN)

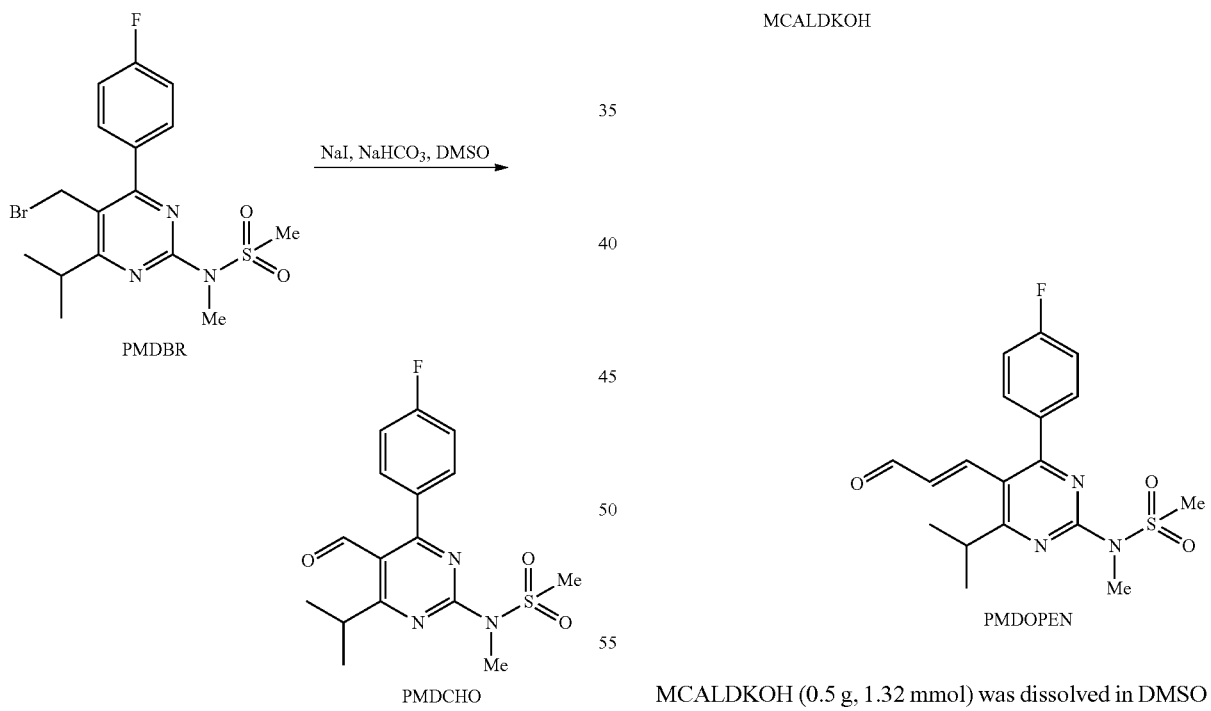

MCALDKOH (0.5 g, 1.32 mmol) was dissolved in DMSO (5 mL) and Ac$_2$O (0.623 µL, 5 equiv.) was added dropwise. Reaction mixture was left to stir at room temperature for 24 hours. H$_2$O (10 mL) and CH$_2$Cl$_2$ (15 mL) were added and mixture was thoroughly mixed in separatory funnel. Phases were separated and water phase was re-extracted with CH$_2$Cl$_2$ (15 mL). Combined organic fractions were washed with H$_2$O (2×10 mL) and dried with brine (2×15 mL) and MgSO$_4$. Solvent was evaporated under reduced pressure and crude product was purified by column chromatography to afford 0.31 g (60% yield) of PMDOPEN as colorless solid.

$^1$H NMR (CDCl$_3$): δ 1.32 (6H, d, J=6.7 Hz), 3.39 (1H, m), 3.52 (3H, s), 3.59 (3H, s), 6.21 (1H, m), 7.14 (2H, m), 7.50-7.62 (3H, m), 9.61 (1H, d, J=7.5 Hz) ppm.

Example 14

Preparation of N-(4-(4-fluorophenyl)-5-formyl-6-isopropylpyrimidin-2-yl)-N-methylmethane-sulfonamide (PMDCHO)

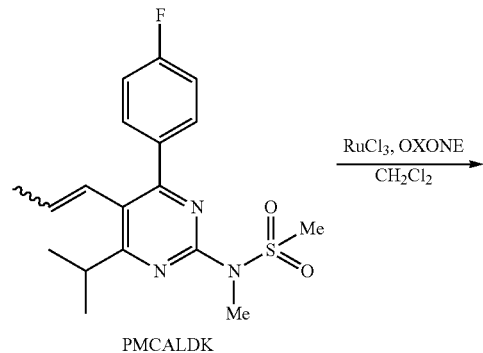

PMCALDK (0.26 g, 0.715 mmol) was dissolved MeCN/H$_2$O=3/2 (5 mL). RuCl$_3$×H$_2$O (3.5 mol %) was added and reaction mixture was stirred at room temperature for 5 min. NaHCO$_3$ (4.7 equiv.) and OXONE (KHSO$_5$×KHSO$_4$×K$_2$SO$_4$, 1.5 equiv.) were added and reaction mixture was left to stir at room temperature for 24 hours. Solids were filtered off and washed with MeCN/H$_2$O=3/2 (15 mL). MeCN was evaporated under reduced pressure and water phase was extracted with CH$_2$Cl$_2$ (3×5 mL). Collected organic phases were dried with brine (2×10 mL), MgSO$_4$ and evaporated under reduced pressure. Residual oil was put on colomn chromatography to afford 105 mg (40% yield) of PMDCHO as colorless crystals.

$^1$H NMR (CDCl$_3$): δ 1.30 (6H, d, J=6.7 Hz), 3.53 (3H, s), 3.62 (3H, s), 3.99 (1H, sep, J=6.7 Hz), 7.21 (2H, m), 7.61 (2H, m), 9.95 (1H, s) ppm. $^{13}$C NMR (CDCl$_3$): δ 21.6, 31.9, 33.0, 42.4, 115.8, 116.0, 119.5, 132.5, 132.6, 158.7, 163.1, 165.6, 169.7, 178.9, 190.4 ppm.

Example 15

Preparation of 1-cyclopropylpropan-1-one (CEK)

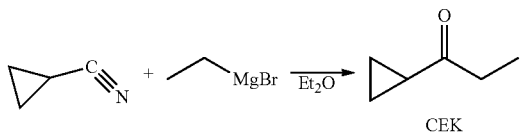

Product was synthesized according to prior publications: *J. Org. Chem.* 1984, 49, 431-435.

Cyclopropanecarbonitrile (20.1 mL, 0.27 mol) was added to dry Et$_2$O (100 mL) under a N$_2$ atmosphere. EtMgBr (100 mL, 3 M in Et$_2$O, 1.1 equiv.) was added dropwise via a syringe. Temperature was controlled by refluxing Et$_2$O and the reaction mixture was kept stirring for 4 hours. Saturated aqueous solution of NH$_4$Cl (150 mL) was then carefully added. Precipitated solids were filtered off and washed thoroughly with NH$_4$Cl (saturated aqueous solution, 50 mL) and Et$_2$O (2×100 mL). Washings were combined with mother liquid and phases were separated. Organic phase was dried with brine (2×100 mL) and MgSO$_4$. Solvent was evaporated under reduced pressure to afford crude oil. Product was purified by distillation at atmospheric pressure to afford 19.0 g (73% yield) of CEK as colorless liquid (boiling point=130° C.).

Example 16

Preparation of 2-cyclopropyl-4-(4-fluorophenyl)-3-methylquinoline (PTVME)

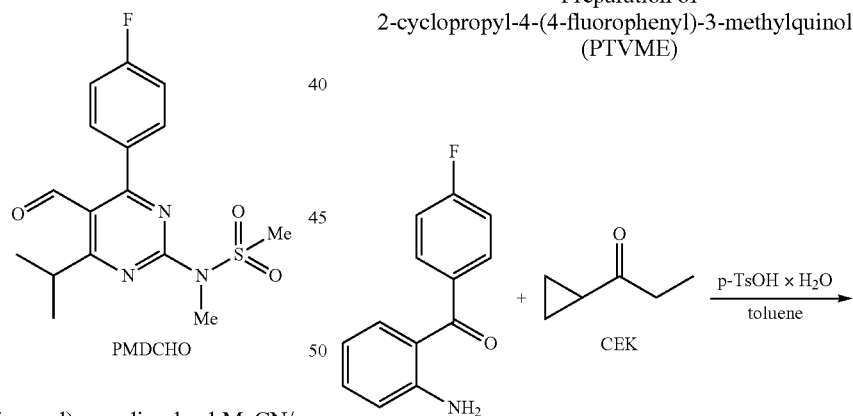

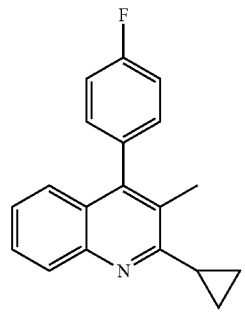

2-amino-4'-fluorobenzophenone (2.15 g, 10 mmol) and p-TsOH×H$_2$O (1.90 g, 1 equiv.) were homogenized and transferred to a pressure reactor. CEK (1.57 g, 1.6 equiv.) and toluene (10 mL) were added and the reactor was sealed. Reaction mixture was left to stir at 105° C. for 24 hours. To the cooled reaction mixture H$_2$O (35 mL) and NaOH (10% aqueous solution, 4 mL) were added. Suspension was transferred to separatory funnel and thoroughly extracted with EtOAc (20 mL). Water phase was re-extracted with EtOAc (2×10 mL), organic fractions were combined and dried with brine (30 mL) and MgSO$_4$. Solvent was evaporated under reduced pressure to give crude brown oil. Product was purified by colomn chromatography to afford 2.8 g (51% yield) of PTVME as a white-yellow solid.

$^1$H NMR (CDCl$_3$): δ 1.07 (2H, m), 1.31 (2H, m), 2.29-2.35 (4H, m), 7.22-7.30 (6H, m), 7.56 (1H, m), 7.97 (1H, m) ppm. $^{13}$C NMR (CDCl$_3$): δ 8.9, 15.3, 16.5, 115.4, 115.6, 125.2, 125.6, 126.5, 127.8, 127.9, 128.8, 131.1, 131.2, 133.7, 133.8, 144.6, 146.1, 161.0, 161.8, 163.5 ppm.

Example 17

Preparation of 3-(bromomethyl)-2-cyclopropyl-4-(4-fluorophenyl)quinoline (PTVBR)

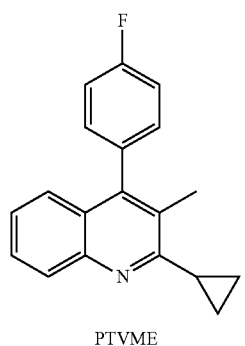

PTVME

NBS
MeCN/CCl$_4$
→

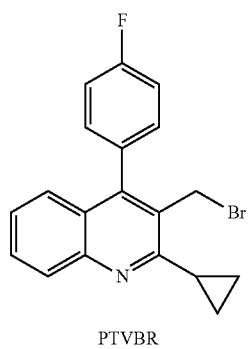

PTVBR

PTVME (0.85 g, 3.06 mmol) and NBS (1.16 g, 2.1 equiv.) were dissolved in MeCN (20 mL) and CCl$_4$ (5 mL). The mixture was irradiated with light of a wavelength λ=254 nm for 4 days at ambient temperature (about 20° C.). After the reaction was complete solvent was removed under reduced pressure and residual oil was redissolved in 0H$_2$Cl$_2$ (20 mL). Organic phase was washed with saturated Na$_2$S$_2$O$_3$ (1×10 mL), saturated NaHCO$_3$ solution (2×10 mL), brine (1×10 mL) and dried over MgSO$_4$. Solvent was removed under reduced pressure and product was purified by column chromatography (gradient 1-10% of EtOAc in n-heptane) to give 0.22 g (20% yield) of PTVBR.

$^1$H NMR (CDCl$_3$): δ 1.17 (2H, m), 1.40 (2H, m), 2.50-2.54 (1H, m), 4.6 (2H, s), 7.24-7.40 (6H, m), 7.64 (1H, m), 8.00-8.02 (1H, m) ppm. $^{13}$C NMR (CDCl$_3$): δ 9.8, 14.7, 29.1, 115.6, 115.8, 125.8, 126.2, 126.4, 127.4, 128.5, 128.8, 129.7, 130.87, 130.91, 131.0, 131.60, 131.63, 146.9, 147.1, 161.4, 161.5, 163.9 ppm.

Example 18

Preparation of (2-cyclopropyl-4-(4-fluorophenyl)quinolin-3-yl)methanol (PTVOH)

PTVBR

1. H$_2$O/THF
2. NaHCO$_3$ (aq.)
→

PTVOH

A mixture of 3-(bromomethyl)-2-cyclopropyl-4-(4-fluorophenyl)quinolone (PTVBR) (1.0 g), water (20 mL) and tetrahydrofurane (20 mL) was stirred under reflux conditions for 56 hours. Tetrahydrofurane was distilled off, saturated aqueous solution of NaHCO$_3$ (20 mL) was added and the product was extracted with dichlorometane (2×25 mL). The combined dichloromethane fractions were dried over Na$_2$SO$_4$, filtered and concentrated. To the residue were added dichloromethane (5 mL) and heptane (10 mL). The precipitate was filtered off and dried to yield 0.65 g (79% yield) of (2-cyclopropyl-4-(4-fluorophenyl)quinolin-3-yl)methanol (PTVOH).

$^1$H NMR (CDCl$_3$): δ 1.00 (2H, m), 1.28 (2H, m), 2.50 (1H, m), 4.65 (2H, s), 7.05-7.27 (6H, m), 7.51 (1H, m), 7.88 (1H, m) ppm. $^{13}$C NMR (CDCl$_3$): d 9.8, 14.5, 59.6, 115.4, 115.6, 125.5, 126.1, 126.4, 128.9, 129.2, 129.3, 131.2, 131.3, 132.3, 132.4, 146.4, 147.3, 161.6, 162.2, 163.5 ppm.

Example 19

Preparation of 2-cyclopropyl-4-(4-fluorophenyl)quinoline-3-carbaldehyde (PTVCHO) by Kornblum oxidation

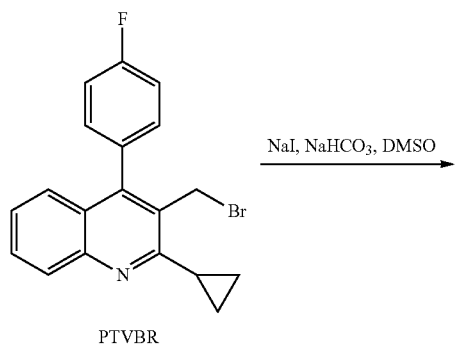

PTVBR

→ NaI, NaHCO₃, DMSO

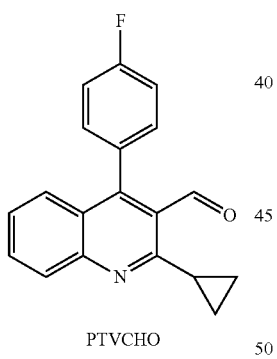

PTVCHO

A mixture of 3-(bromomethyl)-2-cyclopropyl-4-(4-fluorophenyl)quinolone (PTVBR) (0.86 g), sodium iodide (0.04 g), NaHCO₃ (0.22 g) and dimethylsulfoxide (10 mL) was stirred at 25° C. for 56 hours. Water (20 mL) and tert-butyl methyl ether (10 mL) were added. Phases were separated and water phase was re-extracted with tert-butyl methyl ether (10 mL). Combined tert-butyl methyl ether phases were washed with water (10 mL) followed by brine (10 mL) and concentrated. The residual material was purified by chromatography (silica gel; hexane:toluene 25:75→0:100) to yield 0.42 g (60% yield) of 2-cyclopropyl-4-(4-fluorophenyl)quinoline-3-carbaldehyde (PTVCHO).

$^{1}$H NMR (CDCl$_3$): δ 1.01 (2H, m), 1.30 (2H, m), 3.13 (1H, m), 7.10-7.39 (6H, m), 7.64 (1H, m), 7.88 (1H, m), 9.97 (1H, s) ppm. $^{13}$C NMR (CDCl$_3$): δ 11.3, 14.5, 115.6, 115.8, 125.2, 126.0, 126.1, 126.5, 129.9, 130.0, 131.3, 131.4, 131.8, 131.9, 132.0, 148.9, 152.8, 161.6, 162.0, 164.0, 193.6 ppm.

Example 20

Preparation of 1-cyclopropylbut-3-en-1-one

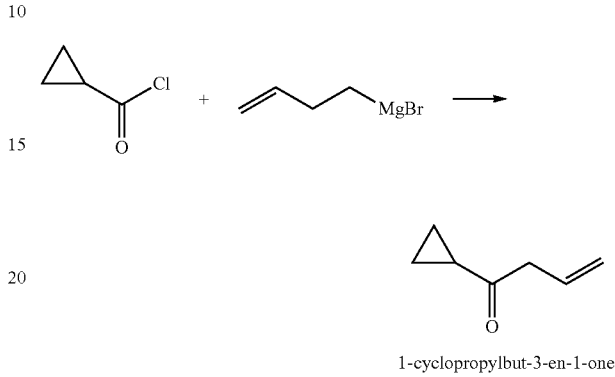

1-cyclopropylbut-3-en-1-one

Dry THF (20 mL) was added to a sealed and nitrogen flushed vessel, which was then left to cool to −40° C. Cyclopropanecarbonyl chloride (1 equiv., 9.2 mmol, 0.96 g) was added and reaction mixture was left to stir for 10 minutes. But-3-en-1-ylmagnesium bromide (0.5 M in THF, 1.1 equiv., 10.6 mmol, 21 mL) was added via a syringe during 30 min and mixture was left to stir at −40° C. for 24 h. Reaction was quenched with the addition of saturated water solution of NH$_4$Cl (10 mL) and warmed to room temperature. Solids were filtered off and washed with THF (3×40 mL). Filtrate was evaporated under reduced pressure and water phase extracted with CH$_2$Cl$_2$ (2×20 mL). Combined organic phases were dried over MgSO$_4$ and evaporated under reduced pressure. Product was purified by column chromatography to give 0.74 g (70% yield) of 1-cyclopropylbut-3-en-1-one with the same characteristics as described in *Zhurnal Organicheskoi Khimii*, 1987, 23, 515-521 and *Zhurnal Organicheskoi Khimii*, 1984, 20, 652-653.

Example 21

Preparation of 3-allyl-2-cyclopropyl-4-(4-fluorophenyl)quinolone (PTVA)

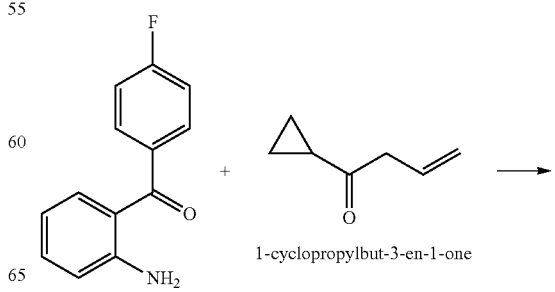

1-cyclopropylbut-3-en-1-one

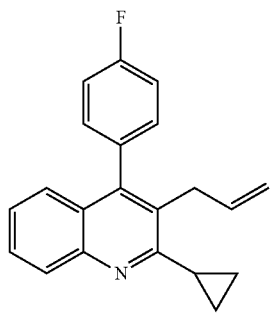

PTVA

2-Amino-4'-fluorobenzofenone (1 equiv., 4.3 mmol, 0.92 g), p-TsOH×H$_2$O (1.5 equiv., 1.23 g) and 1-cyclopropylbut-3-en-1-one (1.5 equiv., 0.8 g) were added into a pressure reactor. Reactor was sealed and heated on oil bath (110° C.) for 15 min after which it was opened and reaction mixture was homogenized. Procedure was repeated once more and reaction mixture was left to stir for 24 h at 110° C. Reaction mixture was then transferred to separatory funnel and EtOAc (10 mL) and H$_2$O (35 mL) were added and phases separated. Water phase was further extracted with EtOAc (3×20 mL). Organic extracts were combined, washed with brine (1×15 mL) and dried over MgSO$_4$. Solvent was evaporated under reduced pressure. Product was purified by column chromatography to give 0.63 g (48% yield) of PTVA.

$^1$H NMR (CDCl$_3$): δ ☐ 1.05 (2H, m), 1.35 (2H, m), 2.36 (1H, m), 3.50 (2H, m), 4.82 (1H, m), 5.08 (1H, m), 5.99 (1H, m), 7.18-7.33 (6H, m), 7.59 (1H, m), 7.99 (1H, m) ppm.

Example 22

Preparation of 2-cyclopropyl-4-(4-fluorophenyl)-3-(oxiran-2-ylmethyl)quinolone (PTVEPOKSI)

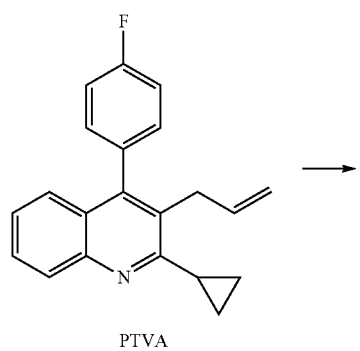

PTVA

→

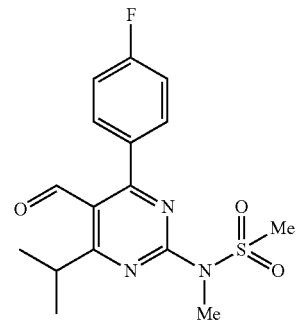

PTVEPOKSI

PTVA (1 equiv., 2.97 mmol, 0.90 g) and Bu$_4$NCl (7 mol %) were dissolved in CH$_2$Cl$_2$ (30 mL) followed by addition of H$_2$O (15 mL), acetone (10 mL) and saturated NaHCO$_3$ solution (5 mL). The reaction vessel was flushed with N$_2$ and sealed. Then oxone (10 equiv. dissolved in 60 mL of H$_2$O) and NaHCO$_3$ (26 equiv. dissolved in 60 mL of H$_2$O) were added separately during 8 h (reaction mixture was kept constant at room temperature). After complete addition, reaction was left to stir at room temperature for additional 16 h. After the phases were separated and water phase further extracted with CH$_2$Cl$_2$ (1×20 mL). Organic fractions were combined, washed with brine (20 mL) and dried over MgSO$_4$. Solvent was evaporated and product purified by column chromatography to give 0.62 g (65% yield) of PTVEPOKSI. $^1$H NMR (CDCl$_3$): δ 1.10 (2H, m), 1.33 (1H, m), 1.45 (1H, m), 2.29 (1H, m), 2.46 (1H, m), 270 (1H, m), 2.99 (1H, m), 3.16 (1H, m), 3.22 (1H, m), 7.18-7.33 (6H, m), 7.60 (1H, m), 7.97 (1H, m) ppm.

The invention claimed is:

1. A process for the preparation of Rosuvastatin or pharmaceutically acceptable salt of Rosuvastatin, comprising the steps of:

a) carrying out a process for preparing the compound of formula (Ia) comprising (Ia)

a-1) either subjecting a heterocyclic methyl derivative (III-Me)

HET-CH$_3$ (III-Me)

to radical bromination reaction to obtain an intermediate (IV)

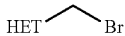
(IV)

and subsequently to a nucleophilic substitution reaction to obtain a compound of formula (V)

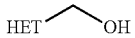
(V)

and oxidizing the compound of formula (IV) or (V) to the heterocyclic aldehyde (I)

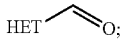
(I)

or a-2) converting a compound of formula (III-aI)

(III-aI)

to a compound of the formula (VII) by isomerization

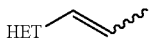
(VII)

and oxidizing the compound of formula (VII) to the heterocyclic aldehyde (I)

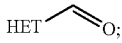
(I)

wherein a heterocyclic group HET denotes a substituted pyrimidine of the structure (a)

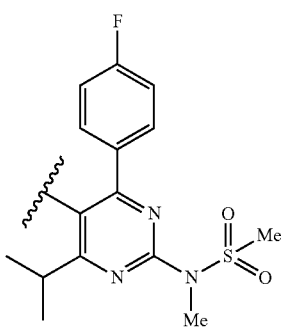
(a)

or b) carrying out a process for preparing the compound of formula (IIa) comprising

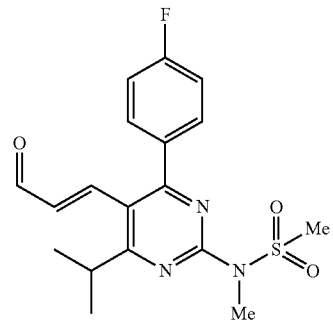
(IIa)

converting the compound of formula (III-aI) defined above to a compound of formula (VIII)

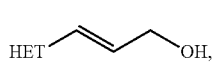
(VIII)

and oxidizing the compound of formula (VIII) to the heterocyclic aldehyde (II)

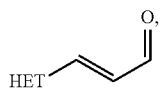
(II)

wherein a heterocyclic group HET denotes a substituted pyrimidine of the structure (a)

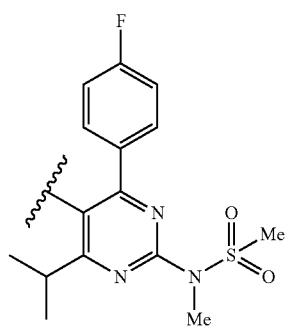
(a)

and c) subjecting the compound of formula (Ia) or the compound of formula (IIa) respectively to further synthesis steps to yield Rosuvastatin or pharmaceutically acceptable salts thereof.

2. A process for the preparation of a pharmaceutical composition comprising Rosuvastatin as active ingredient, comprising the steps of:
a) preparing Rosuvastatin or pharmaceutically acceptable salts thereof according to the process according to claim 1, and
b) admixing the thus prepared Rosuvastatin or pharmaceutically acceptable salt thereof with at least one pharmaceutically acceptable excipient.

3. The process according to claim 1 for preparing the aldehyde (IIa), wherein the aldehyde (Ia) is prepared and subsequently converted to the aldehyde (IIa) according to any one of the following alternatives (i), (ii), (iii) or (iv):

(i) by reacting the aldehyde (Ia) with a dioxolanymethyl nucleophile to the intermediate (X);

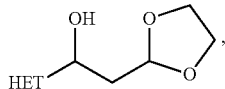

(X)

dehydrating the intermediate (X) to the intermediate (XI) and

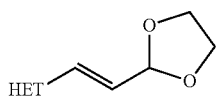

(XI)

transforming the intermediate (XI) to the aldehyde (IIa) by deprotection, wherein the heterocyclic substituent HET is a substituted pyrimidine of the structure (a)

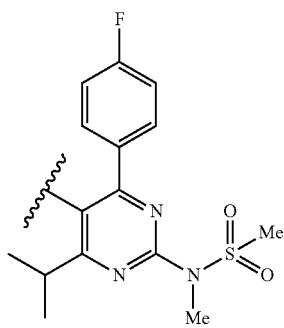

(a)

(ii) by subjecting the aldehyde (Ia) to a Wittig type reaction with dioxolanylmethylenetriphenylphosphane to obtain the intermediate (XI), and

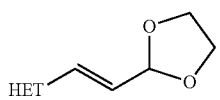

(XI)

deprotecting the intermediate (XI) to obtain the aldehyde (IIa), wherein the heterocyclic substituent HET is a substituted pyrimidine of the structure (a)

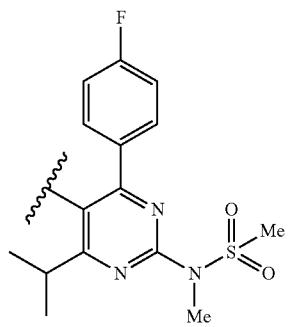

(a)

(iii) by reacting the aldehyde (Ia) with acetaldehyde, wherein the heterocyclic substituent HET is a substituted pyrimidine of the structure (a)

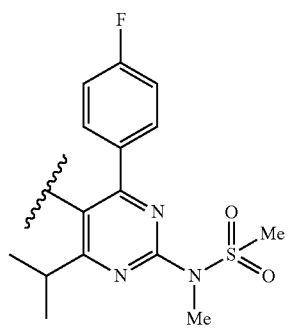

(a)

(iv) by reaction with ethylpyruvate in the presence of pyruvate decarboxylase, wherein the heterocyclic substituent HET is a substituted pyrimidine of the structure (a)

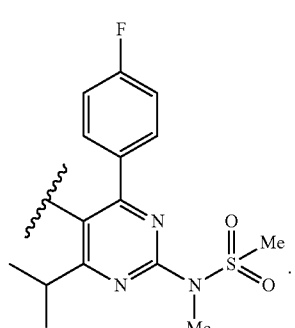

(a)

4. A process for preparing a heterocyclic alkyl derivative of formula (IIIa)

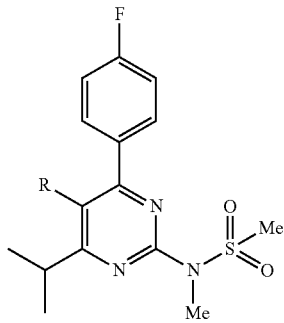

wherein R is a straight or branched, saturated or unsaturated, optionally substituted alkyl moiety,
the process comprising:
converting the diketone compound of formula (XIIa) to an alkylated diketone of formula (XIVa)

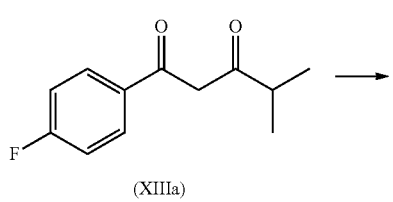

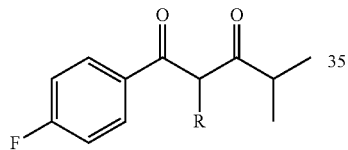

wherein R is a straight or branched, saturated or unsaturated, optionally substituted alkyl moiety,
reacting the alkylated diketone of formula (XIVa) with N-methyl guanidine or a salt thereof to the heterocyclic compound of formula (XVa)

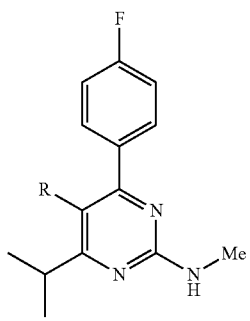

wherein R is a straight or branched, saturated or unsaturated, optionally substituted alkyl moiety, and
converting the heterocyclic compound of formula (XVa) to a sulfonated alkyl heterocycle of formula (IIIa)

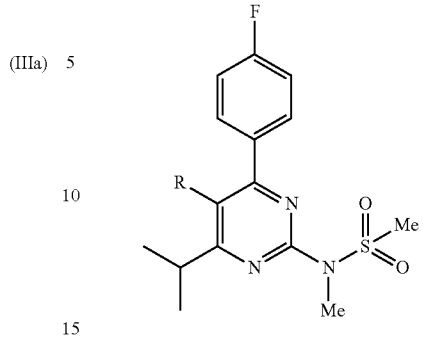

wherein R is a straight or branched, saturated or unsaturated, optionally substituted alkyl moiety.

5. The process according to claim 1, wherein the heterocyclic compound (III-Me) is the compound of formula (III-Me-a)

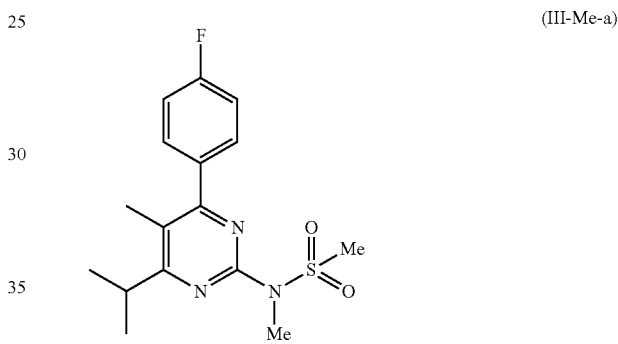

which is prepared by converting the diketone compound of formula (XIIIa) to an methylated diketone compound of formula (XIV-Me-a);

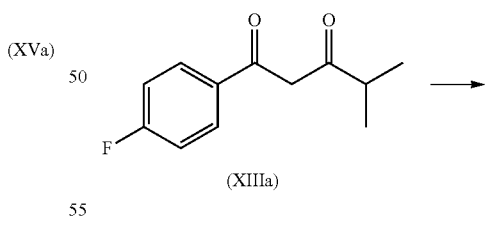

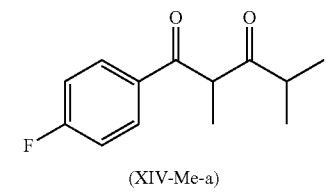

reacting the methylated diketone compound of formula (XIV-Me-a) with N-methyl guanidine or a salt thereof to the heterocyclic compound of formula (XV-Me-a); and

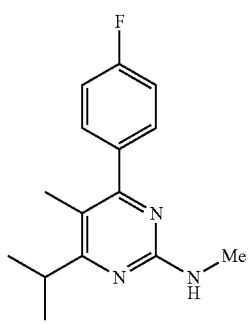
(XV-Me-a)

converting the heterocyclic compound of formula (XV-Me-a) to a sulfonated methyl heterocyle of formula (III-Me-a)

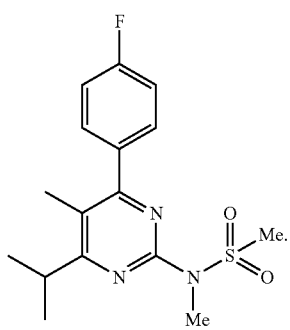
(III-Me-a)

6. The process according to claim 1, wherein the heterocyclic compound (III-aI) is the compound of formula (III-aI-a)

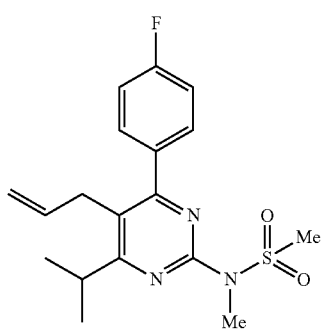
(III-aI-a)

which is prepared by
converting the diketone compound of formula (XIIIa) to an allylated diketone compound of formula (XIV-aI-a);

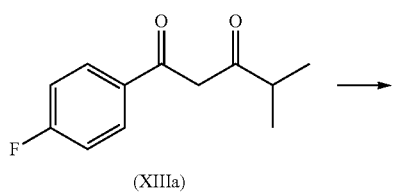
(XIIIa)

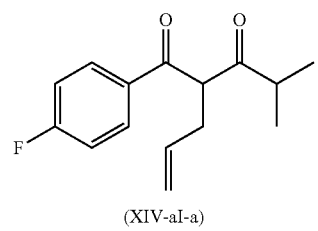
(XIV-aI-a)

reacting the allylated diketone compound of formula (XIV-aI-a) with N-methyl guanidine or a salt thereof to the heterocyclic compound of formula (XV-aI-a); and

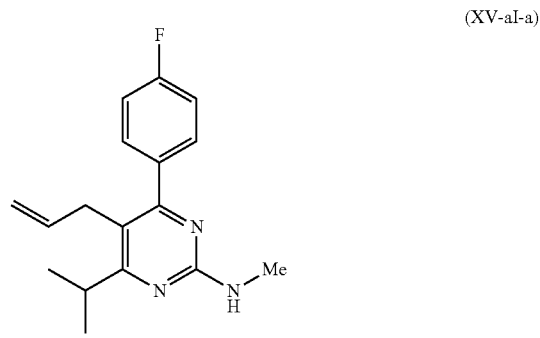 [SMILES: C=CCc1c(-c2ccc(F)cc2)nc(NC)nc1C(C)C]
(XV-aI-a)

converting the heterocyclic compound of formula (XV-aI-a) to a sulfonated methyl heterocyle of formula (III-aI-a)

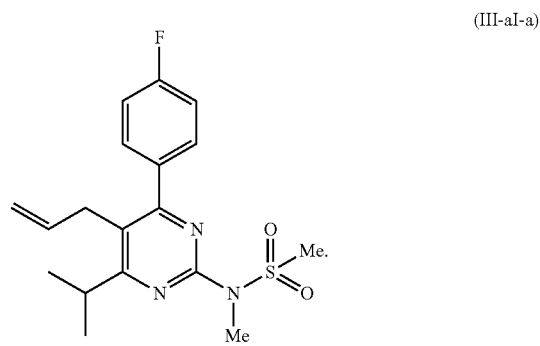 [SMILES: C=CCc1c(-c2ccc(F)cc2)nc(N(C)S(C)(=O)=O)nc1C(C)C]
(III-aI-a)

7. A process for the preparation of Rosuvastatin or pharmaceutically acceptable salt of Rosuvastatin, comprising the steps of:

a) carrying out a process for preparing the heterocyclic alkyl derivative of formula (IIIa)

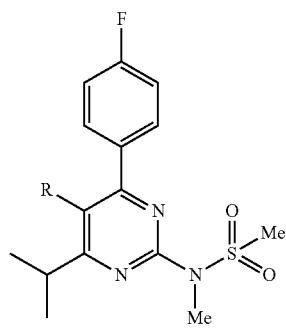

(IIIa)

wherein R is a straight or branched, saturated or unsaturated, optionally substituted alkyl moiety, the process comprising:

converting the diketone compound of formula (XIIIa) to an alkylated diketone of formula (XIVa)

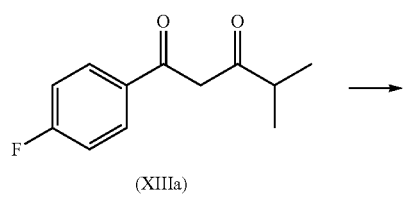

(XIIIa)

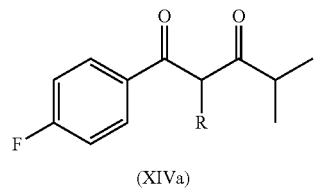

(XIVa)

wherein R is a straight or branched, saturated or unsaturated, optionally substituted alkyl moiety, reacting the alkylated diketone of formula (XIVa) with N-methyl guanidine or a salt thereof to the heterocyclic compound of formula (XVa)

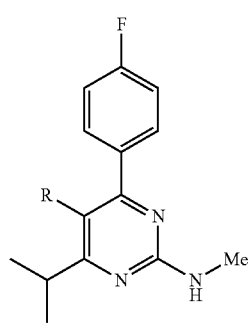

(XVa)

wherein R is a straight or branched, saturated or unsaturated, optionally substituted alkyl moiety, and converting the heterocyclic compound of formula (XVa) to a sulfonated alkyl heterocycle of formula (IIIa)

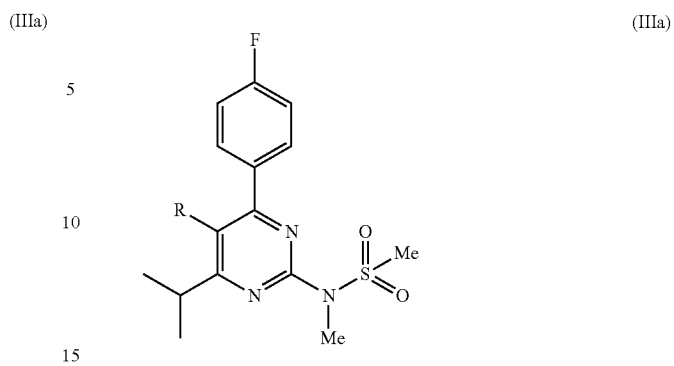

(IIIa)

wherein R is a straight or branched, saturated or unsaturated, optionally substituted alkyl moiety, and b) subjecting the compound of formula (IIIa) to further synthesis steps to yield Rosuvastatin or pharmaceutically acceptable salts thereof.

8. A process for the preparation of a pharmaceutical composition comprising Rosuvastatin as active ingredient, comprising the steps of:

a) preparing Rosuvastatin or pharmaceutically acceptable salts thereof according to the process according to claim 7, and b) admixing the thus prepared Rosuvastatin or pharmaceutically acceptable salt thereof with at least one pharmaceutically acceptable excipient.

9. The process according to claim 7, wherein the heterocyclic compound (IIIa) is the compound of formula (III-Me-a)

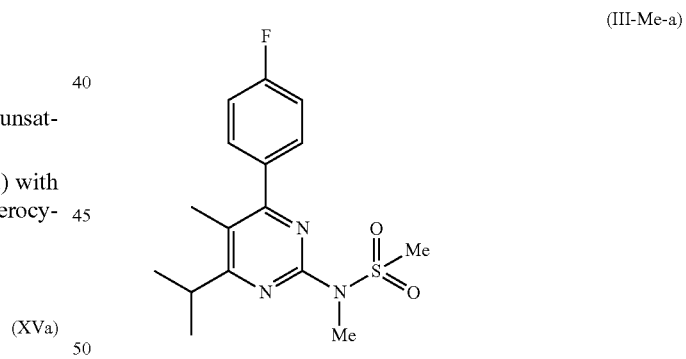

(III-Me-a)

which is prepared by converting the diketone compound of formula (XIIIa) to a methylated diketone compound of formula (XIV-Me-a);

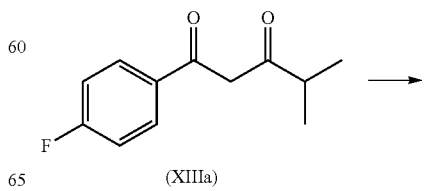

(XIIIa)

-continued

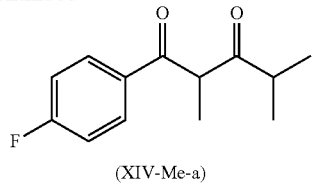

(XIV-Me-a)

reacting the methylated diketone compound of formula (XIV-Me-a) with N-methyl guanidine or a salt thereof to the heterocyclic compound of formula (XV-Me-a); and (XV-Me-a)

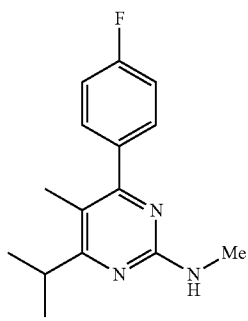

converting the heterocyclic compound of formula (XV-Me-a) to a sulfonated methyl heterocyle of formula (III-Me-a)

(III-Me-a)

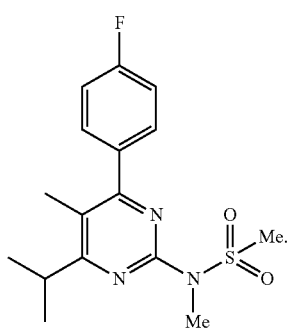

10. The process according to claim 1, wherein the heterocyclic compound (IIIa) is the compound of formula (II-aI-a)

(III-aI-a)

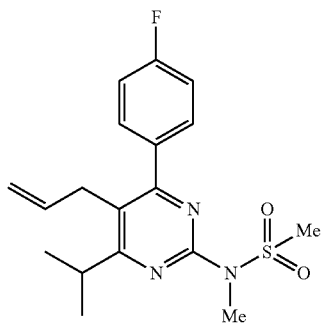

which is prepared by converting the diketone compound of formula (XIIIa) to an allylated diketone compound of formula (XIV-al-a);

(XIIIa)

(XIV-aI-a)

reacting the allylated diketone compound of formula (XIV-al-a) with N-methyl guanidine or a salt thereof to the heterocyclic compound of formula (XV-al-a); and (XV-aI-a)

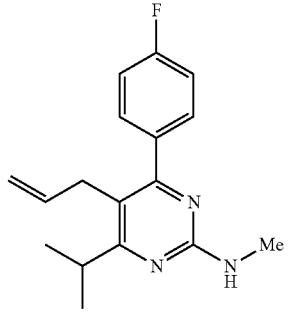

converting the heterocyclic compound of formula (XV-al-a) to a sulfonated methyl heterocyle of formula (III-al-a)

(III-aI-a)

* * * * *